(12) United States Patent
Abreu

(10) Patent No.: US 11,596,358 B2
(45) Date of Patent: Mar. 7, 2023

(54) APPARATUS FOR MEASURING A PARAMETER OF A HUMAN BODY AT AN ABREU BRAIN THERMAL TUNNEL (ABTT)

(71) Applicant: Brain Tunnelgenix Technologies Corp., Aventura, FL (US)

(72) Inventor: Marcio Marc Abreu, Aventura, FL (US)

(73) Assignee: Brain Tunnelgenix Technologies Corp., Aventura, FL (US)

( * ) Notice: Subject to any disclaimer, the term of this patent is extended or adjusted under 35 U.S.C. 154(b) by 0 days.

(21) Appl. No.: 15/067,030

(22) Filed: Mar. 10, 2016

(65) Prior Publication Data

US 2016/0262701 A1  Sep. 15, 2016

Related U.S. Application Data

(60) Provisional application No. 62/131,056, filed on Mar. 10, 2015.

(51) Int. Cl.
*A61B 5/00* (2006.01)
*A61B 5/01* (2006.01)

(52) U.S. Cl.
CPC .............. *A61B 5/6898* (2013.01); *A61B 5/01* (2013.01); *A61B 5/4064* (2013.01); *A61B 5/742* (2013.01)

(58) Field of Classification Search
CPC .......... A61B 5/6898; A61B 5/01; A61B 5/742
See application file for complete search history.

(56) References Cited

U.S. PATENT DOCUMENTS

| 7,787,663 | B2* | 8/2010 | Hartlove | G01J 5/0025 374/121 |
| 2003/0044000 | A1 | 3/2003 | Kfoury et al. | |
| 2003/0179094 | A1* | 9/2003 | Abreu | A61B 5/0002 340/573.1 |
| 2004/0059212 | A1* | 3/2004 | Abreu | A61B 5/14553 374/E13.002 |
| 2004/0242976 | A1* | 12/2004 | Abreu | A61B 5/746 600/315 |
| 2006/0217148 | A1 | 9/2006 | Cok | |
| 2007/0106172 | A1* | 5/2007 | Abreu | A61B 5/0002 600/549 |
| 2008/0077019 | A1* | 3/2008 | Xiao | A61B 5/01 600/474 |
| 2009/0105605 | A1* | 4/2009 | Abreu | A61B 5/4076 600/549 |
| 2009/0110404 | A1* | 4/2009 | Agevik | H01R 24/58 398/115 |
| 2012/0130145 | A1* | 5/2012 | Sabol | A61B 6/5211 600/1 |

(Continued)

OTHER PUBLICATIONS

Notification of Transmittal of the International Search Report and the Written Opinion of the International Searching Authority; PCT/US2016/021853 dated Aug. 16, 2016.

(Continued)

*Primary Examiner* — Sean P Dougherty
(74) *Attorney, Agent, or Firm* — Studebaker & Brackett PC

(57) ABSTRACT

The physical and physiological events at one end of an Abreu Brain Thermal Tunnel (ABTT) are reproduced at the opposite end. Thus, the ABTT enables the direct transfer of outputs from a brain core to an ABTT terminus without significant barriers. Accordingly, apparatuses, systems, devices, mechanisms, and methods use the ABTT terminus and the ABTT to measure the temperature of the brain core.

9 Claims, 62 Drawing Sheets

(56) References Cited

U.S. PATENT DOCUMENTS

| | | | |
|---|---|---|---|
| 2012/0231841 A1 | 9/2012 | Niederberger et al. | |
| 2013/0131541 A1* | 5/2013 | Tsai | A61B 10/0012 600/551 |
| 2014/0193157 A1* | 7/2014 | Du | G08C 23/04 398/106 |
| 2015/0094914 A1* | 4/2015 | Abreu | B60H 1/00742 701/1 |
| 2015/0105687 A1* | 4/2015 | Abreu | A61B 5/4812 600/549 |
| 2015/0148628 A1* | 5/2015 | Abreu | A61B 5/021 600/323 |
| 2015/0196203 A1* | 7/2015 | Abreu | A61B 5/742 600/549 |
| 2015/0209174 A1* | 7/2015 | Abreu | A61F 7/02 607/104 |
| 2016/0150976 A1* | 6/2016 | Fang | A61B 5/7282 600/474 |
| 2016/0262629 A1* | 9/2016 | Abreu | A61B 5/01 |
| 2016/0262701 A1* | 9/2016 | Abreu | A61B 5/6898 |
| 2016/0262924 A1* | 9/2016 | Abreu | A43B 7/005 |
| 2016/0287087 A1* | 10/2016 | Abreu | A61B 5/7275 |
| 2016/0296168 A1* | 10/2016 | Abreu | A61B 5/01 |
| 2018/0094983 A1* | 4/2018 | Tierney | G01J 5/18 |

OTHER PUBLICATIONS

International Preliminary Report on Patentability dated Sep. 21, 2017, issued in International Application No. PCT/US2016/021853; 7pp.

* cited by examiner

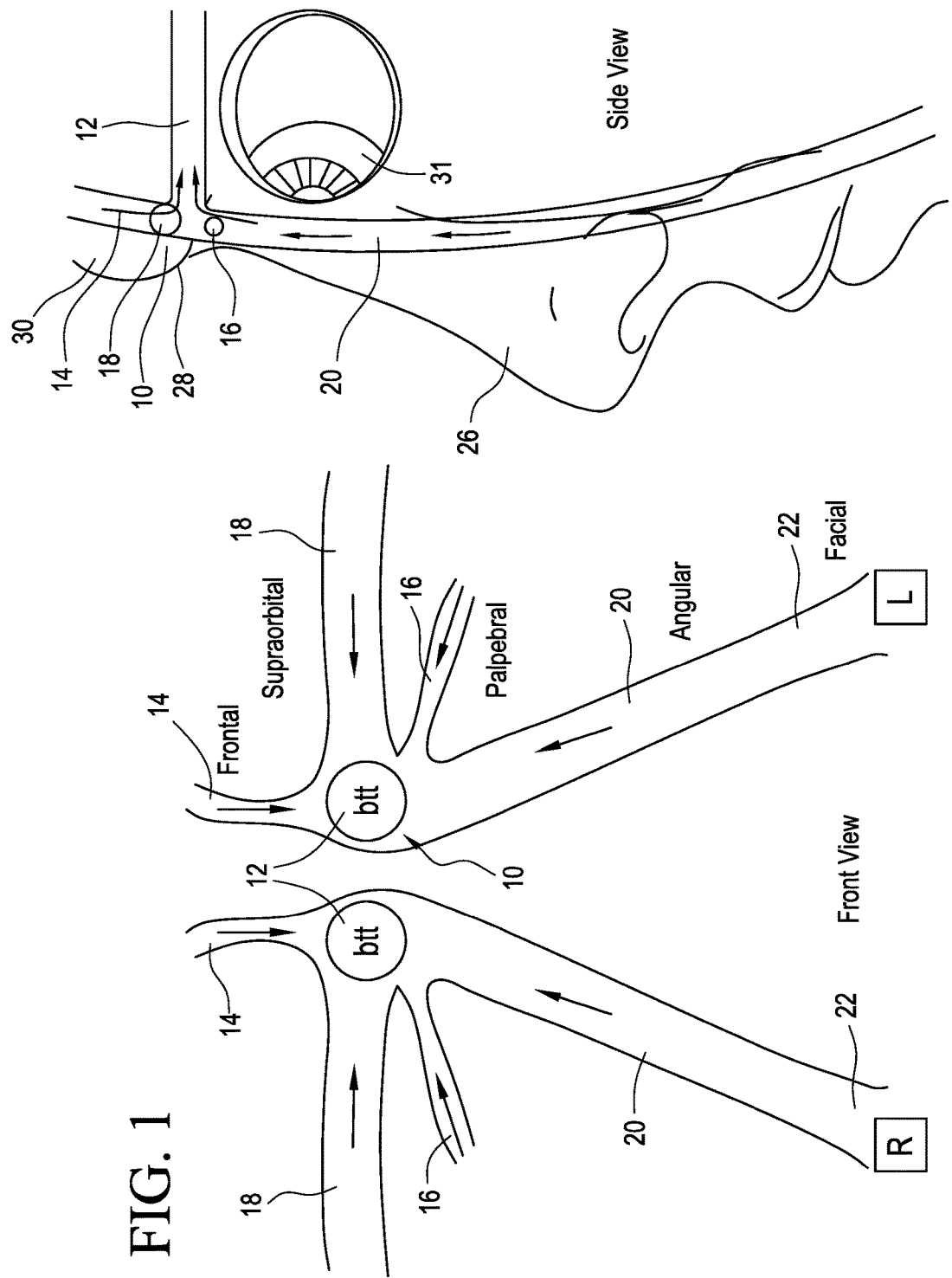

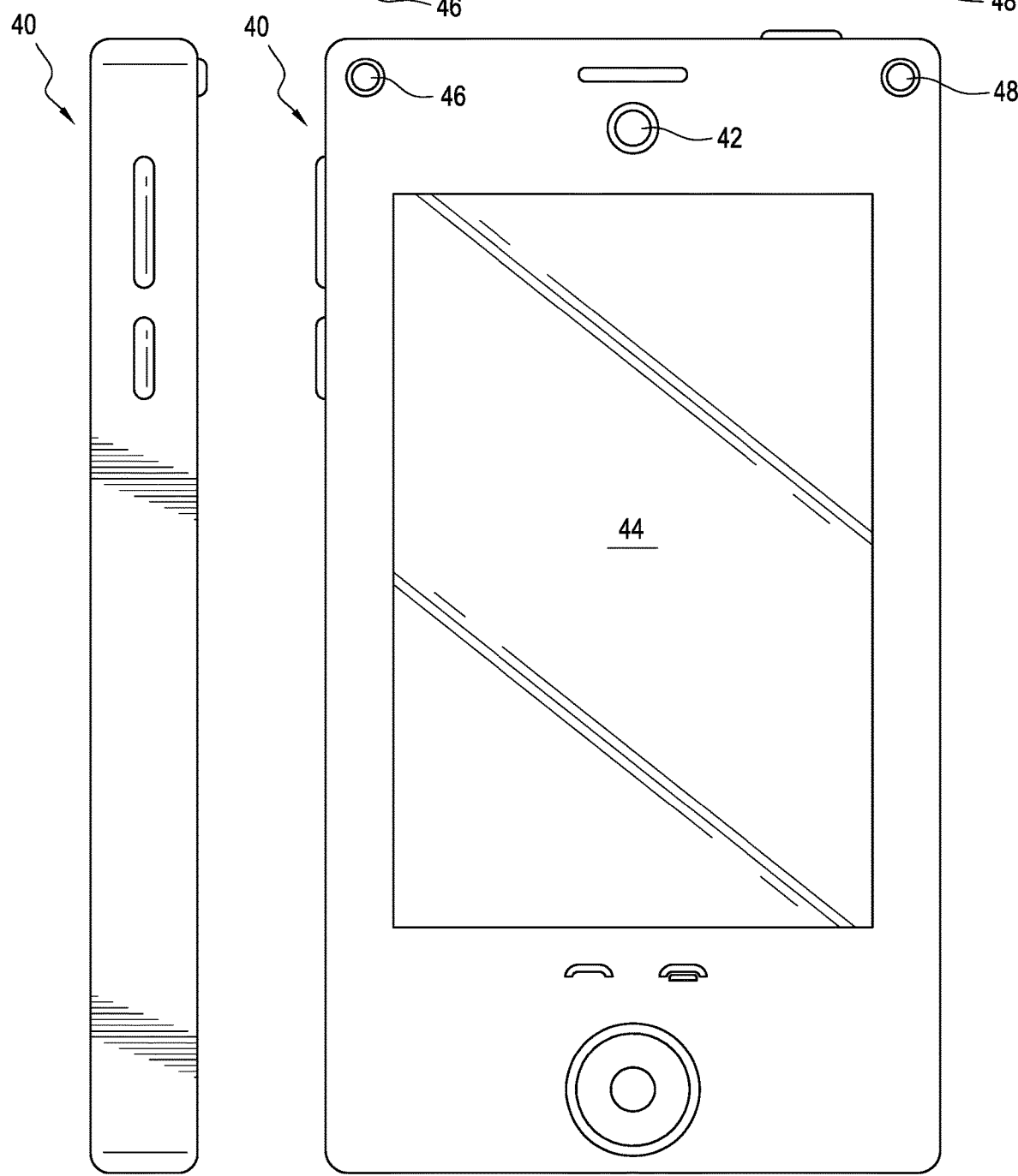

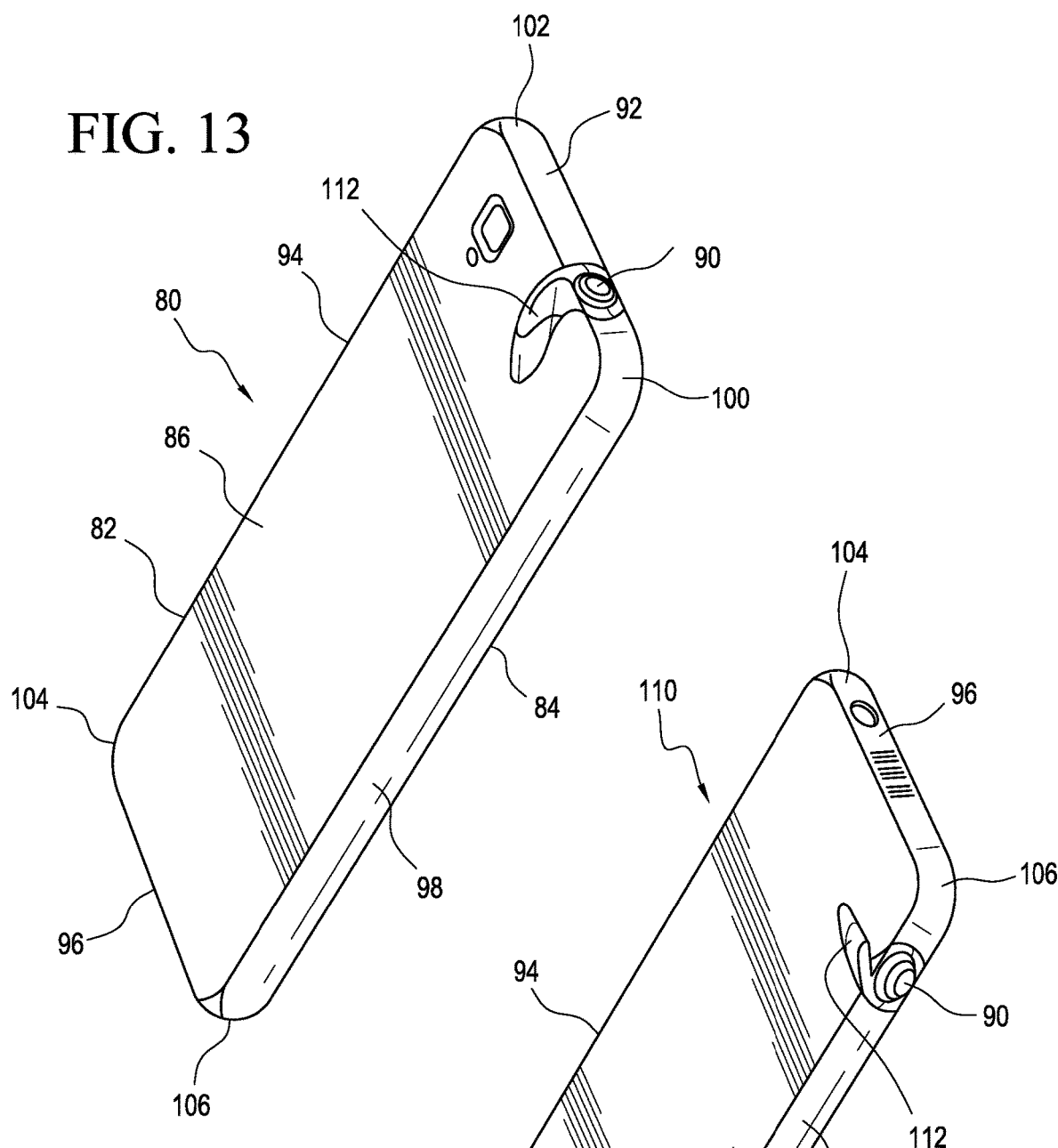

FIG. 20
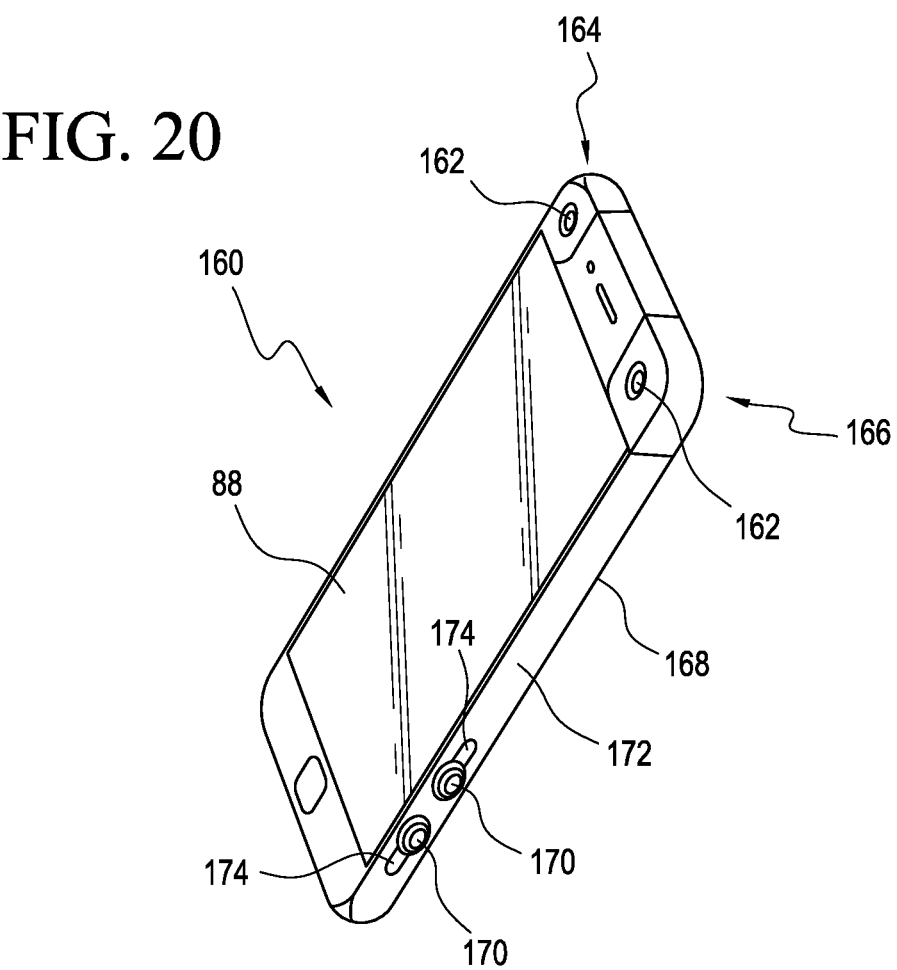
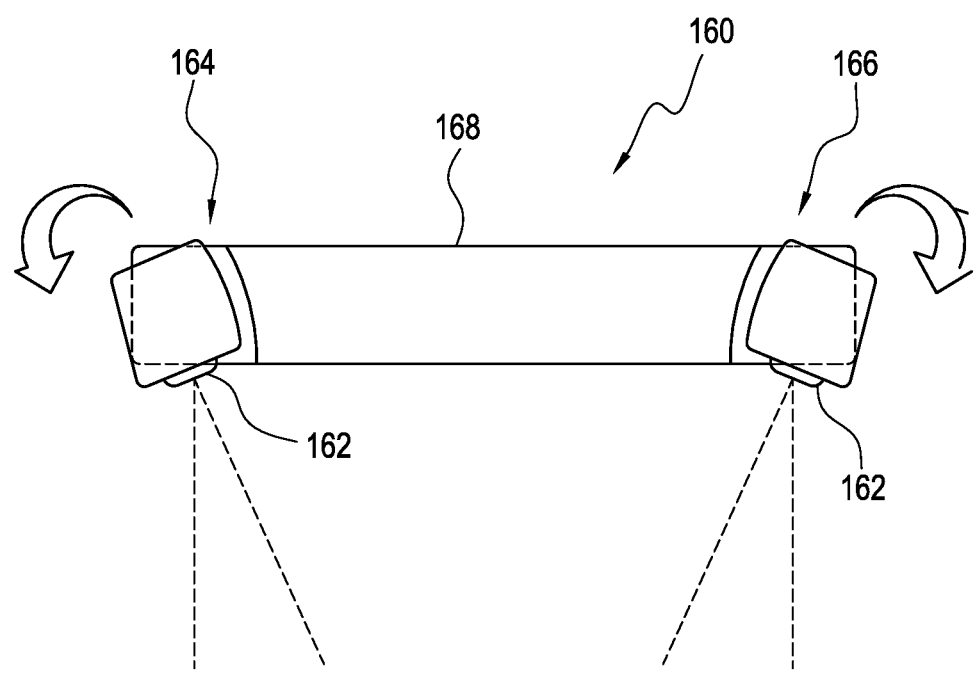
FIG. 21

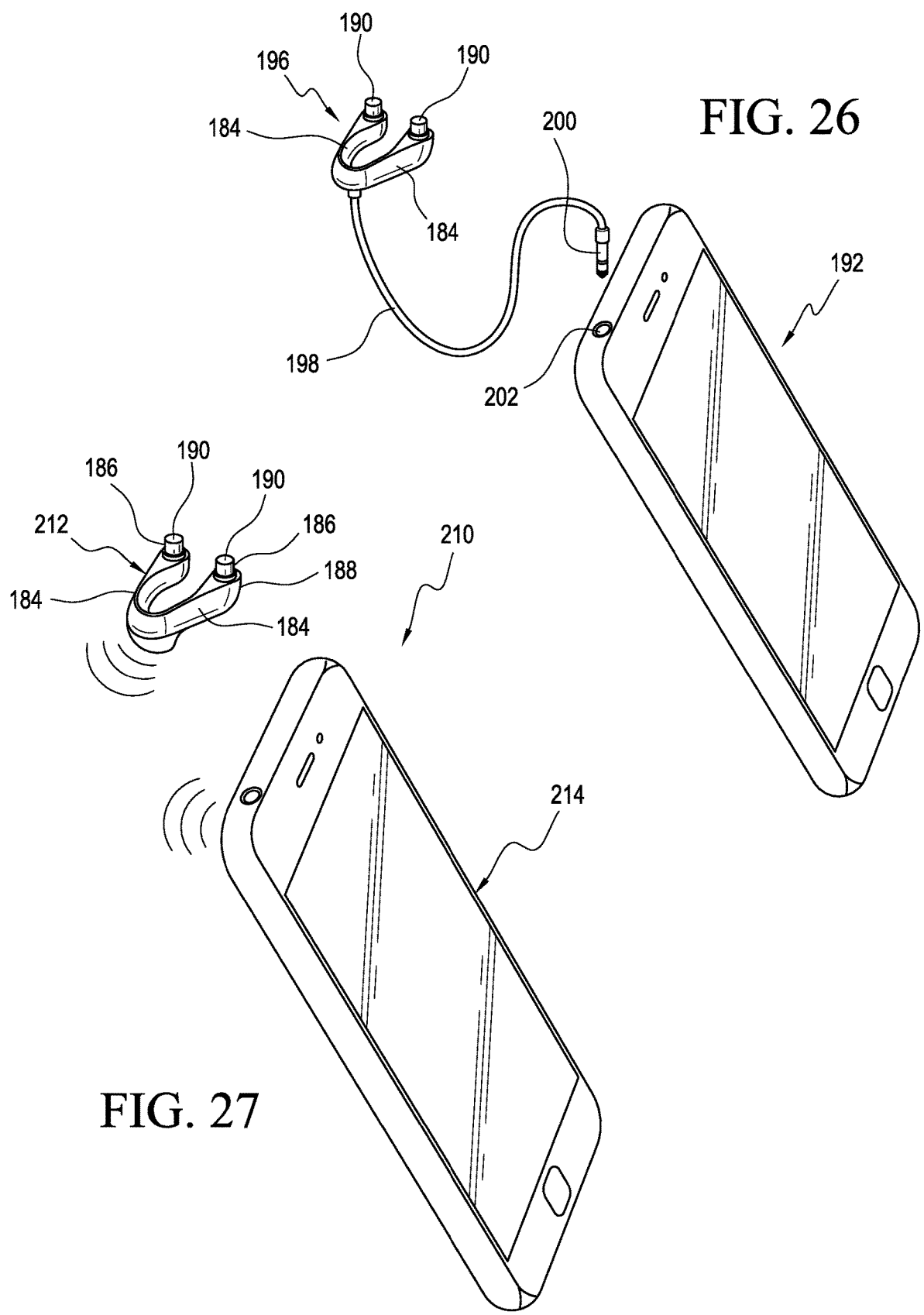

FIG. 28
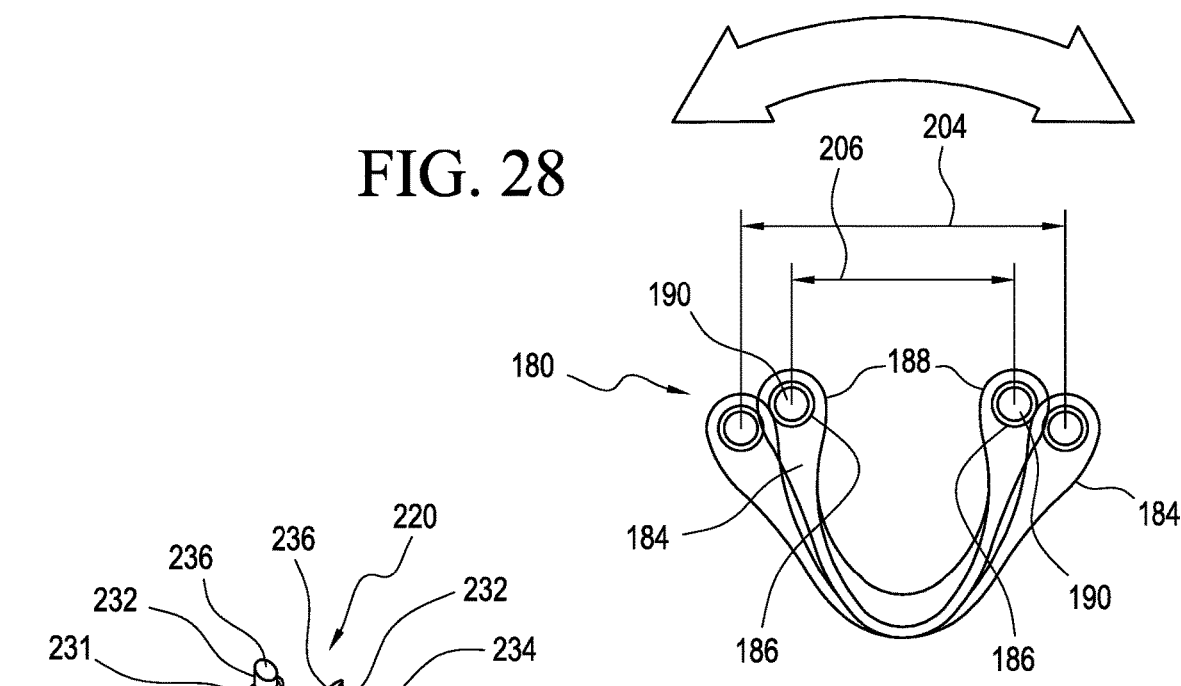
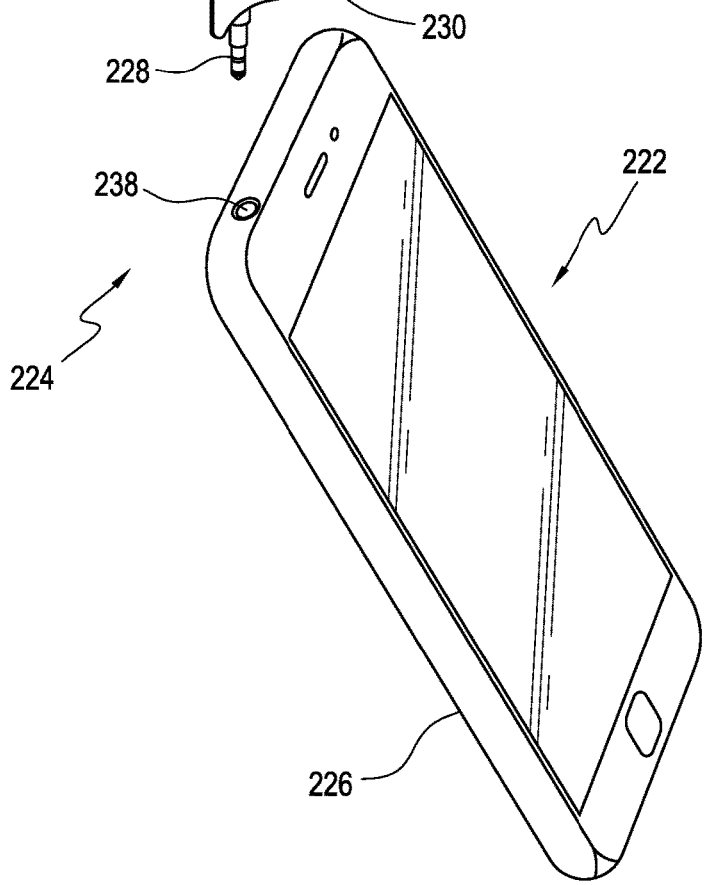
FIG. 29

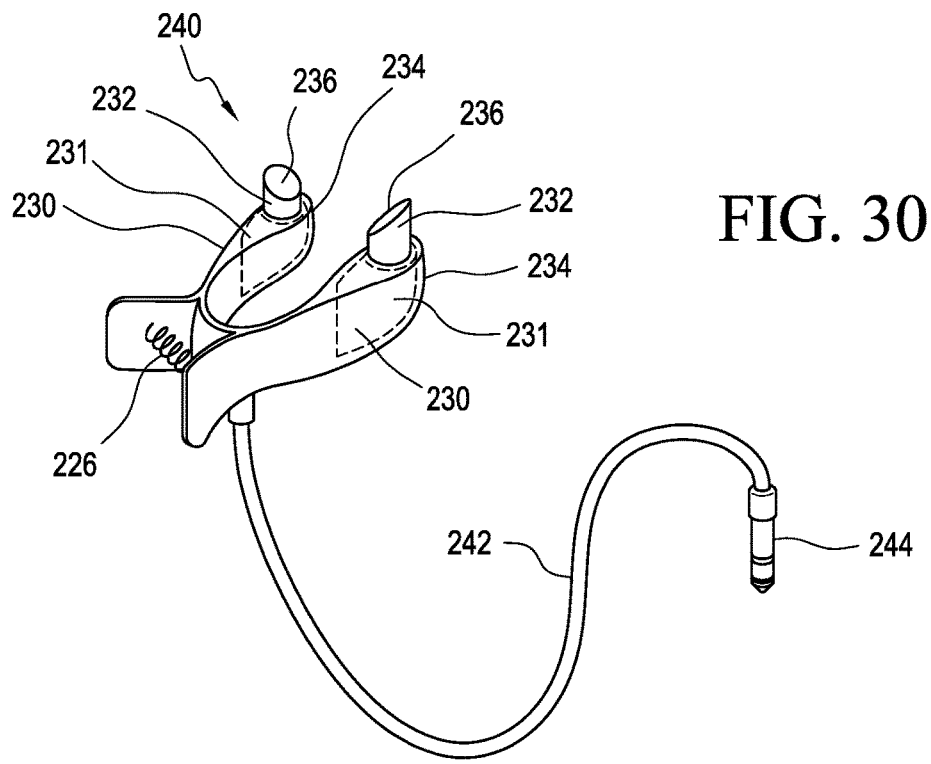
FIG. 30
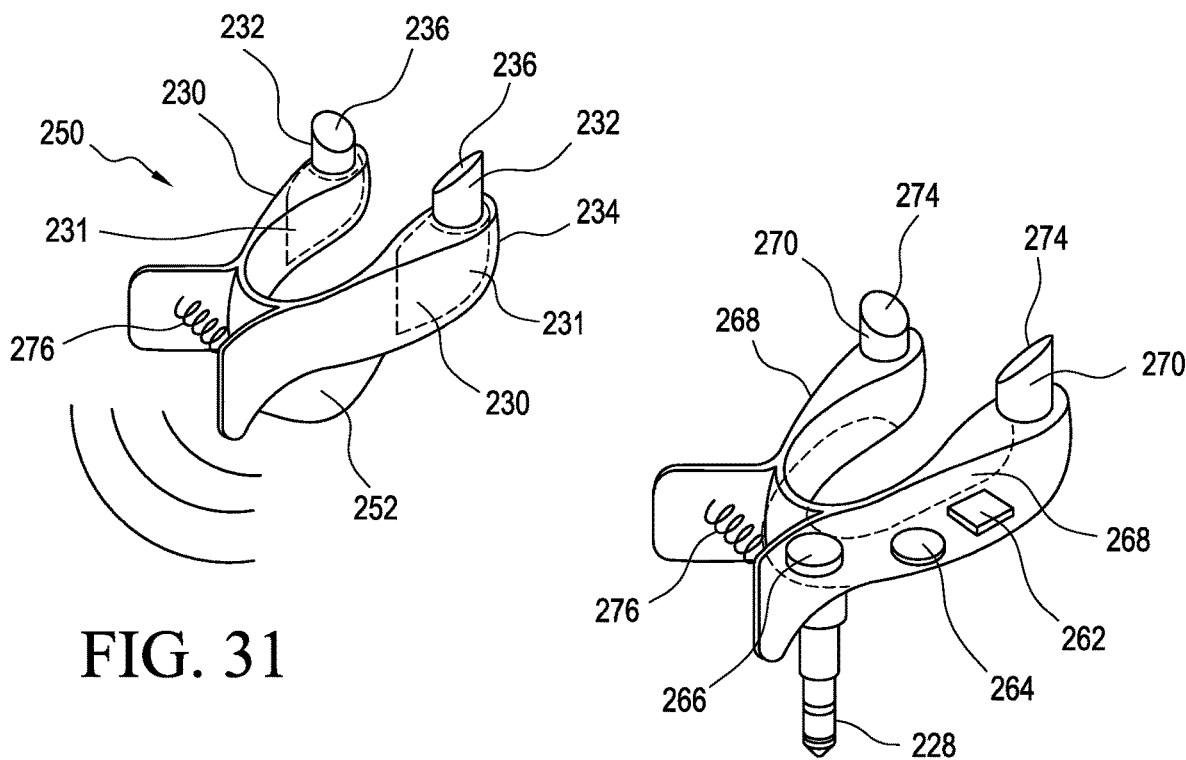
FIG. 31
FIG. 32

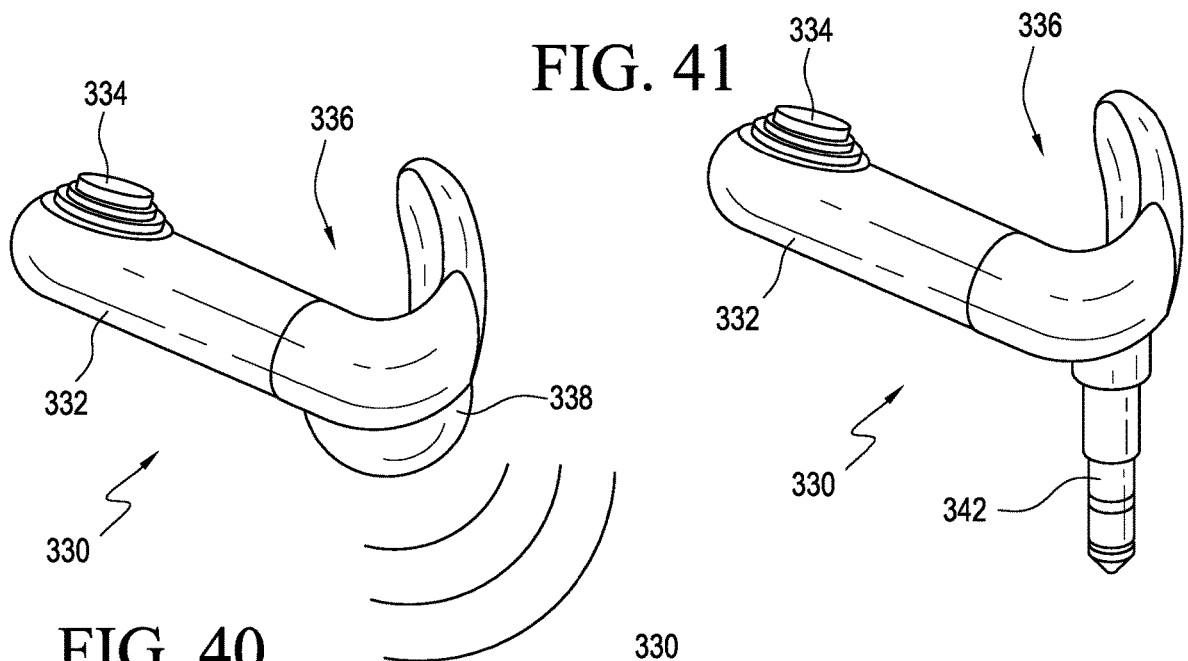
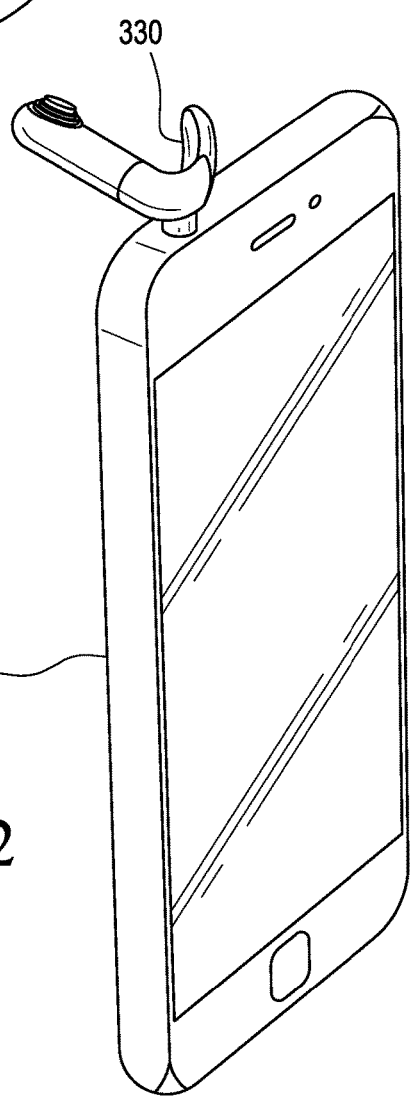
FIG. 40
FIG. 41
FIG. 42

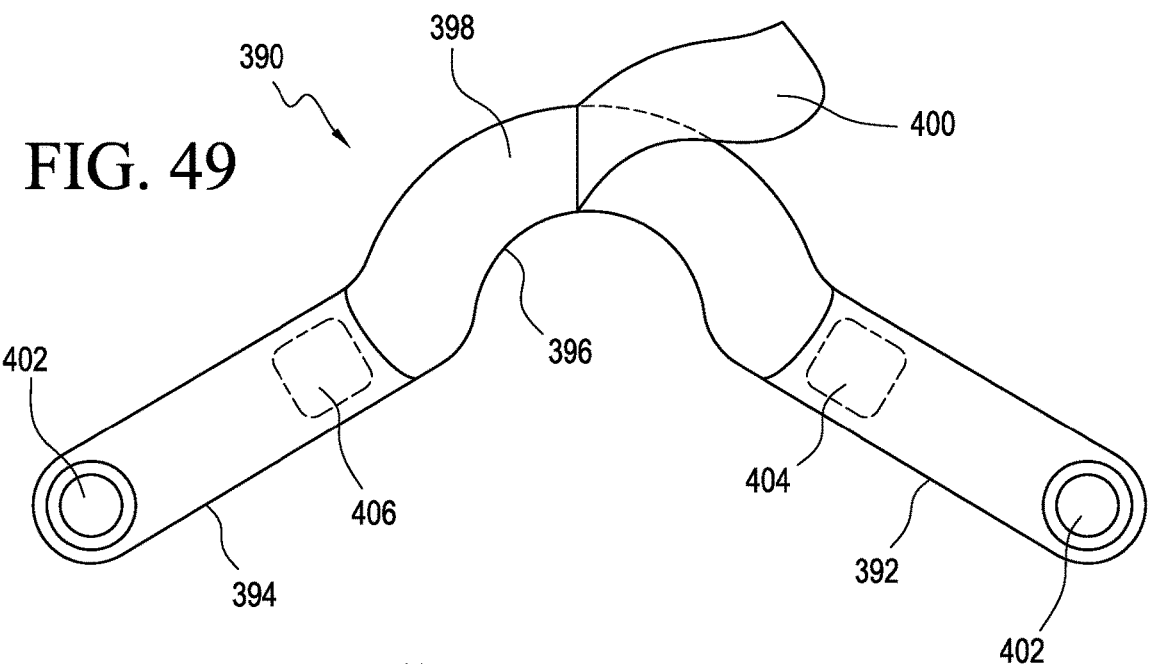
FIG. 49
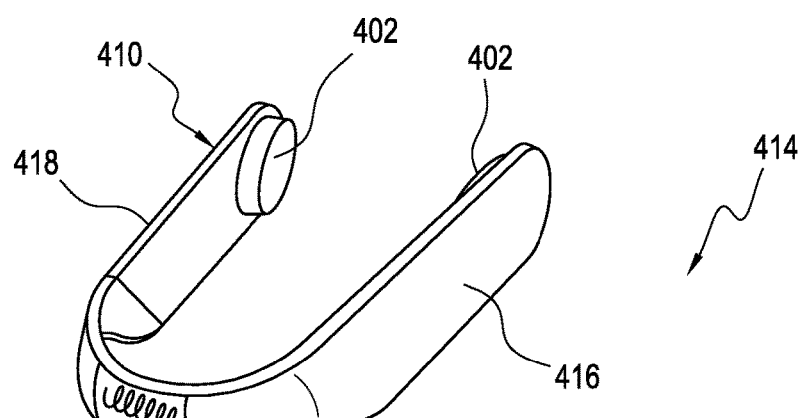
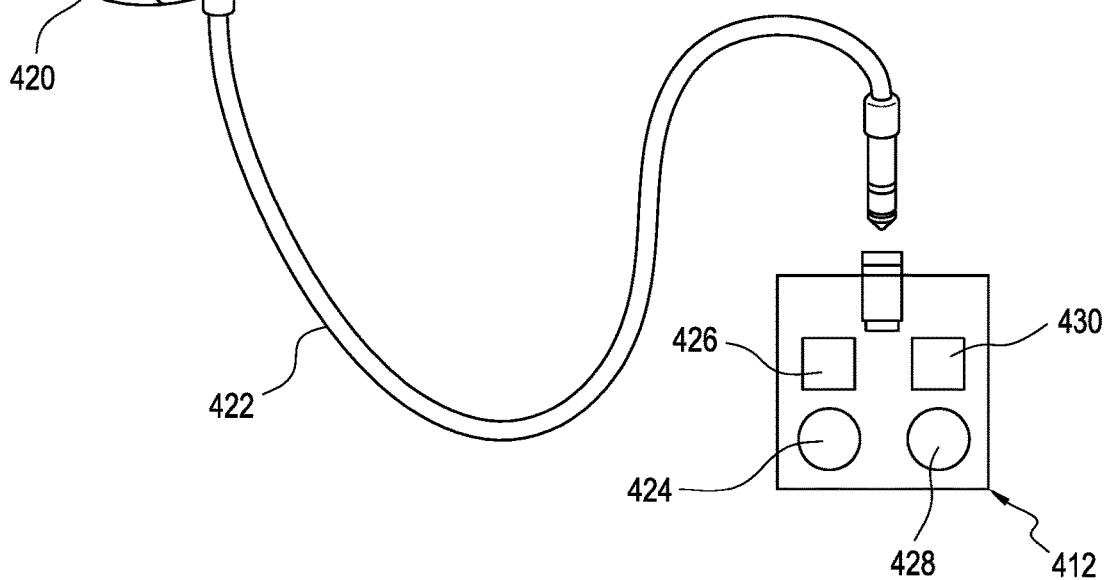
FIG. 50

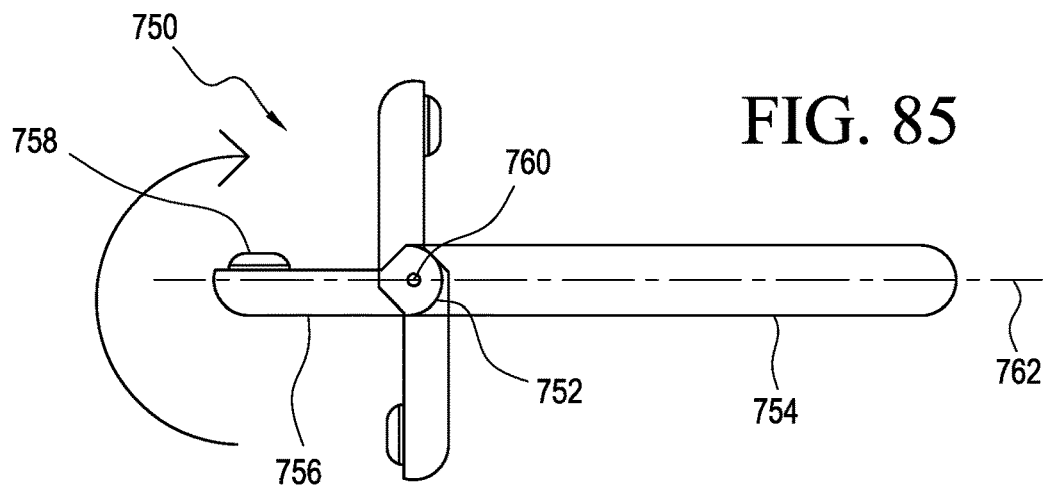
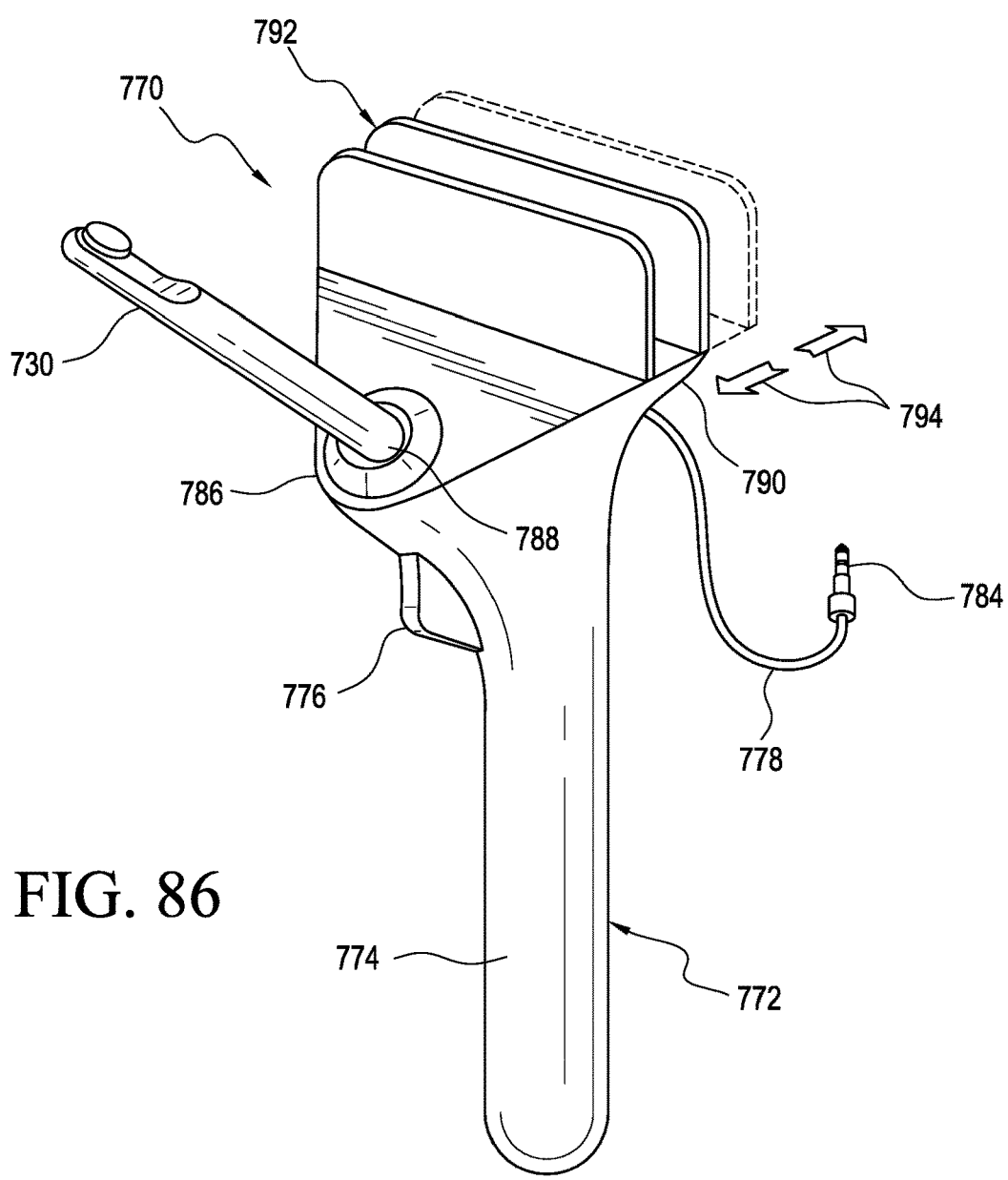

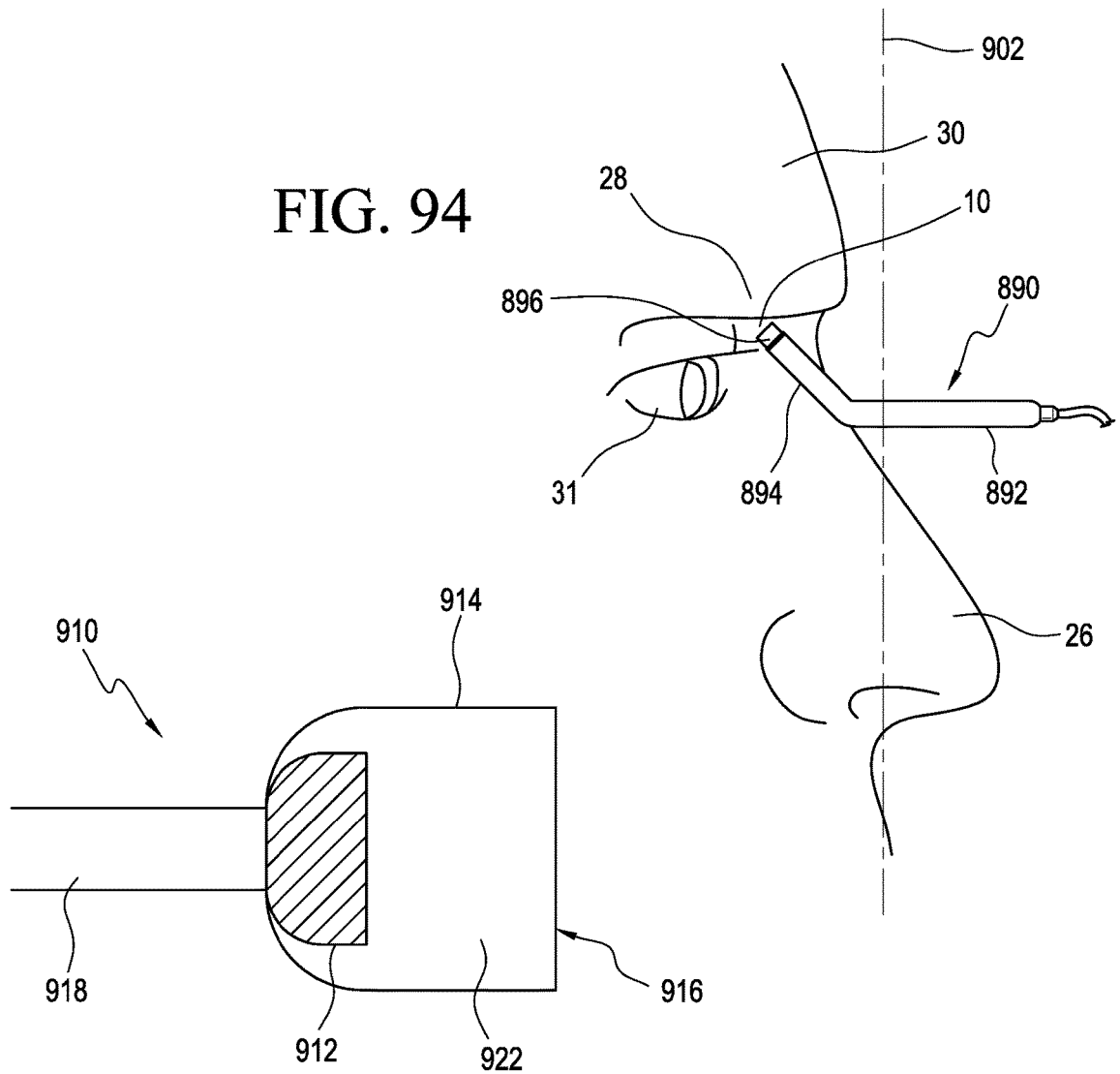
FIG. 94
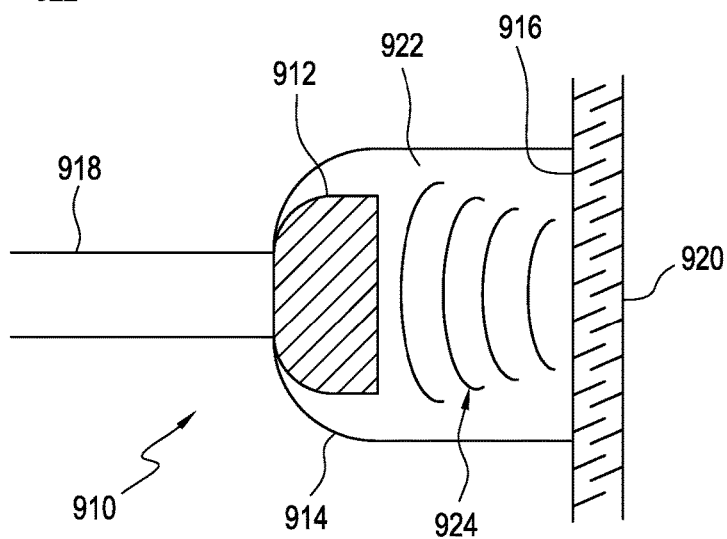
FIG. 95
FIG. 96 ing a front face, a display, and a wrist band. The display is positioned on the front face. The wrist band includes at least one sensor positioned thereon. The at least one sensor is configured to receive an emission and to transmit a signal representative of the emission to the display. The display is configured to receive the signal and to display information based on the received emission.

This disclosure also provides a sensor comprising a sensor body, a sensor connector, a sensor, and a thermometer. The sensor connector is positioned on the sensor body. The sensor is positioned on the sensor body, and the sensor is configured to receive emissions from a human body and to transmit a signal representative of the emissions to the sensor connector. The thermometer includes a temperature sensor, a display, and a thermometer connector. The thermometer connector is configured to mate with the sensor connector and to receive the signal and present the signal as a value on the display.

This disclosure also provides a sensor device, comprising a sensor body, a sensor connector, a sensor, and a plurality of devices. The sensor connector is positioned on the sensor body. The sensor is positioned on the sensor body, and the sensor is configured to receive emissions from a human body and to transmit a signal representative of the emissions to the sensor connector. Each of the plurality of devices includes a display and a device connector configured to mate with the sensor connector. Each of the plurality of devices is configured to receive the signal and to present the signal as a value on the display. At least one of the plurality of devices is a specialized thermometer that includes an integral temperature sensor.

Advantages and features of the embodiments of this disclosure will become more apparent from the following detailed description of exemplary embodiments when viewed in conjunction with the accompanying drawings.

APPARATUS FOR MEASURING A PARAMETER OF A HUMAN BODY AT AN ABREU BRAIN THERMAL TUNNEL (ABTT)

CROSS-REFERENCE TO RELATED APPLICATIONS

This application claims the benefit of priority to U.S. Provisional Patent Application No. 62/131,056, filed on Mar. 10, 2015, which is hereby incorporated by reference in its entirety.

TECHNICAL FIELD

This disclosure relates to devices configured to measure parameters available at a terminus of an Abreu brain thermal tunnel (ABTT).

BACKGROUND

Devices are available to measure various parameters of living beings. Such devices include thermometers, a glucose sensor, a chemical sensor, an oxygen sensor, a pulse sensor, an oximetry sensor, a blood pressure sensor, an optical sensor, and a fluorescent sensor.

SUMMARY

This disclosure provides a sensor device comprising a cell phone and at least one sensor. The cell phone includes a display. The at least one sensor is positioned on the cell phone and is configured to receive emissions from a human body. The at least once sensor is also configured to transmit a signal to the cell phone representative of the emissions. The cell phone is configured to receive the signal and to display information representing the signal.

This disclosure also provides a sensor device comprising a cell phone and a separable sensor device. The cell phone includes a front face and a back face positioned a spaced distance apart and a display. The separable sensor device includes a device body, a sensor positioned on a first end of the device body, and a pair of grasping arms positioned at a second end of the device body. The grasping arms are movable to grasp the front face and the back face to support the separable sensor device on the cell phone.

This disclosure also provides a separable sensor case for an electronic apparatus, comprising a case body, an electrical connector, a sensor arm, and a sensor. The case body is configured to receive the electronic apparatus. The electrical connector is positioned on the case body and is configured to connect to a connector of the electronic apparatus. The sensor arm is rotatably positioned on the case body. The sensor is positioned on a distal end of the sensor arm and is configured to receive an emitted signal and to transmit an electrical signal representing the emitted signal to the electrical connector.

This disclosure also provides a sensorial watch comprising a front face, a display, and at least one sensor. The display is positioned on the front face. The at least one sensor is positioned on the front face and is configured to receive an emission and to transmit a signal representative of the emission to the display. The display is configured to receive the signal and to display information based on the received emission.

This disclosure also provides a sensorial watch comprising a front face, a display, and a wrist band. The display is positioned on the front face. The wrist band includes at least

BRIEF DESCRIPTION OF THE DRAWINGS

FIG. 1 shows a simplified view of the ABTT and facial veins associated with the ABTT.

FIG. 2 shows a simplified partial cross-sectional view through a human skull in a vertical direction, showing the Abreu brain thermal tunnel and certain other facial features.

FIG. 4 shows a view of an electronic apparatus configured with a measurement device in accordance with an exemplary embodiment of the present disclosure.

FIG. 5 shows a side view of the electronic apparatus of FIG. 4.

FIG. 6 shows an end view of the electronic apparatus of FIG. 4.

FIG. 13 shows a perspective view the electronic apparatus of FIG. 11 with a nose piece positioned around a sensor in accordance with an exemplary embodiment of the present disclosure.

FIG. 14 shows a perspective view the electronic apparatus of FIG. 12 with a nose piece positioned around a sensor in accordance with an exemplary embodiment of the present disclosure.

FIG. 20 shows a perspective view of an electronic apparatus configured with a measurement device in accordance with a further exemplary embodiment of the present disclosure.

FIG. 21 shows a view of an end of the electronic apparatus of FIG. 20.

FIG. 26 shows a perspective view of a separable sensor device and an electronic apparatus in accordance with yet another exemplary embodiment of the present disclosure.

FIG. 27 shows a perspective view of a sensor system in accordance with a further exemplary embodiment of the present disclosure.

FIG. 28 shows a view of the separable sensor device of FIG. 24.

FIG. 29 shows a view of a temperature modification device and an electronic apparatus in accordance with an exemplary embodiment of the present disclosure.

FIG. 30 shows a view of a temperature modification device in accordance with another exemplary embodiment of the present disclosure.

FIG. 31 shows a view of a temperature modification device in accordance with yet another exemplary embodiment of the present disclosure.

FIG. 32 shows a view of a temperature modification device in accordance with still yet another exemplary embodiment of the present disclosure.

FIG. 40 shows a view of a separable sensor device in accordance with an exemplary embodiment of the present disclosure.

FIG. 41 shows a view of another separable sensor device in accordance with an exemplary embodiment of the present disclosure.

FIG. 42 shows a perspective view of an electronic apparatus with the separable sensor device of FIG. 41 positioned thereon in accordance with an exemplary embodiment of the present disclosure.

FIG. 49 shows a view of yet another separable sensor device in accordance with an exemplary embodiment of the present disclosure.

FIG. 50 shows a perspective view of a further separable sensor device and an electronic apparatus in accordance with an exemplary embodiment of the present disclosure.

FIG. 85 shows a view of a rotating mechanism of a sensor device in accordance with an exemplary embodiment of the present disclosure.

FIG. 86 shows a view of a support structure in accordance with an exemplary embodiment of the present disclosure.

FIG. 94 shows another view of the thermometer of FIG. 93.

FIG. 95 shows a sensor head in accordance with an exemplary embodiment of the present disclosure.

FIG. 96 shows another view of the sensor head of FIG. 95.

DETAILED DESCRIPTION

Figure 3:
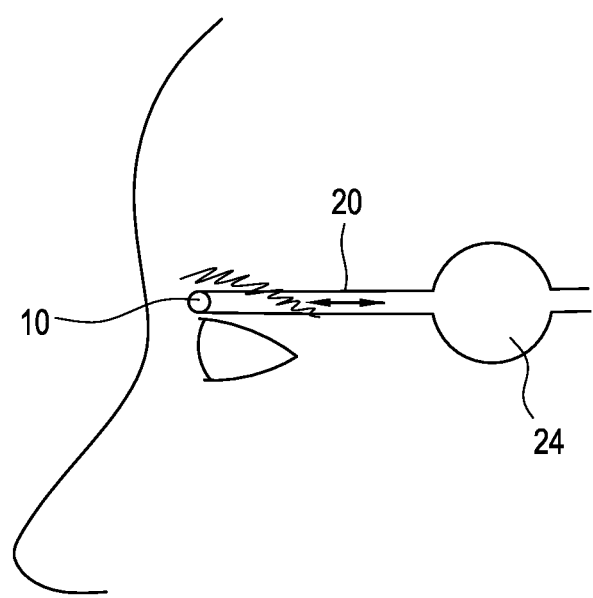
FIG. 3 shows a view of a stylized representation of the flow of blood into a brain core.
Figure 7:
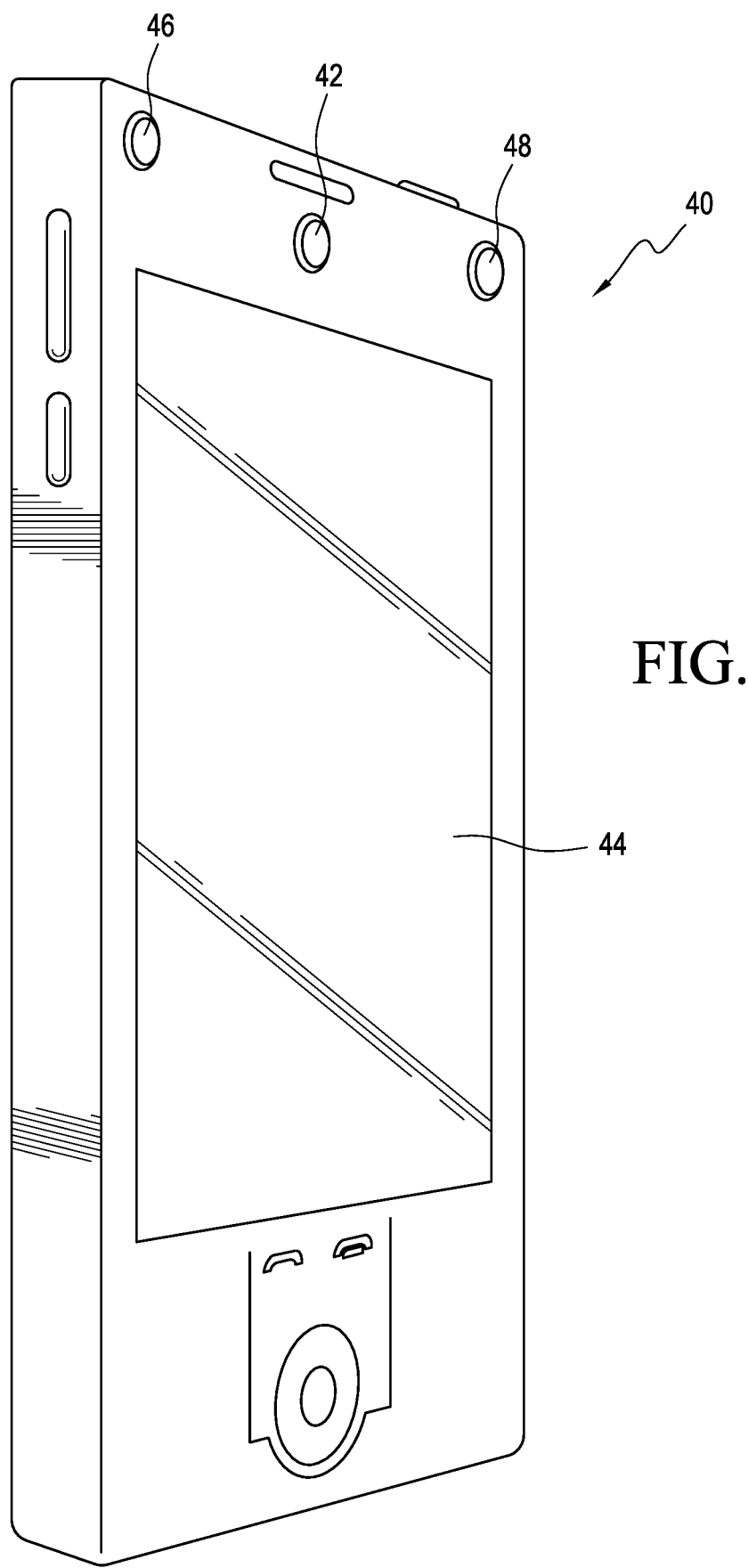
FIG. 7 shows a perspective view of the electronic apparatus of FIG. 4.

The present disclosure arises from the discovery that an Abreu brain thermal tunnel or ABTT provides the first known structure for brain-surface thermodynamic communication and thermal connection directly with the center of the brain. Anatomically and physiologically speaking, and as shown in FIGS. 1-4, ABTT 12 includes a continuous, direct, and undisturbed connection between a brain core 24 at the control center of the brain and the skin of an ABTT terminus 10. The skin of ABTT terminus 10 is unique in that it is the thinnest skin on the human body, with the fewest layers, a fat layer is absent, and has the highest thermal conductivity of any skin on the human body.

The physical and physiological events at one end of the tunnel are reproduced at the opposite end. ABTT 12 enables the direct transfer of outputs from brain core 24 to ABTT terminus 10 without significant barriers, as described in co-pending U.S. patent application Ser. No. 14/512,421, filed on Oct. 11, 2014, incorporated by reference herein in its entirety. Accordingly, the present disclosure describes apparatuses, systems, devices, mechanisms, and methods that use ABTT terminus 10 and ABTT 12 to measure the parameters of brain core 24 and of a human body.

Anatomy shows the convergence of four veins at ABTT terminus 10: frontal 14, superior palpebral 16, supraorbital 18, and angular 20. As angular vein 20 extends further from ABTT 12, it transitions into facial vein 22. Having converged, the blood from these veins flows toward brain core 24 from ABTT terminus 10 between an eye 31 and the eyebrow into the center of the brain, which is the temperature center present in the hypothalamus or thermal storage area of the body, which is positioned in the cavernous sinus. From the thermal storage area, blood is distributed throughout the brain tissue and the body, and may be used to effectively and efficiently treat and/or prevent medical conditions by the transmission of medications, chemicals, and compounds to the brain.

FIGS. 1-3 show the approximate location of these veins in relation to other facial features. Angular/facial vein 20/22 runs up alongside a nose 26, superior palpebral vein 16 runs along an eyebrow 28, and frontal vein 14 and supraorbital vein 18 run through forehead 30. For the purposes of this disclosure, terminology referring to relevant facial areas or veins herein will be described as one or more of the above-referenced veins and ABTT terminus 10.

As described herein, veins 14, 16, 18, 20, and 22 converge in the superomedial orbit in the region of the upper eyelid and adjacent to the bridge of the nose, and flow directly, without inhibition, to the center of the brain. The skin in this area, as shown in the pending application by the Applicant, is the thinnest skin in the body and free of fat, and by being in direct communication with the brain, the most direct path for measurement of parameters of the brain. These vessels lack valves, which are typically an important barrier to flow and affect the accuracy of parameter measurement, such as a temperature measurement. Without valves, these blood vessels truly provide a direct, uninhibited passage for thermal messages from the hypothalamic region of the brain. The hypothalamic region of the brain is the link between the central nervous system and the endocrine system and, as such, acts as the center of control for basic bodily functions such as, for example, hunger, thirst, body temperature, fatigue, blood pressure, immune responses, circadian cycles, hormone production and secretion, and many others.

Referring to FIGS. 4-7, an electronic apparatus configured with a measurement device in accordance with an exemplary embodiment of the present disclosure is shown, indicated generally at 40. Electronic apparatus 40 may be configured as a cell phone, tablet, or other similarly sized electronic device. Electronic apparatus 40 is configured to include a camera 42, a display 44, a first sensor 46, and a second sensor 48 positioned a spaced distance from first sensor 46 to permit simultaneous acquisition of temperature from a left ABTT terminus 10 and a right ABTT terminus 10.

Electronic apparatus 40 may be configured to acquire the temperature of one or both ABTT terminuses 10 by first activating camera 42 and displaying a face, such as that shown in FIGS. 2 and 3, on display 44. In an exemplary embodiment, in addition to displaying a face, a complementary display of temperature may be displayed to enable a user to guide electronic apparatus to the location of left ABTT terminus 10 and right ABTT terminus 10. Once first sensor 46 and second sensor 48 are positioned to measure the temperature of left ABTT terminus 10 and right ABTT terminus 10, which takes seconds, electronic apparatus 40 acquires and provides the temperature of each ABTT terminus 10 on display 44, rapidly, accurately, and precisely providing a non-contact measurement of the temperature of brain core 24. All functions of electronic apparatus 40 may be activated through display 44, which may be configured as an interactive touch screen, or through one or more physical buttons, switches, or other controls located on electronic apparatus 40. It should be understood that sensors 46 and 48 may be configured as thermopiles, infrared sensors, or other suitable sensors configured to measure body parameters without direct contact, though either sensor 46 or sensor 48 may be placed into direct contact with one ABTT terminus 10 at a time.

Figure 8:
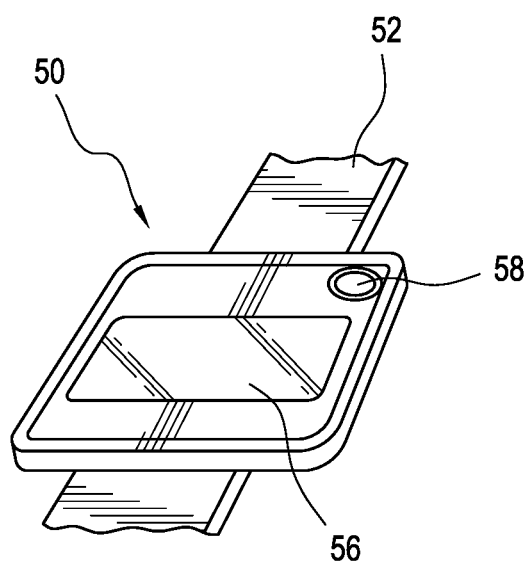
FIG. 8 shows a plan view of another electronic apparatus configured with a measurement device in accordance with an exemplary embodiment of the present disclosure.
Figure 9:
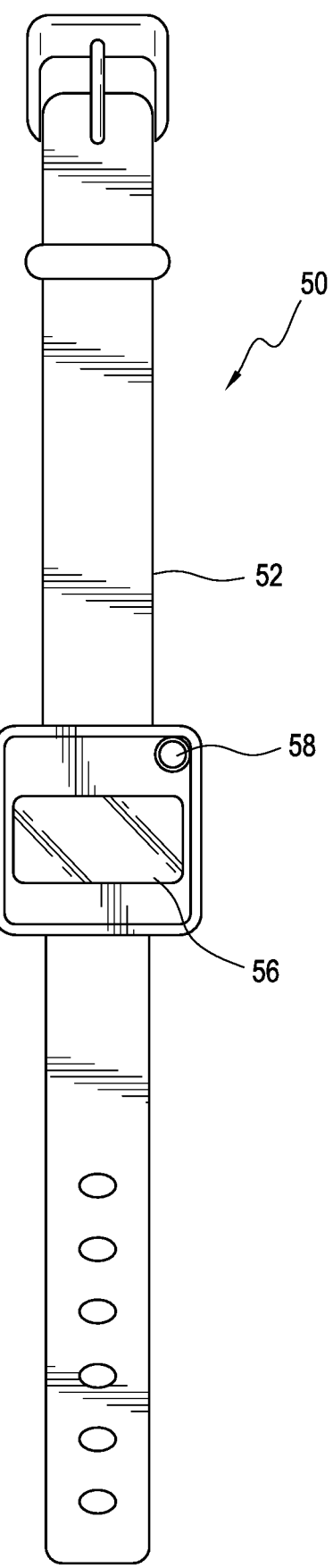
FIG. 9 shows a perspective view of the device of FIG. 8.

Referring to FIGS. 8 and 9, another electronic apparatus configured with a temperature measurement device in accordance with an exemplary embodiment of the present disclosure is shown and indicated generally at 50. Electronic apparatus 50 is configured as a wrist-mounted device, e.g., a wrist watch, including a strap 52, and an apparatus body 54. Electronic apparatus 50 further includes a display 56 and a sensor 58, which can be similar in function and construction to first sensor 46 and second sensor 48. A user of electronic apparatus 50 can acquire the temperature at ABTT terminus 10 by pressing one or more controls (not shown), or using display 56, which can be configured as a touch screen, as an input to electronic apparatus 50, and then holding their wrist in a location that places sensor 58 near ABTT terminus 10. Electronic apparatus 50 may be configured with a first audible output to indicate that ABTT terminus 10 has been located, which may be accomplished by receiving a temperature in a predetermined range, or by mapping the temperature in the region around ABTT terminus 10. Such mapping can be accomplished by, for example, a scanning type of motion of electronic apparatus 50 so that sensor 58 can find the peak temperature at ABTT terminus 10, or, in those rare circumstances where the temperature at ABTT terminus 10 is lower than the temperature of surrounding skin, which can occur in very hot ambient conditions, the minimum temperature at ABTT terminus 10. Such scanning in described in more detail in co-pending U.S. patent application Ser. No. 14/593,848, incorporated herein by reference in its entirety. Once ABTT terminus 10 has been located, a second audible output, which can be different from the first audible output, can indicate that temperature at ABTT terminus 10 has been measured. Once the temperature of ABTT terminus 10 has been measured, a user will move display 56 to a location where it can be viewed, seeing a displayed temperature, or an audible output can present the temperature of ABTT terminus 10.

Figure 10:
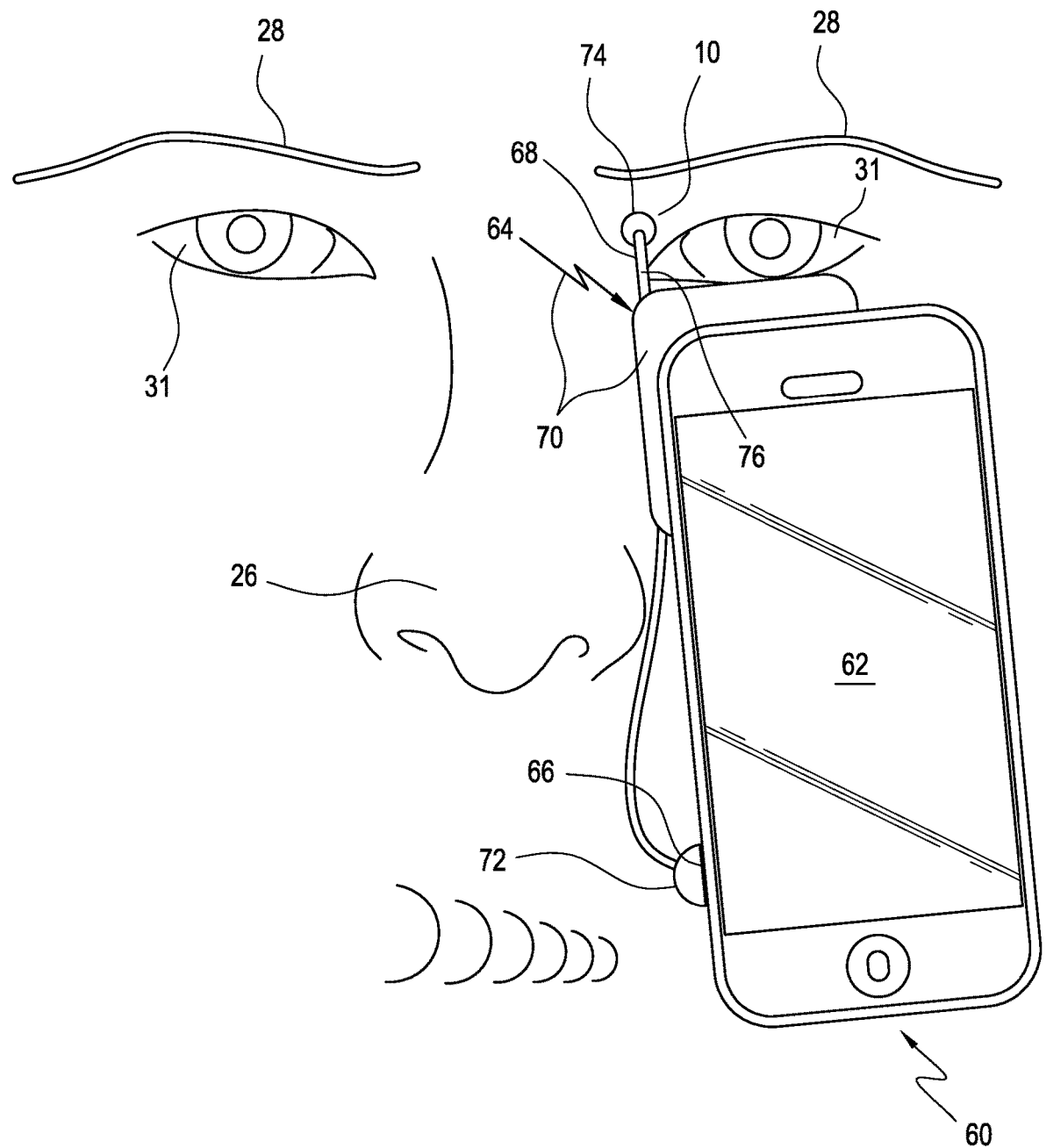
FIG. 10 shows a view of yet another electronic apparatus configured with a measurement device in accordance with an exemplary embodiment of the present disclosure.

FIG. 10 is a view of yet another electronic apparatus configured with a temperature measurement device in accordance with an exemplary embodiment of the present disclosure, indicated generally at 60. Electronic apparatus 60 is configured to include a display 62, a temperature sensing device 64, and an electrical connector 66. Temperature sensing device 64 is configured to attach to electronic apparatus 60, and to interface with connector 66. Temperature sensing device 64 is configured to include a probe 68, a sensor body 70 configured to attach to a housing 70 of electronic apparatus 60, and an electrical sensor connector 72 configured to mate with connector 66. Probe 68 is configured to include a sensor 74 located at a distal end of a sensor arm 76. Sensing device 64 is configured as a plug-in device, which can be by way of sensor connector 72.

Sensor 74 may be positioned to be in contact with ABTT terminus 10. To find ABTT terminus 10, the area of ABTT terminus 10 may be scanned by sensor 74, with electronic apparatus 60 providing an audible, visual, such as on display 62 or a flashing light, or vibratory, also described as tactile feedback, output. A first indication from electronic apparatus 60 can be indicative of locating ABTT terminus 10, and a second indication from electronic apparatus 60 can be indicative of a temperature measurement of ABTT terminus 10. Electronic apparatus 60 can be configured to transmit temperature data wirelessly or by wire to other electronic devices.

Figure 11:
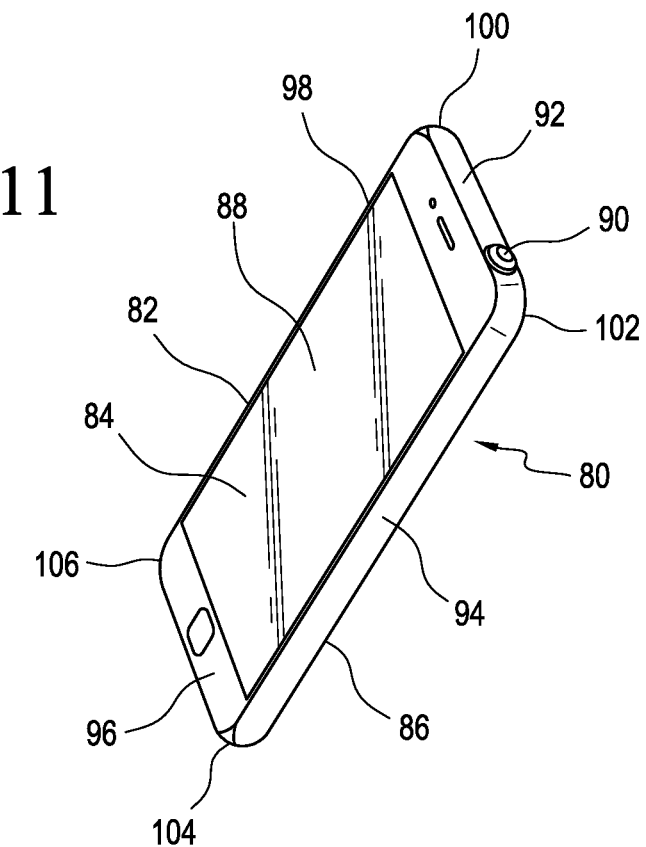
FIG. 11 shows a perspective view of a further electronic apparatus configured with a measurement device in accordance with an exemplary embodiment of the present disclosure.

Referring to FIG. 11, another electronic apparatus configured with a temperature measurement device in accordance with an exemplary embodiment of the present disclosure is shown and indicated generally at 80. Electronic apparatus 80 can be configured as a cell phone (or alternatively a tablet, a computer device, and the like) and includes an apparatus body 82 including a front face 84, a back face 86, a display 88, and a temperature sensor 90. Apparatus body 82 further includes a top side face 92, a right side face 94, a bottom side face 96, and a left side face 98, in addition to a left top corner 100, a right top corner 102, a right bottom corner 104, and a left bottom corner 106. Temperature sensor 90 can be similar in function and construction to first sensor 46 and second sensor 48.

Considering that the ABTT is located in a rather confined and hidden area at a junction of the nose with eyebrow, and in an orbital roof area, the position of temperature sensor 90 in apparatus body 82 is configured to mate with this area in a specific and defined way, otherwise measurements will be difficult and the nose may hinder proper measurement. If a sensor, for instance, is positioned in a mid-portion of apparatus body 82 exemplified as a cell phone, the orbital bone would prevent temperature sensor 90 from reaching ABTT terminus 10 at a roof of the orbit. In order to reach ABTT terminus 10, which is positioned at the roof of the orbit and in the junction of the eyebrow and nose, temperature sensor 90 in apparatus body 82 is preferably located adjacent to one of corners 100, 102, 104, or 106, temperature sensor 90 being also preferably located in one of side faces 92, 94, 96, and 98. The preferred distance from temperature sensor 90 to one of corners 100, 102, 104, or 106 is equal to or less than 30 mm, is more preferably equal to or less than 20 mm, is even more preferably equal to or less than 15 mm, is still more preferably equal to or less than 10 mm, and is most preferably equal to or less than 5 mm.

Temperature sensor 90 is preferably located adjacent to one of top corners 94 and 96, and bottom corners 98 and 100. By way of example but not of limitation, in FIG. 11 temperature sensor 90 is located on top side face 92 and adjacent, alongside, near, or close to corner 102.

Figure 12:
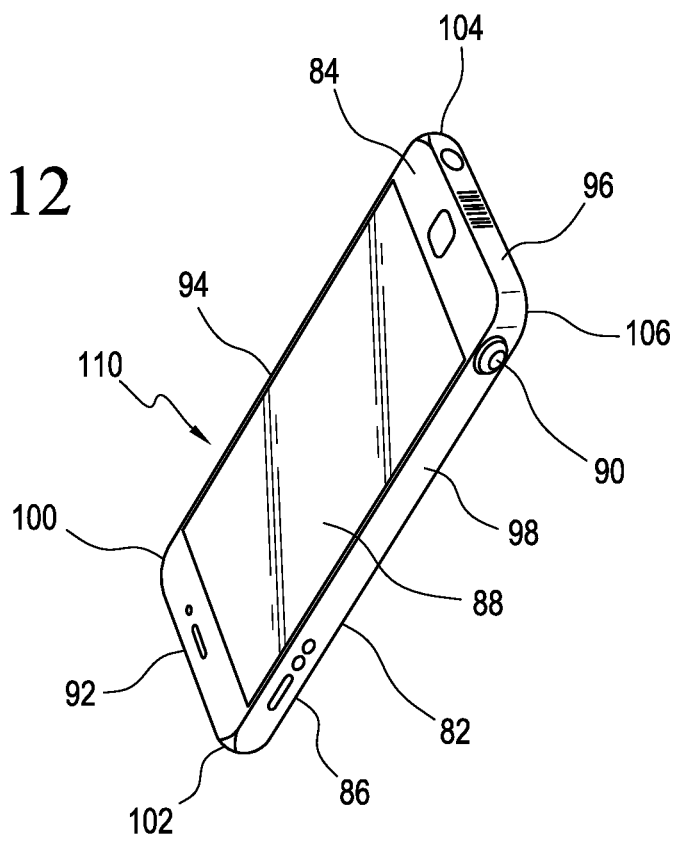
FIG. 12 shows a perspective view of a yet further electronic apparatus configured with a measurement device in accordance with an exemplary embodiment of the present disclosure.

FIG. 12 shows a perspective view of yet a further electronic apparatus, indicated generally at 110, configured with a measurement device in accordance with an exemplary embodiment of the present disclosure. While electronic apparatus 110 includes differences from electronic apparatus 80 shown in FIG. 11, the features are sufficiently similar that the same element numbers are used for the sake of brevity. In FIG. 12, temperature sensor 90 is positioned on or in left side face 98 in a location that is adjacent, near, alongside, or close to corner 106.

Electronic apparatus 80 and electronic apparatus 110 can be configured to include a nose piece 112, which can be permanently or integrally fixed or detachably connected to temperature sensor 90, to assist positioning apparatus body 82 to align temperature sensor 90 with ABTT terminus 10, as shown in FIGS. 13 and 14.

Figure 15:
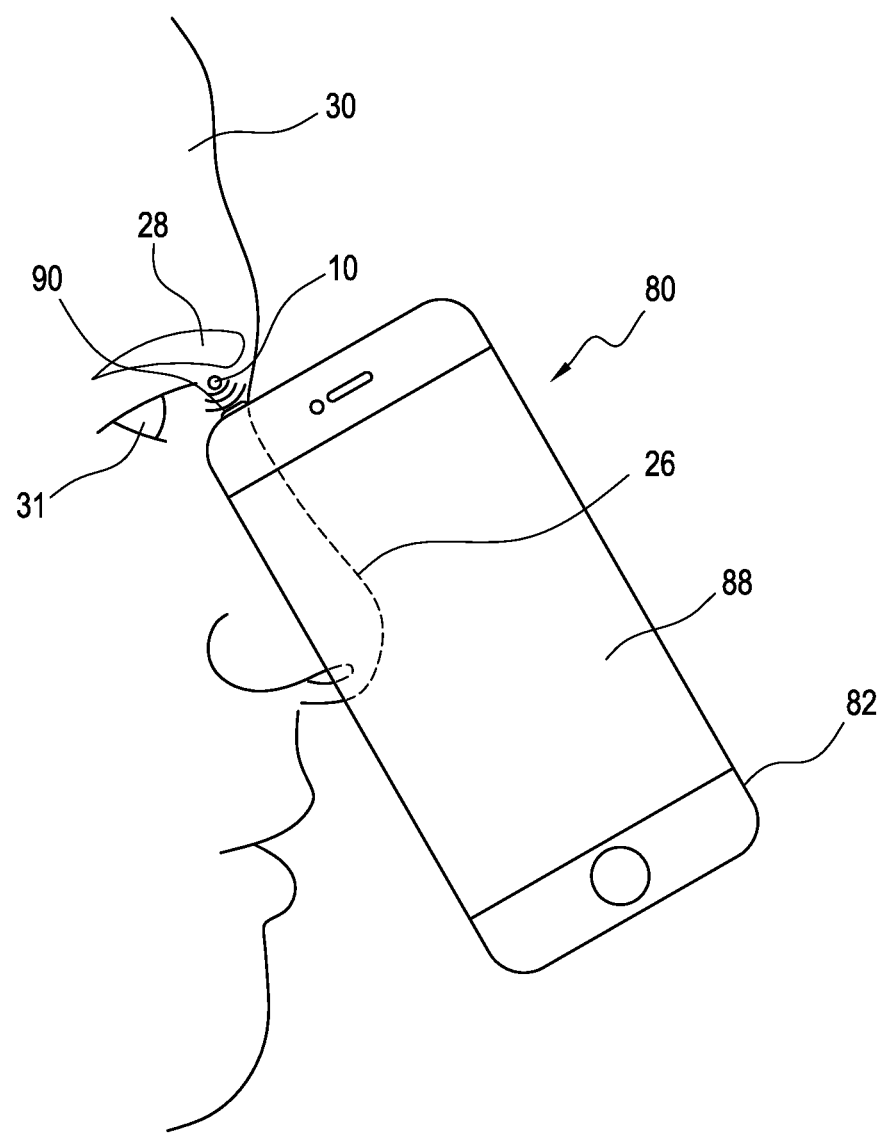
FIG. 15 shows a view of the device of FIG. 11 in use.
Figure 16:
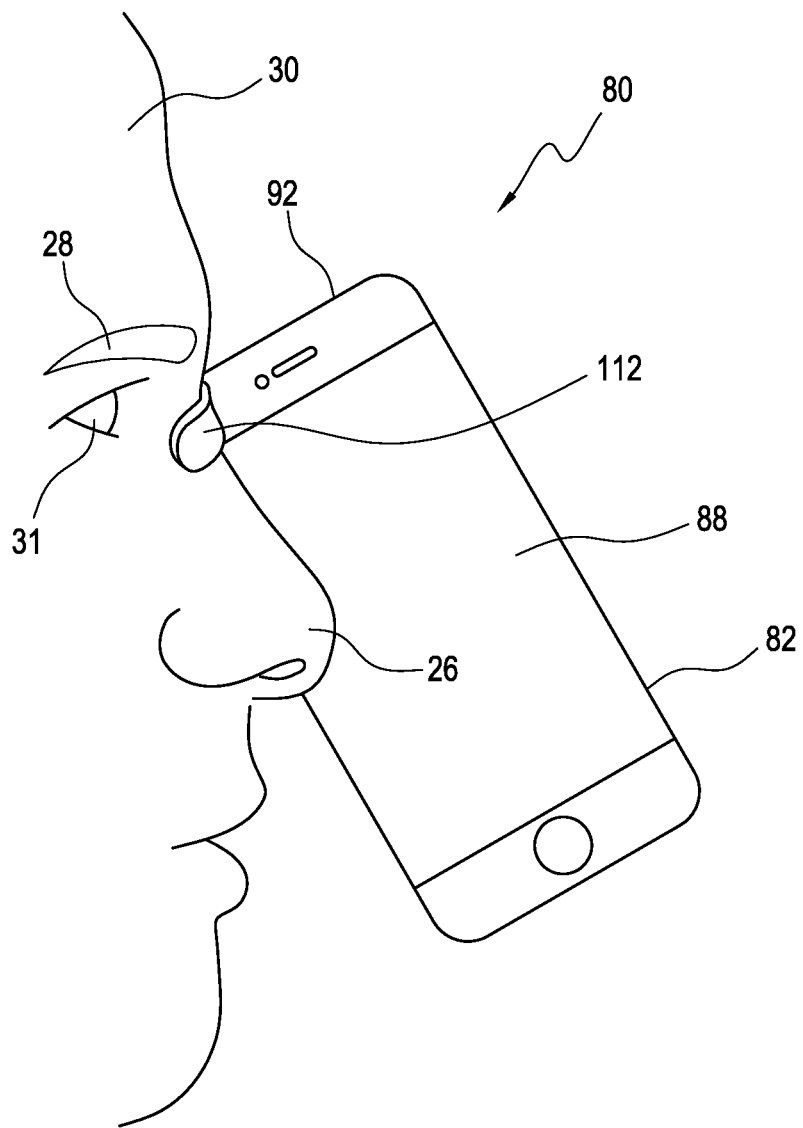
FIG. 16 shows a view of the device of FIG. 11 in use with a nose piece.

A user of electronic apparatus 80 can acquire the temperature at ABTT terminus 10 by pressing one or more controls (not shown), or using display 88, which can be configured as a touch screen, as an input to electronic apparatus 80, and then holding apparatus body 82 next to, alongside, near, or close to nose 26 with display 88 essentially parallel to nose 26, and in a location that places temperature sensor 90 near, adjacent to, alongside, close to, at, or on ABTT terminus 10, as shown in FIG. 15, with sensor 90 of FIG. 12 exemplarily showing as the measurement sensor (performing a contact or a non-contact measurement) and receiving a thermal signal from ABTT terminus 10. FIG. 16 shows electronic apparatus 80 with nose piece 112 positioned on nose 26 of the user's face for measurement.

It should be understood that although sensor 90 is primarily described as a temperature sensor, sensor 90, as well as other sensors described herein for interfacing with ABTT terminus 10, can include a variety of sensors including, and by way of example, a glucose sensor, a chemical sensor, an oxygen sensor, a pulse sensor, an oximetry sensor, blood pressure sensor, an optical sensor, a fluorescent sensor, and any sensor capable of measuring any biological variable or biological signal including the various biological signals and parameters described by Applicant in various patents and applications under the title "Apparatus and Method for Measuring Biologic Parameters," including U.S. Pat. No. 7,187,960, issued Mar. 6, 2007, U.S. Pat. No. 8,172,459, issued May 8, 2012, U.S. Pat. No. 8,328,420, issued Dec. 11, 2012, U.S. Pat. No. 8,721,562, issued May 13, 2014, U.S. Pat. No. 8,849,379, issued Sep. 30, 2014, U.S. Pat. No. 9,011,349, issued Apr. 21, 2015, U.S. Pat. No. 9,119,530, issued Sep. 1, 2015, pending U.S. patent application Ser. No. 14/500,362, filed Sep. 29, 2014, pending U.S. patent application Ser. No. 14/500,550, filed Sep. 29, 2014, pending U.S. patent application Ser. No. 14/622,284, filed Feb. 13, 2015, and pending U.S. patent application Ser. No. 14/687,106, filed Apr. 15, 2015, the contents of which are incorporated by reference in their entirety herein.

Sensor 90 can include contact and non-contact sensors and detectors, including infrared detectors. Other sensors such as proximity sensors, optical sensors, and the like can be included as part of sensor 90 and can be used alone or in combination with other sensors. Any of the sensors described in this disclosure can include the plurality of sensors mentioned herein, as a single sensor or a combination of sensors.

Figure 17:
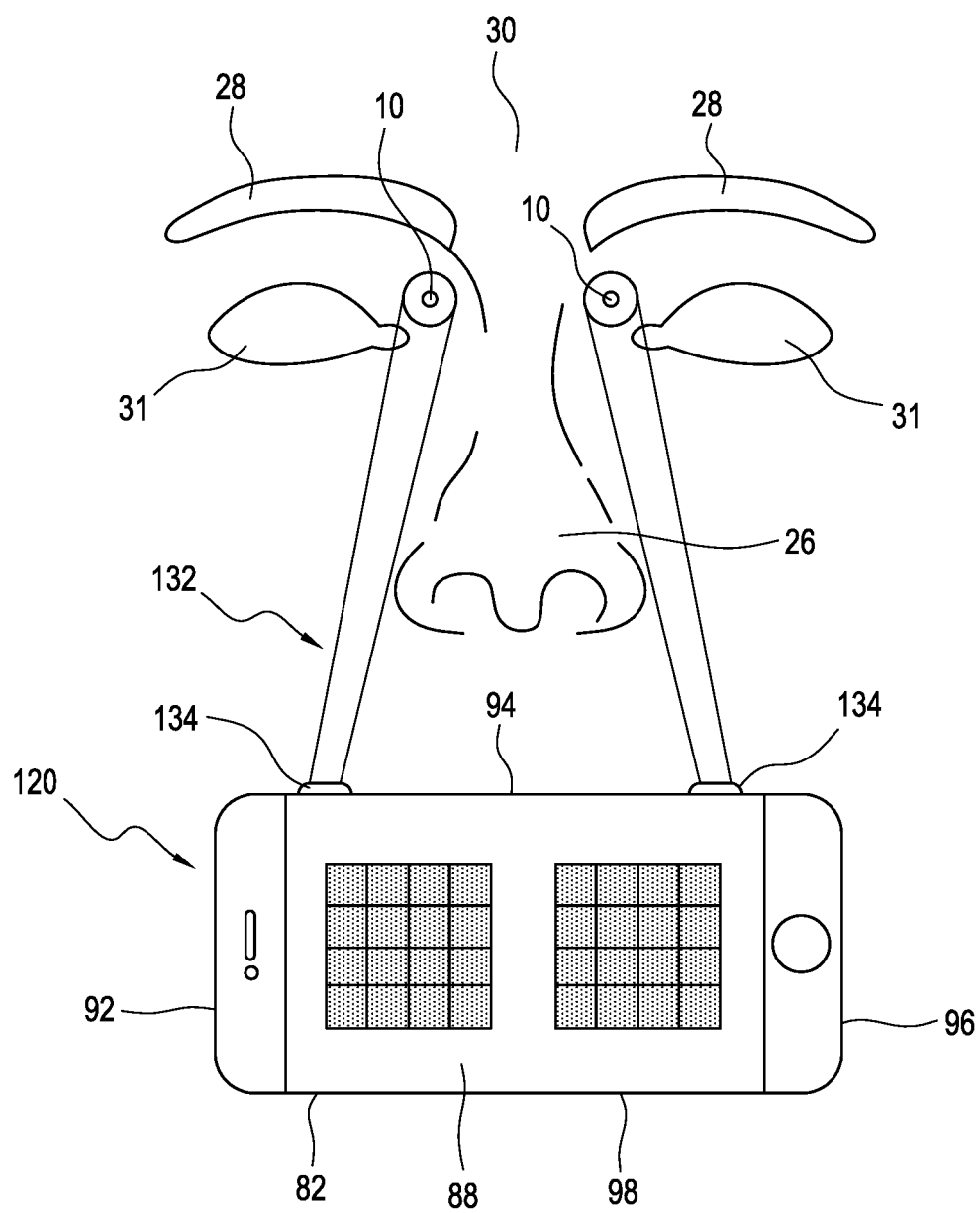
FIG. 17 shows a view of an electronic apparatus configured with a measurement device in accordance with an exemplary embodiment of the present disclosure.

FIG. 17 shows a view of an electronic apparatus, indicated generally at 130, configured with a measurement device, indicated generally at 132, in accordance with an exemplary embodiment of the present disclosure. Measurement device 132 includes a pair of sensors 134 positioned on one of side faces 92, 94, 96, or 98 of apparatus body 82. By way of example, sensors 134 can each include an array of infrared sensors configured to read infrared emission from at least one ABTT terminus 10 on the user's face. Emission from ABTT terminus 10 is captured by sensors 134, and can be displayed on display 88. The captured image can be analyzed by electronic apparatus 120 to determine a temperature of ABTT terminus 10. It should be understood that chemical measurements and measurement of analytes including glucose can be accomplished by capturing emissions from ABTT terminus 10, and the processor (not shown) located in apparatus body 82 execute operations to calculate and report concentration and amount of the chemical substances and the analytes.

Figure 18:
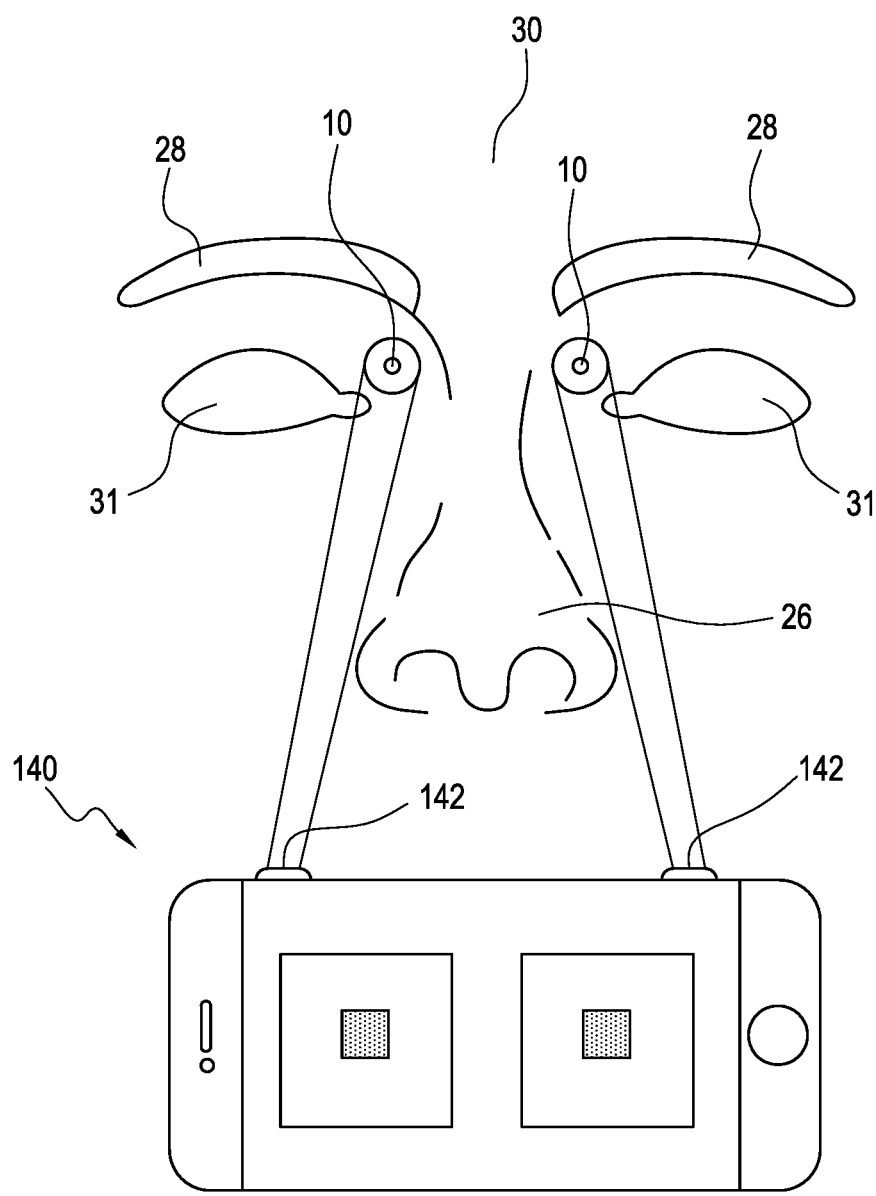
FIG. 18 shows a view of an electronic apparatus configured with a measurement device in accordance with another exemplary embodiment of the present disclosure.

FIG. 18 shows a view of an electronic apparatus, indicated generally at 140, in accordance with an exemplary embodiment of the present disclosure. Electronic apparatus 140 is similar to electronic apparatus 120 of FIG. 17, but each array 134 is replaced by a single sensor 136, meaning a single thermal sensor rather than an array of thermal sensors. It should be understood that although two sensors 142 are described, in an alternative embodiment electronic apparatus 140 includes only one sensor 140.

Figure 19:
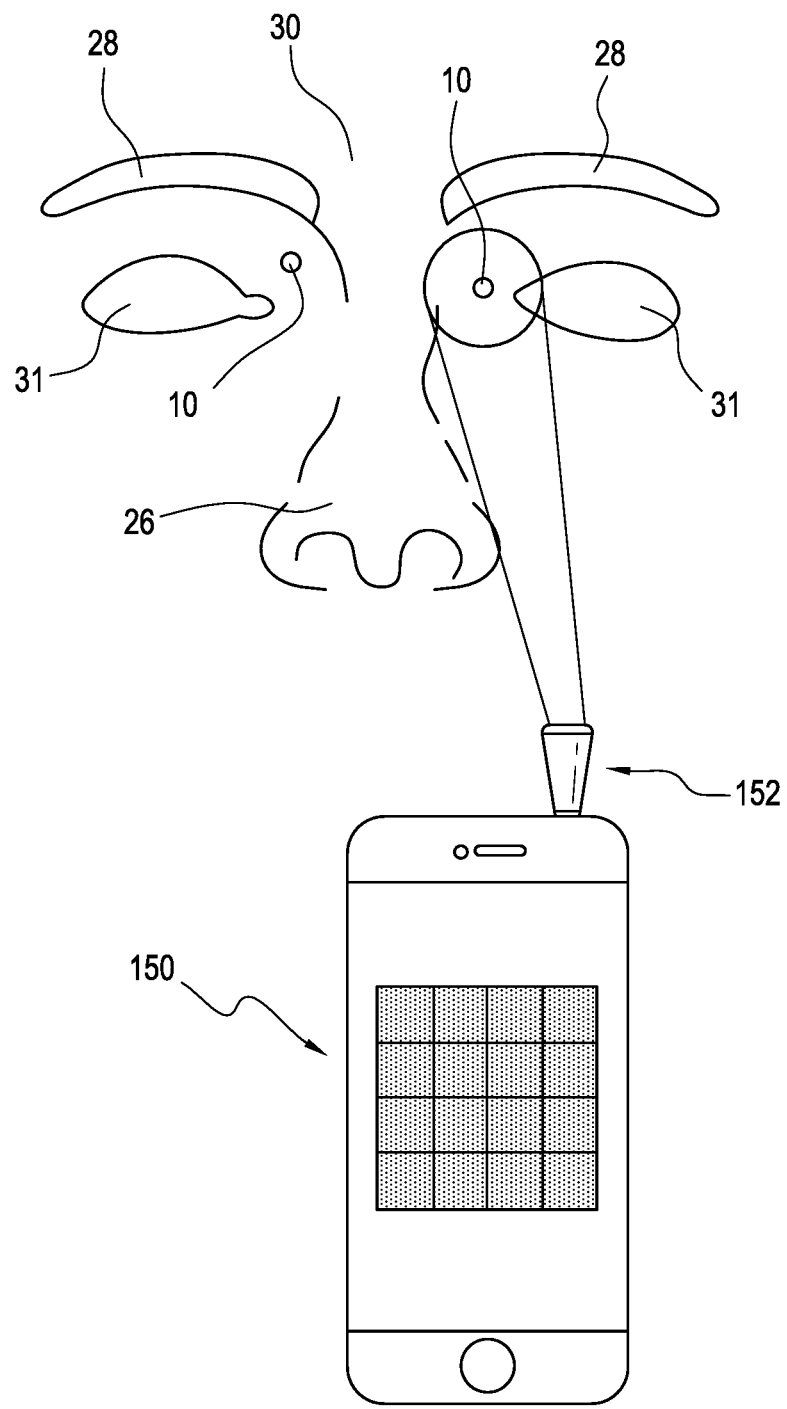
FIG. 19 shows a view of an electronic apparatus configured with a measurement device in accordance with yet another exemplary embodiment of the present disclosure.
Figure 22:
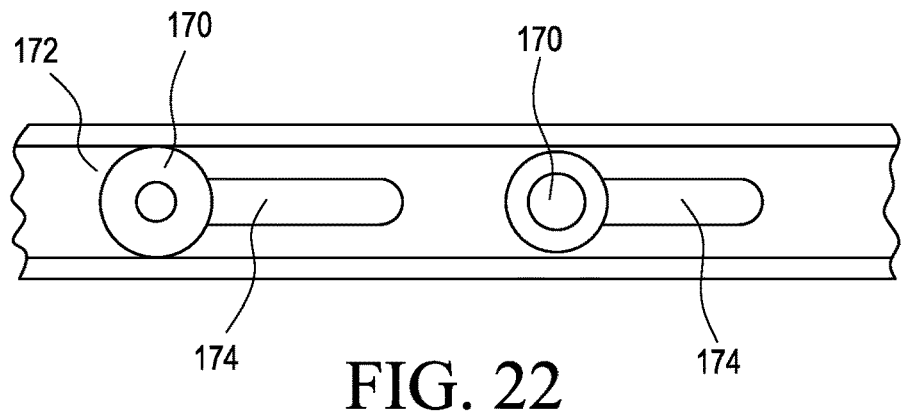
FIG. 22 shows a view of a side of the electronic apparatus of FIG. 20.
Figure 23:
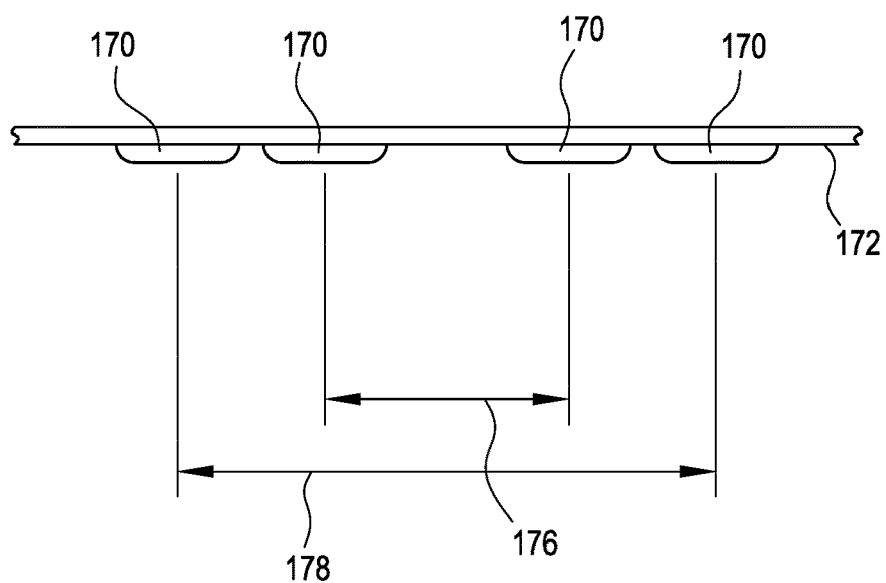
FIG. 23 shows another view of the electronic apparatus of FIG. 20 showing available positions for measurement devices of the electronic apparatus.

FIG. 19 shows a view of an electronic apparatus, indicated generally at 150, configured to include a measurement device, indicated generally at 152, in accordance with yet another exemplary embodiment of the present disclosure. Measurement device 152 includes a thermal sensor array in the exemplary embodiment of FIG. 19. Each ABTT terminus 10 can be measured by measuring a first side, such as the right side, and then measuring the second opposite side, such as the left side. Measurement device 152 is removably attached connected to the body of electronic apparatus by an electrical jack or connector, described elsewhere herein, configured to fit in a connector positioned the body of electronic apparatus 150.

Anatomy of ABTT terminus 10 is associated with anatomy and dimensions of nose 26. FIGS. 20-23 show views of an electronic apparatus, indicated generally at 160, in accordance with an exemplary embodiment of the present disclosure. Electronic apparatus 160 includes a pair of rotatable sensors 162 disposed near an end of electronic apparatus 160, each rotatable sensor 162 positionable or adjustable to a particular nose 26 for each individual of a population. Each sensor 162 is positioned on a corner, such as a top left corner 164 and/or a top right corner 166 of an apparatus body 168 of electronic apparatus 160. Each sensor 162 of the pair or the dual sensors is rotatable about a longitudinal axis of electronic apparatus 160 that extends along the longest length of electronic apparatus 160 to enable a user to align each sensor 162 with a respective ABTT terminus 10. Electronic apparatus 160 further includes a pair of sensors 170 on a side face of electronic apparatus, such as right side face 172. Each sensor 170 is individually slidable in a slot or groove 174 to modify the spacing between sensors 170, with such spacing having a minimum predetermined spacing 176 and a maximum predetermined spacing 178 to adjust the spacing of sensors 170 for alignment with respect ABTT terminuses 10. Although rotatable sensors 162 and slidable or sliding sensors 170 are shown permanently affixed to apparatus body 168, it should be understood that a removably attached sensor assembly with a rotatable or sliding mechanism are within the scope of the disclosure.

Figure 24:
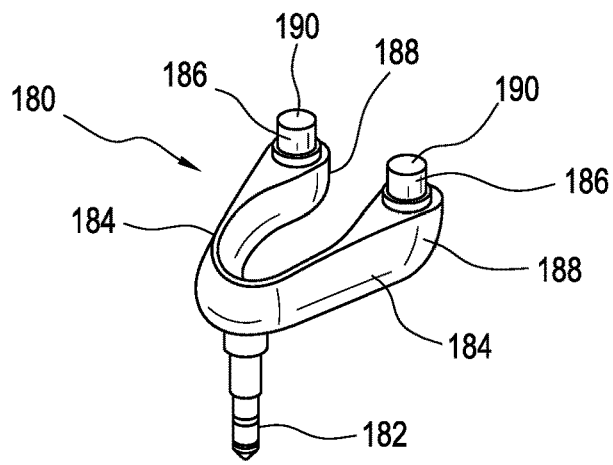
FIG. 24 shows a perspective view of a separable sensor device in accordance with an exemplary embodiment of the present disclosure.

FIGS. 24 and 28 show views of a separable sensor device, indicated generally at 180, in accordance with an exemplary embodiment of the present disclosure. It should be understood that separable sensor device 180 can also be described as a sensor assembly, as can other separable sensor devices disclosed herein. Separable sensor device 180 includes an electrical jack or connector 182 configured to connect to a mating electrical connector positioned in an electronic apparatus. Separable sensor device 180 includes two flexible arms 184, which can be approximately parallel in the relaxed condition shown in FIG. 24, and can be moved away from each other in as shown in FIG. 28 to configure a first spaced distance 204 between sensors 186 up to a second spaced distance 206 between sensors 186. First spaced distance 204 and second spaced distance 206 permit a range of adaptability for the nose and facial anatomy, e.g., nose widths, of individuals. Each flexible arm extends in a longitudinal direction and includes a sensor 186 at a terminus or distal end 188, each sensor 186 with an axis that is disposed essentially perpendicular to the longitudinal direction of arm 184 and having a measuring surface 190. Measuring surface 190 is configured to measure an emitted signal of ABTT terminus 10.

Figure 25:
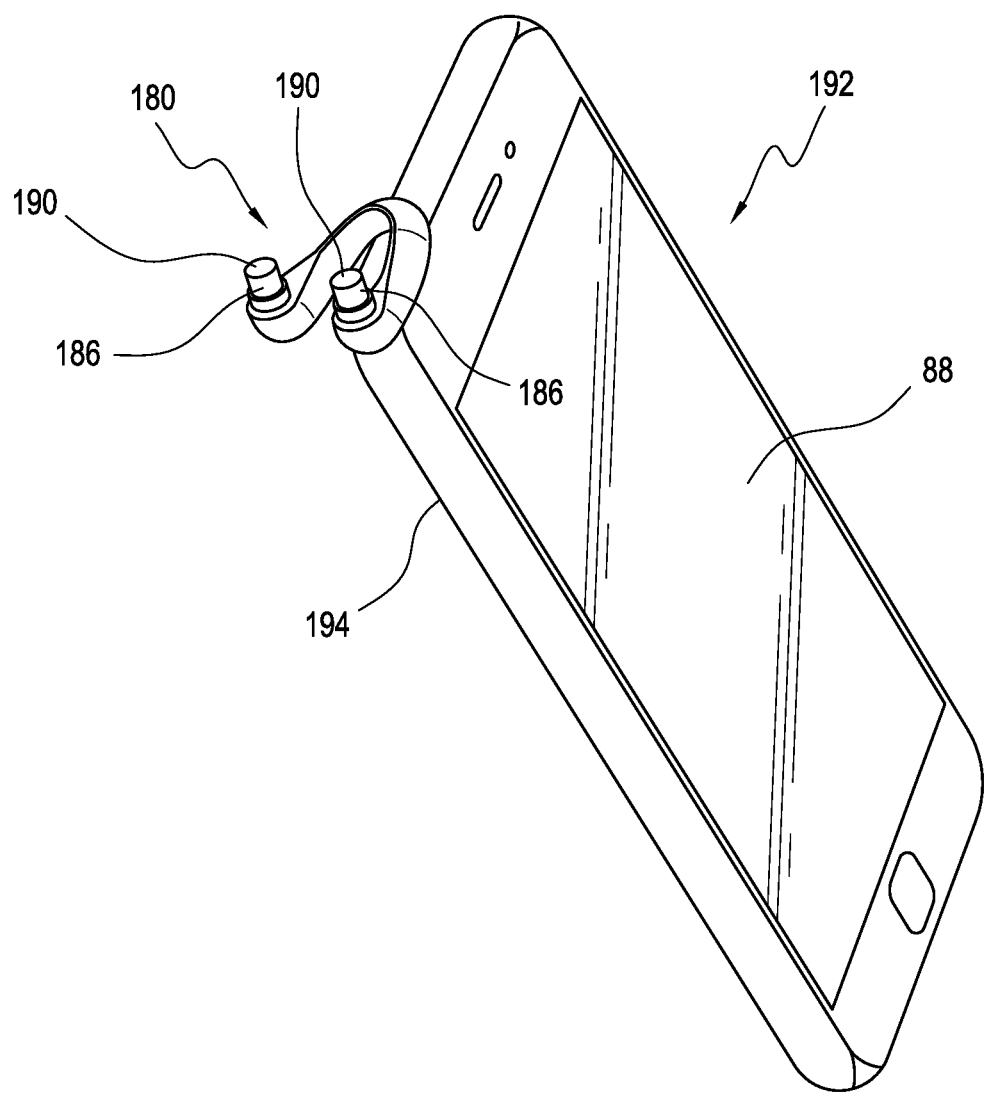
FIG. 25 shows a perspective view of an electronic apparatus incorporating the separable sensor device of FIG. 24 in accordance with another exemplary embodiment of the present disclosure.

FIG. 25 shows separable sensor device 180 positioned on an apparatus body 194 of an electronic apparatus 192, secured by jack 182. In an alternative embodiment, a separable sensor device 196 includes a wire or cable 198 terminating in a jack 200, as shown in FIG. 26. Jack 200 is configured to mate with an electrical connector 202 positioned in apparatus body 194 to form a system.

FIG. 27 shows a sensor system, indicated generally at 210, in accordance with an exemplary embodiment of the present disclosure. Sensor system 210 includes a separable sensor device 212 including a near field wireless transmitter operatively coupled to a remote electronic apparatus 214, which includes at least a complementary wireless receiver. Thus, separable sensor device 212 can be physically entirely separate from a corresponding electronic apparatus 214 and still communication with electronic apparatus 214 for the purpose of acquiring emissions from ABTT terminus 10.

Application of energy, including thermal energy to ABTT terminus 10, has been shown by Applicant to treat a variety of disorders, including Alzheimer's disease, Parkinson's disease, multiple sclerosis, cancer, and hyperthermia and hypothermia conditions. The present disclosure discloses temperature modification devices and systems connecting temperature modification devices operatively coupled with electronic apparatus, configured to remove and apply heat to ABTT terminus 10. Temperature modification elements located in temperature modification devices can be bi-directional thermoelectric devices that are configured to provide heating and cooling, resistive heaters, fluid systems, infrared lights, infrared LEDs, or other devices configured to change modify temperature.

FIG. 29 shows a temperature modification device, indicated generally at 220, and an electronic apparatus, indicated generally at 222. When temperature modification device 220 is positioned on, attached to, or connected to electronic apparatus 222, a temperature sensing and modification system 224 is formed. Temperature modification device 220 can connect or attach to an apparatus body 226 of electronic apparatus 222 via an electrical connector or jack 228, which mates with an electrical connector 238 positioned in apparatus body 226. Temperature modification device 220 includes two flexible arms 230 that can be similar or identical to flexible arms 184 described elsewhere herein, and which can be approximately parallel or parallel. Each of flexible parallel arms 230 includes at least one temperature modification element 231 and a sensor 232 positioned at a distal terminus 234. Each sensor 232 includes a measuring surface 236 disposed essentially perpendicular to the longest dimension of arm and configured to measure a signal at ABTT terminus 10.

FIG. 30 shows a view of a temperature modification device, indicated generally at 240, in accordance with another exemplary embodiment of the present disclosure. Temperature modification device 240 includes some features either similar to or identical to the features of temperature modification device 220. Accordingly, similar or identical elements in FIG. 30 to those of FIG. 29 are labeled with the same element numbers. Temperature modification device 240 includes a wire or cable 242 terminating in a jack 244. Jack 244 is configured to mate with an electrical connector 238 positioned in apparatus body 226 to form a system.

FIG. 31 shows a view of a temperature modification device, indicated generally at 250, in accordance with yet another exemplary embodiment of the present disclosure. Temperature modification device 250 is similar in some ways to temperature modification device 220 shown in FIG. 29, and is accordingly similarly labeled for brevity. Temperature modification device 250 includes a transmitter 252 for communication with a separate or remote electronic apparatus, such as electronic apparatus 222 shown in FIG. 29.

Considering the anatomy of ABTT terminus and morphology of a bridge of the nose, an arm that forms part of a separable sensor device or a temperature modification device includes a specialized dimension for fitting on or around the ABTT area. The preferred length of an arm, such as arm 184, is equal to or less than 100 mm, is more preferably equal to or less than 50 mm, is even more preferably equal to or less than 30 mm, is even yet more preferably equal to or less than 20 mm, and is most preferably equal to or less than 10 mm. The preferred diameter (or width) of each arm is equal to or less than 40 mm, is more preferably equal to or less than 20 mm, is even more preferably equal to or less than 15 mm, is even yet more preferably equal to or less than 10 mm, and is most preferably equal to or less than 5 mm.

FIG. 32 shows a view of a temperature modification device, indicated generally at 260, in accordance with still yet another exemplary embodiment of the present disclosure. Elements that are functionally similar to previously described temperature modification device 220 are similarly labeled. Temperature modification device 220 includes a processor 262, a transmitter 264, a power source 268, and two longitudinally extending, flexible, parallel arms 268. Each flexible parallel arm includes a heat transfer device 270 at a distal end or terminus 272, each heat transfer device 270 includes a heat transfer surface 274. Each heat transfer device 270 extends in a direction that is approximately perpendicular to the longitudinal direction of a respective arm 268. Heat transfer surface 274 and heat transfer device 270 are configured to apply to or remove heat from ABTT terminus 10. Arms 268 are connected by a spring mechanism 276 for securing temperature modification device 260 on the user's nose applying pressure against the nose. It should be understood that any mechanism and compression mechanism, adhesive mechanisms and the like to support the assembly on the nose can be used and are within the scope of the disclosure. It should further be understood that any embodiment for temperature modification can used in any separable sensor device and in conjunction with any sensor of the present disclosure, and any embodiment for a sensor can be used with any temperature modification device of the present disclosure.

Figure 33:
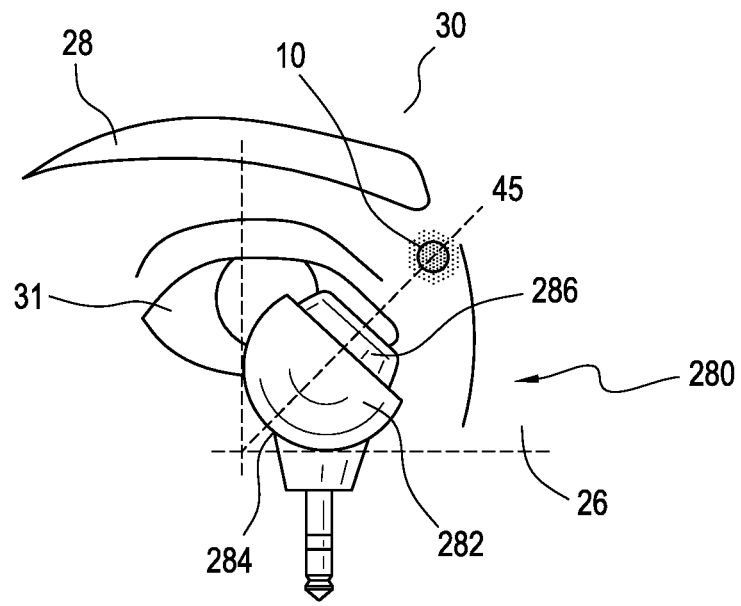
FIG. 33 shows a view of a separable sensor device in accordance with an exemplary embodiment of the present disclosure.

FIG. 33 shows a view of a separable sensor device, indicated generally at 280, in accordance with an exemplary embodiment of the present disclosure. Separable sensor device 280 is configured to include a sensor head 282 and a rotating mechanism 284 that rotates sensor head 282. Sensor head 282 includes a sensor 286 positioned thereon. Rotating mechanism 284 is configured to positioned sensor 286 at a 45 degree angle in relation to the ground, which allows alignment with ABTT terminus 10, since the skin entrance of ABTT 12 is located adjacent to the corner made by the eyebrow and bridge of the nose, and underneath the eyebrow.

Figure 34:
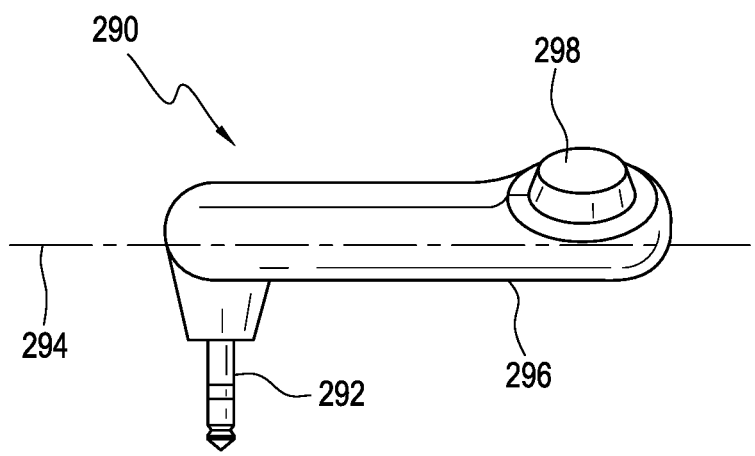
FIG. 34 shows a view of a separable sensor device in accordance with another exemplary embodiment of the present disclosure.
Figure 36:
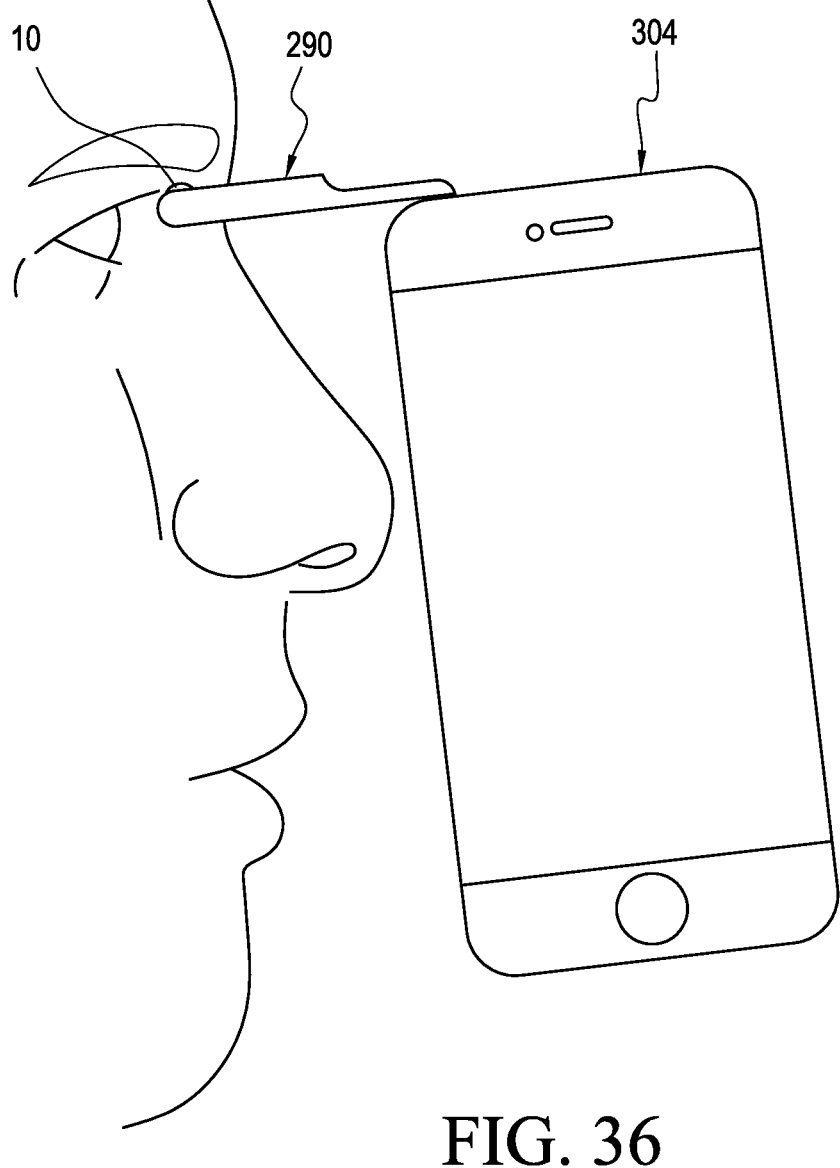
FIG. 36 shows a view of the separable sensor device of FIG. 34 inserted into an electronic apparatus in accordance with an exemplary embodiment of the present disclosure.

FIGS. 34 and 36 show views of a separable sensor device, indicated generally at 290, in accordance with another exemplary embodiment of the present disclosure. Separable sensor device 290 includes an electrical connector or jack 292 that extends in a direction that is approximately perpendicular to a longitudinal axis 294 that extends along a longitudinal body 296 of separable sensor device 290. Separable sensor device 290 includes a sensor surface 298 that extends in a direction that is away connector 292. FIG. 36 shows a view of separable sensor device 290 connected to an electronic apparatus 304 and positioned to acquire emissions from ABTT terminus 10.

Figure 35:
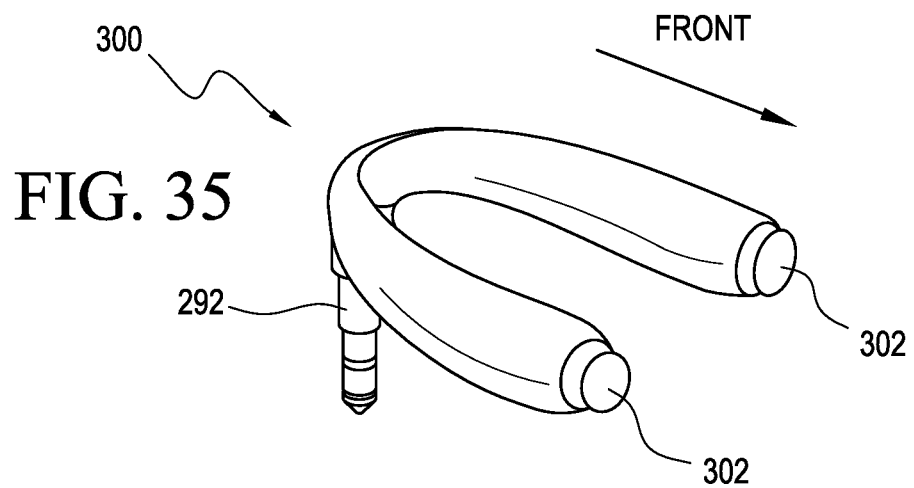
FIG. 35 shows a perspective view of another separable sensor device in accordance with an exemplary embodiment of the present disclosure.

FIG. 35 shows a perspective view of another separable sensor device, indicated generally at 300, in accordance with an exemplary embodiment of the present disclosure. Separable sensor device 300 includes a plurality of sensor measuring surfaces 302 that are approximately parallel to the longitudinal extent of connector 292 of separable sensor device 300. Both sensor measuring surface 302 are oriented to be approximately parallel to each other and to be oriented to face in a front or forward direction.

It should be understood that a sensor measuring surface can be disposed in any orientation on a measuring arm, including facing forward, as shown in FIG. 35, diagonally, as shown in FIG. 33, and upwardly, as shown in FIG. 34. It should also be understood that all embodiments of sensor assemblies can be used in embodiments of temperature modification devices, and the embodiments of temperature modification devices can have heat transfer surface disposed at angles and in similar orientations as manner as measuring surfaces of various separable sensor devices and sensor.

Figure 37:
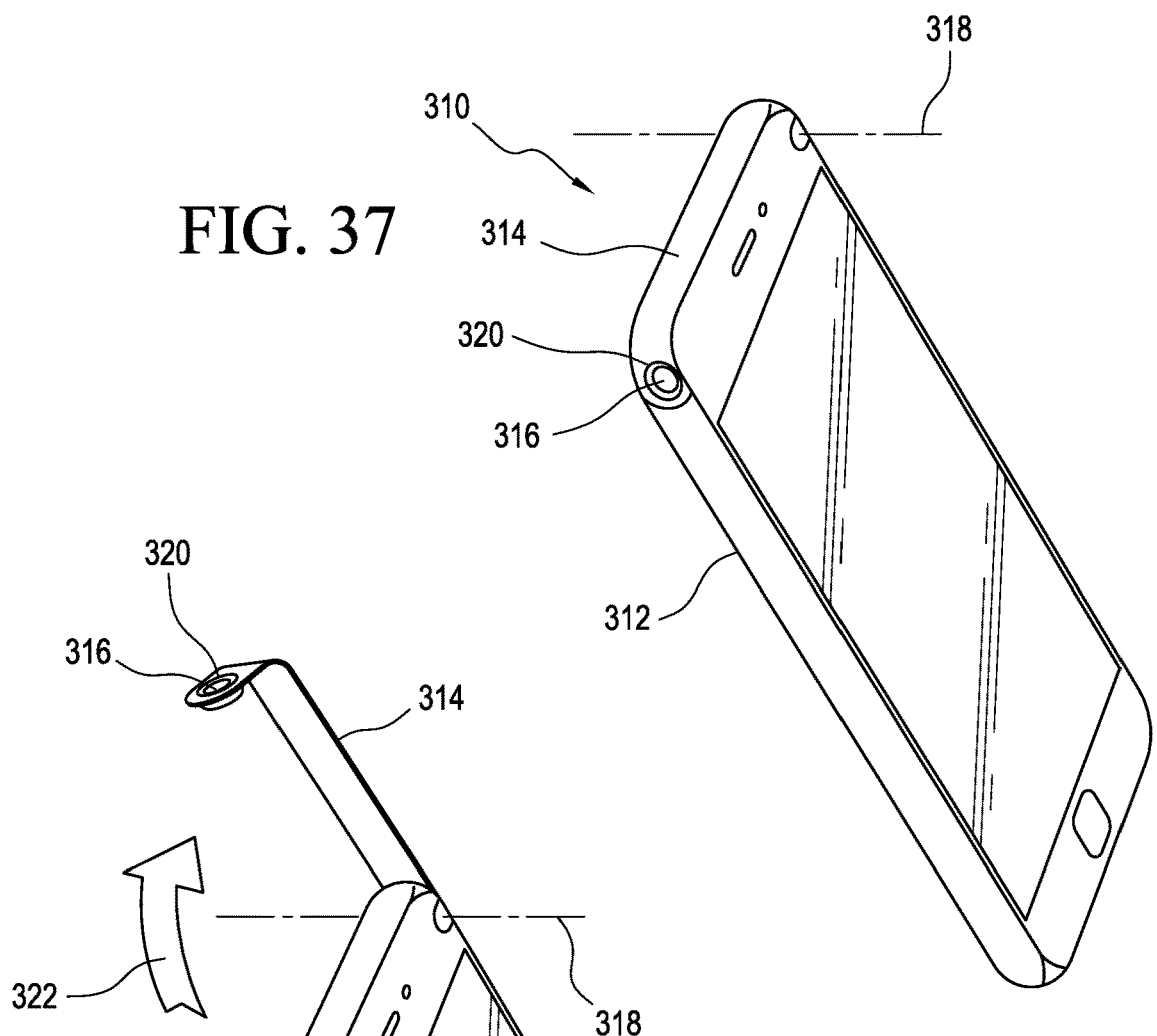
FIG. 37 shows a view of an electronic apparatus configured with a measurement device in accordance with an exemplary embodiment of the present disclosure.
Figure 38:
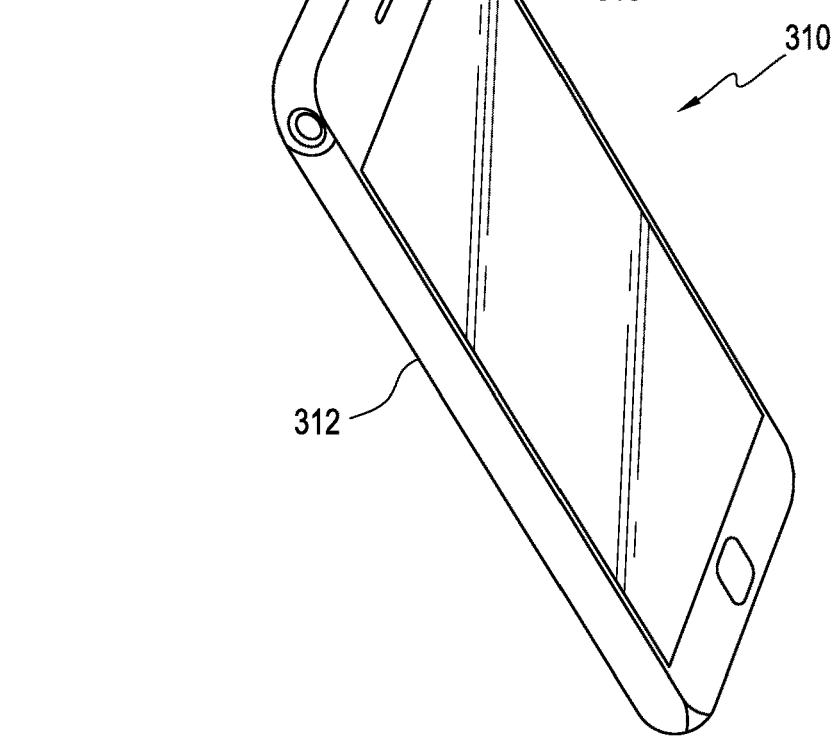
FIG. 38 shows another view of the electronic apparatus of FIG. 37.
Figure 39:
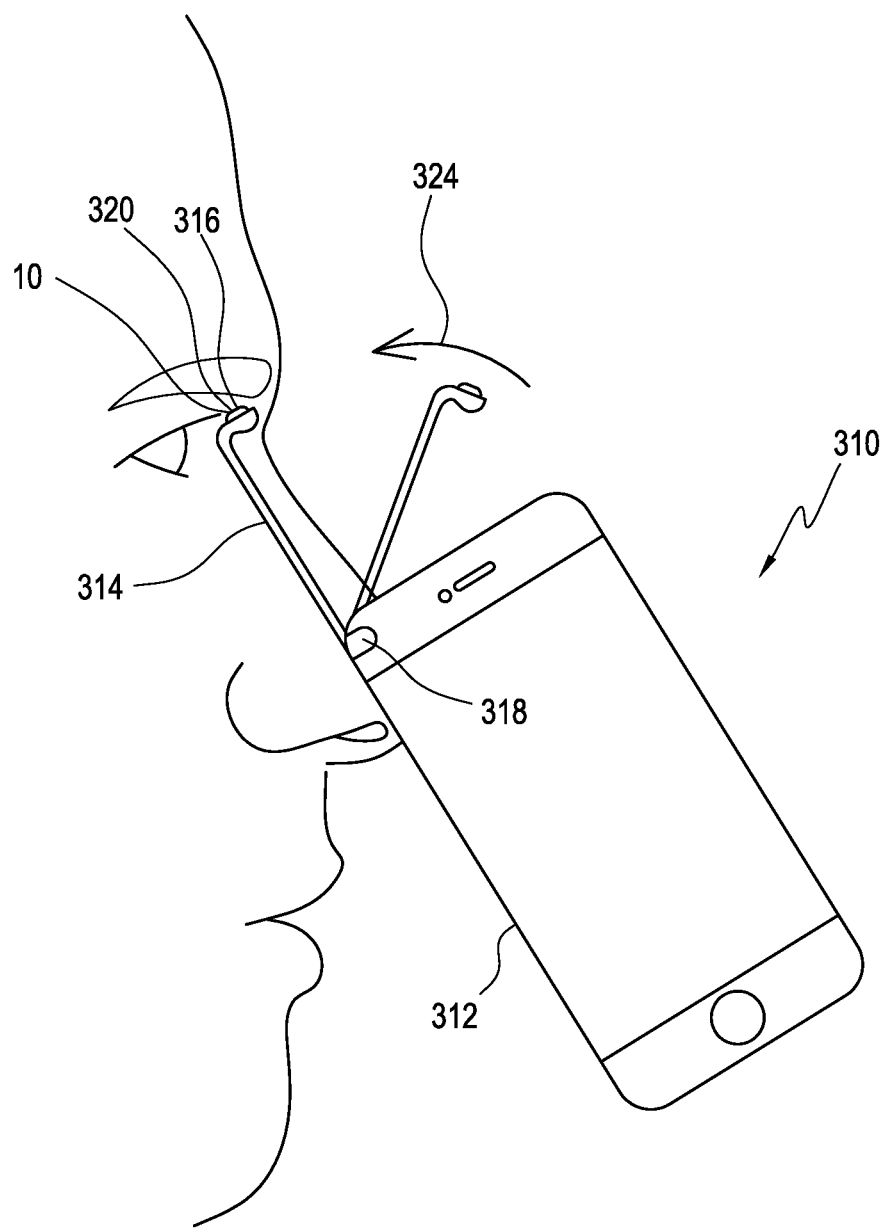
FIG. 39 shows yet another view of the electronic apparatus of FIG. 37.

FIG. 37-39 show views of an electronic apparatus, indicated generally at 310, configured with a measurement device in accordance with an exemplary embodiment of the present disclosure. Electronic apparatus 310 includes an apparatus body 312, and apparatus body 312 includes a movable, rotatable, or flippable arm 314. Flippable arm 314 includes a sensor 316 positioned at a distal or far end of arm 314 from a pivot or rotation axis 318 of arm 314. Sensor 316 is oriented with a sensor surface 320 that is approximately perpendicular to a longitudinal extent of arm 314. As shown in FIG. 39, arm 314 rotates in the direction of arrow 322 shown in FIG. 38 and in the direction of arrow 324 in FIG. 39 to position sensor 316 at a spaced distance from electronic apparatus 310 in a location to acquire an emission from ABTT terminus 10 of the user, with sensor 316 resting on or adjacent to ABTT terminus 10. It should be understood that sensor can be replaced by a temperature modification device, in similar manner as shown in previous sensor embodiments, and said temperature modification device embodiments are within the scope of the present disclosure.

FIGS. 40 to 47 show alternative embodiment separable sensor devices in accordance with exemplary embodiments of the present disclosure. The separable sensor devices shown in FIGS. 40-47 are similar to the separable sensor devices shown in FIGS. 24 to 28, however, the embodiments of FIGS. 40-47 include only a single sensor and a single arm to support the sensor, and an end of each separable sensor device opposite the end with the sensor terminates in a c-shape nose support. When features between the embodiments are common or similar, the same element number is used for the sake of brevity.

Figure 43:
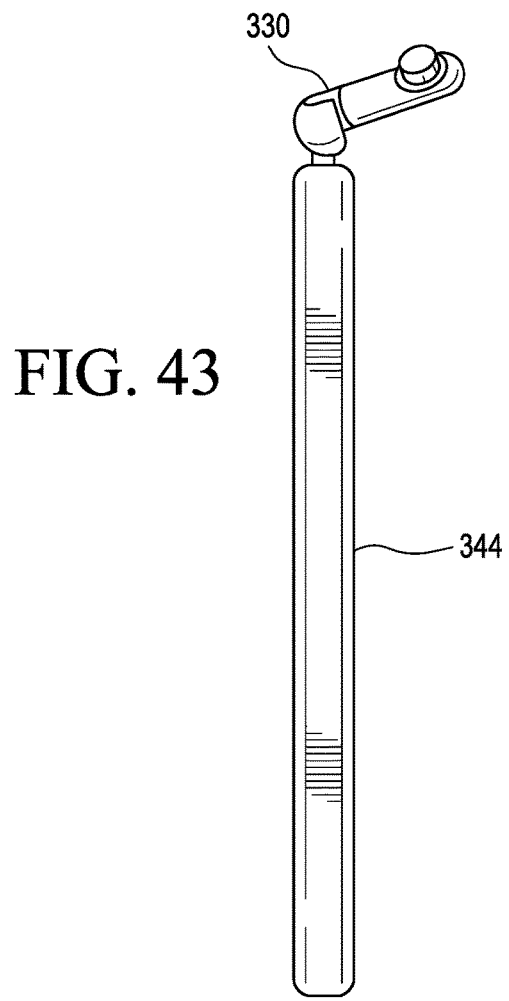
FIG. 43 shows a further view of the separable sensor device and the electronic apparatus of FIGS. 41 and 42.
Figure 44:
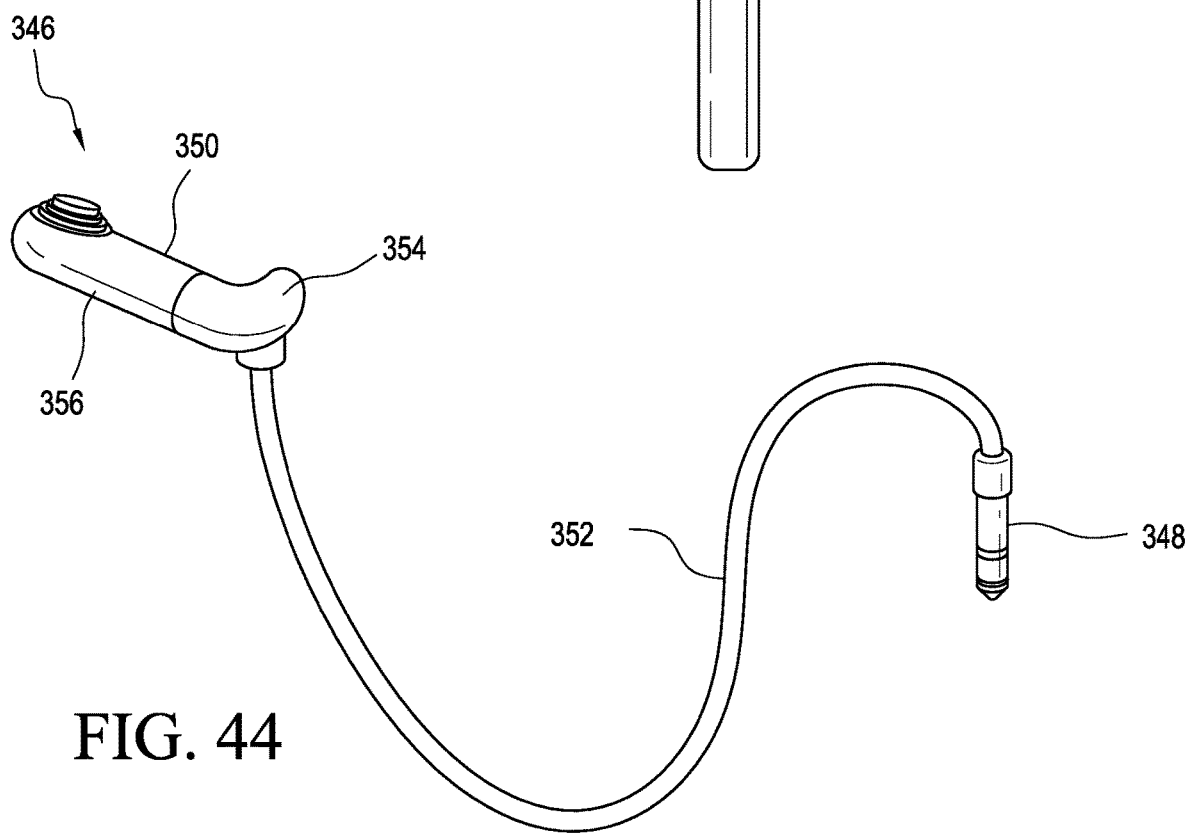
FIG. 44 shows a view of a yet even further separable sensor device in accordance with an exemplary embodiment of the present disclosure.
Figure 45:
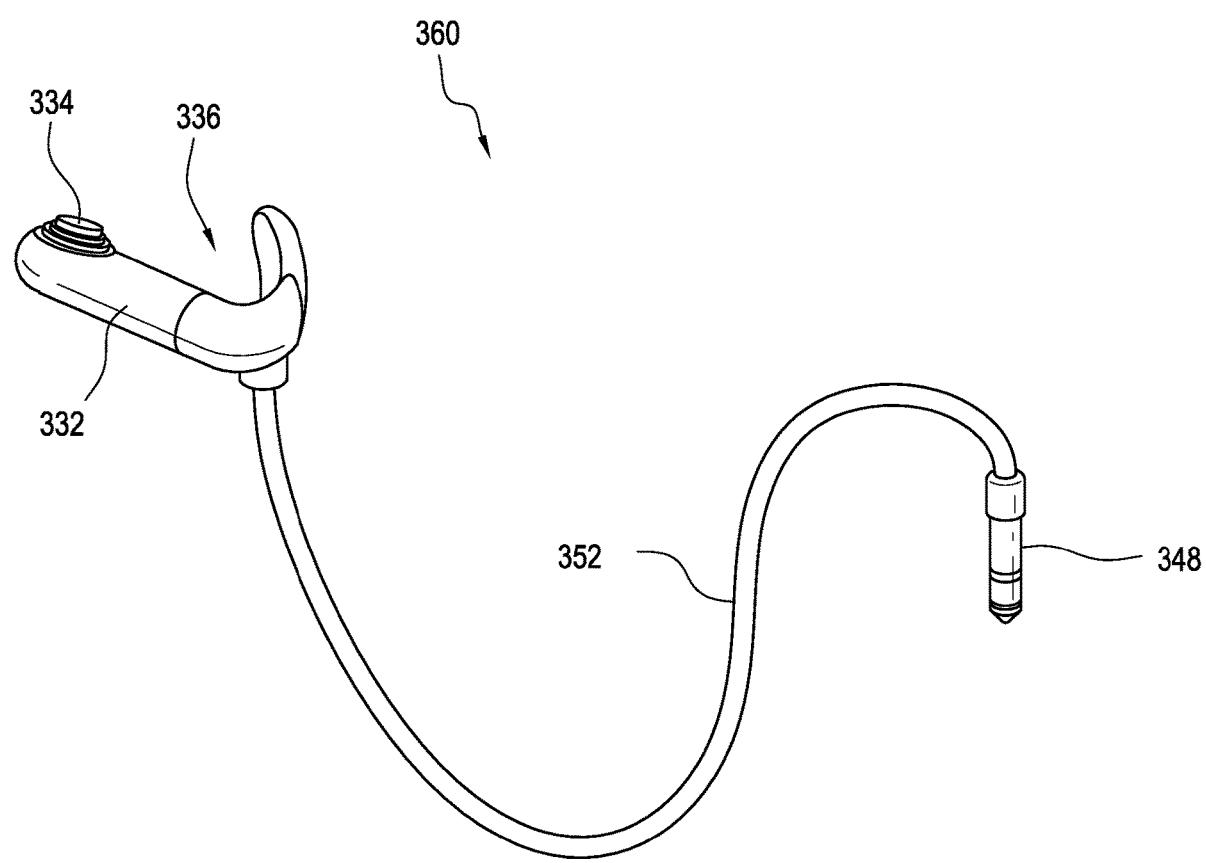
FIG. 45 shows a view of a still further separable sensor device in accordance with an exemplary embodiment of the present disclosure.
Figure 46:
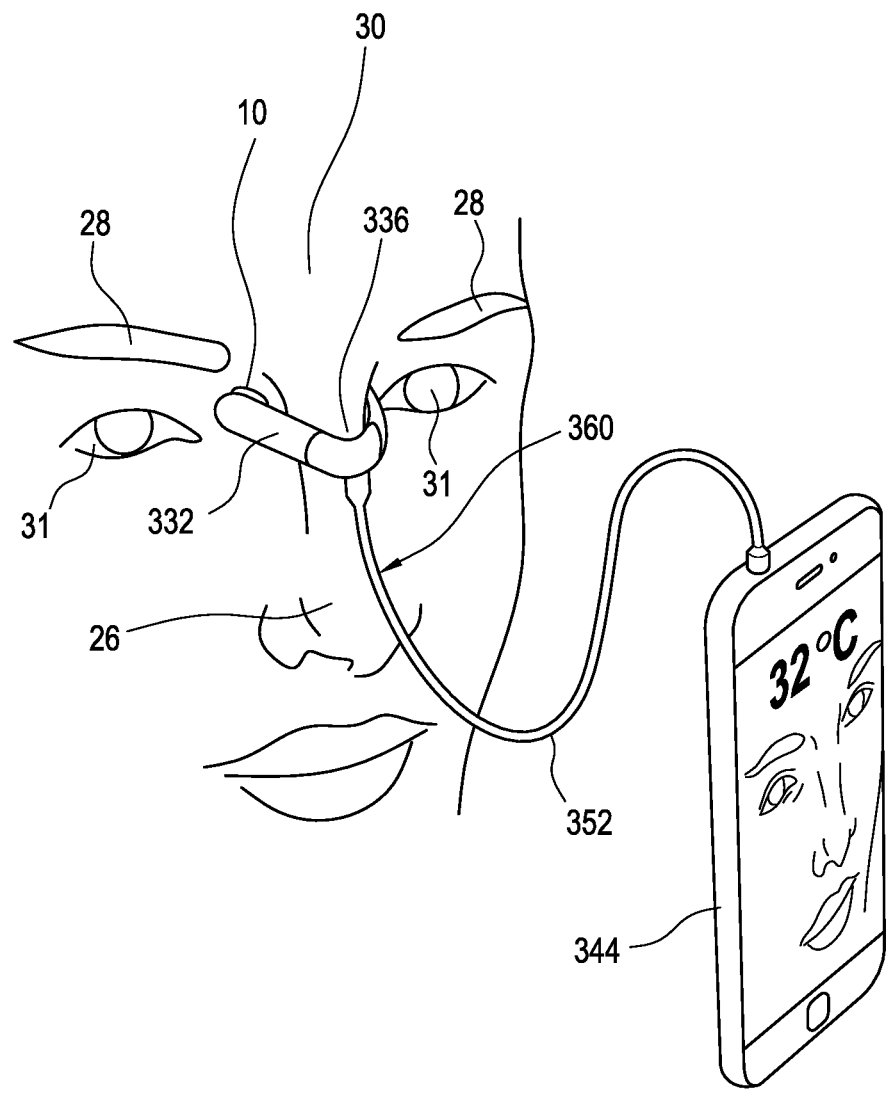
FIG. 46 shows a perspective view of the separable sensor device of FIG. 45 attached to an electronic apparatus with the separable sensor device positioned on a nose of a user in accordance with an exemplary embodiment of the present disclosure.
Figure 47:
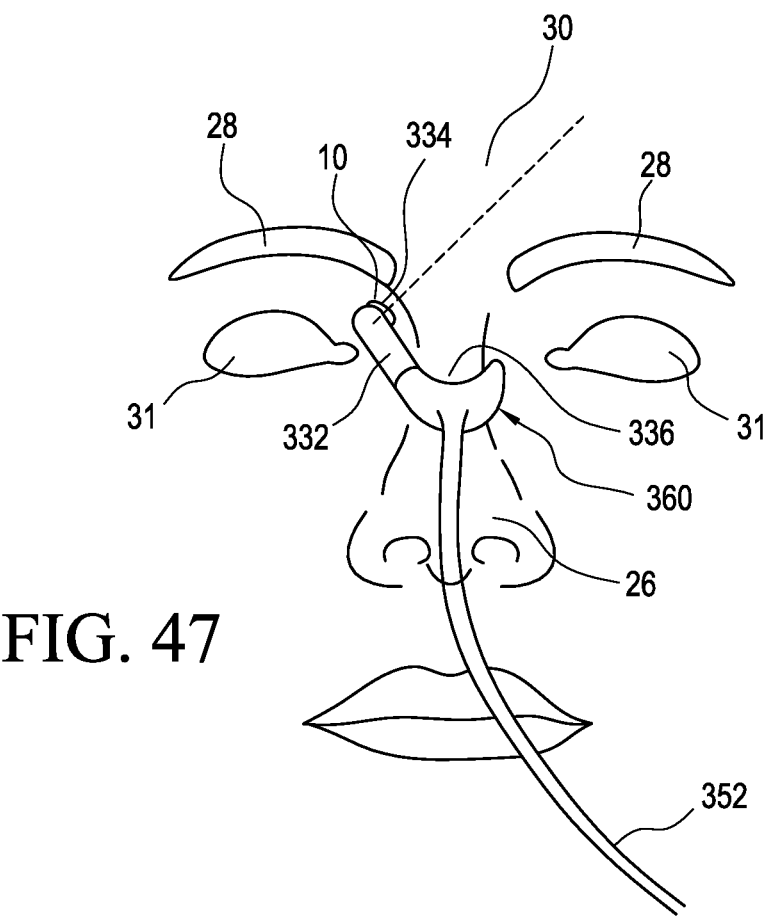
FIG. 47 shows a further view of the separable sensor device of FIG. 45 positioned on the nose of a user.

FIG. 40 shows a separable sensor device, indicated generally at 330, in accordance with an exemplary embodiment of the present disclosure and which includes a sensor support arm 332, a sensor 334 positioned on sensor support arm 332, a "C"-shaped support portion 336, and a transmitter 338. C-shaped support portion 336 is configured to conform to the shape of the user's nose, thus providing the ability to support separable sensor device 330 while ABTT terminus 10 emissions are measured. FIG. 41 shows a separable sensor device, indicated generally at 340, in accordance with an exemplary embodiment of the present disclosure. In this embodiment, transmitter 338 is replaced by an electrical connector or jack 342 configured to mate with an electrical connector positioned on an electronic apparatus, as described elsewhere herein. FIGS. 42 and 43 show separable sensor device 340 positioned on an electronic apparatus 344, supported by the connection of connector 342 with electronic apparatus 344. FIG. 44 shows a separable sensor device, indicated generally at 346, in accordance with an exemplary embodiment of the present disclosure. In this embodiment, connector or jack 342 is replaced by an electrical connector or jack 348 connected to a device body 350 of separable sensor device 346 by a wire or cable 352. Furthermore, in place of C-shaped support portion 336 is a short, straight arm 354 that is approximately perpendicular to a sensor support arm 356 of separable sensor device 346. FIGS. 45-47 shows a separable sensor device, indicated generally at 360, in accordance with an exemplary embodiment of the present disclosure. Separable sensor device 360 includes features of separable sensor device 336 shown in FIG. 41 and separable sensor device 346 shown in FIG. 44, and is labeled accordingly. FIG. 45 shows double axis rotation movement of separable sensor device 360, one first rotation to position at 45 degrees angle in relation to the main axis of apparatus body, and a second rotation of the sensor head to a 45 degrees angle in relation to the axis of the arm, for alignment with ABTT terminus 10. FIG. 46 shows separable sensor 360 being positioned on nose 26 and aligned with ABTT terminus 10. FIG. 47 shows an angle of sensor 334 for preferred alignment with ABTT terminus 10.

Figure 48:
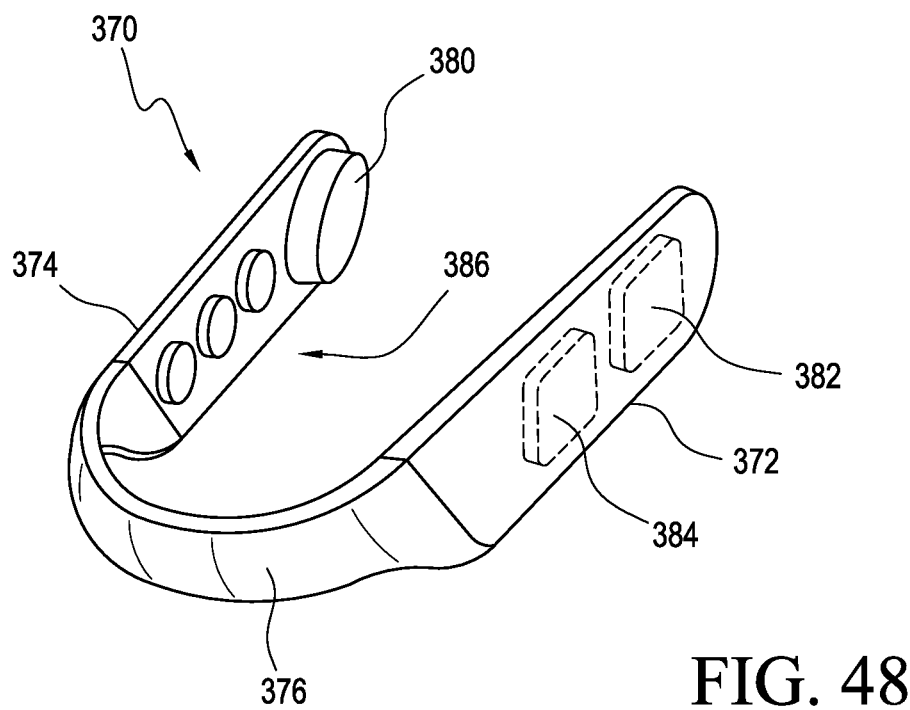
FIG. 48 shows a perspective view of another separable sensor device in accordance with an exemplary embodiment of the present disclosure.

FIG. 48 shows a perspective view of another separable sensor device, indicated generally at 370, in accordance with an exemplary embodiment of the present disclosure. Separable sensor device 370 includes a first, right arm 372, a second, left arm 374, each of which are essentially flat or planar for apposition to the skin of nose 26, and a connecting portion 376 positioned between and connected to right arm 372 and left arm 374. Connecting portion 376 includes an adhesive surface 378 to anchor separable sensor device 370 to the skin of nose 26. At least one of right arm 372 and left arm 274 includes a sensor 380 positioned at a distal or free end thereof. Separable sensor device 370 further includes a transmitter 382 for wireless communication, which can be, for example, Wi-Fi or Blue Tooth, a processor 384, and a power source 386, such as one or more batteries.

FIG. 49 shows a view of yet another separable sensor device, indicated generally at 390, in accordance with an exemplary embodiment of the present disclosure. Separable sensor device 390 includes a first, right arm 392, a second, left arm 394, each of which are essentially flat or planar for apposition to the skin of nose 26, and a connecting portion 396 positioned between and connected to right arm 392 and left arm 394. Connecting portion 396 includes an adhesive surface 398 to anchor separable sensor device 390 to the skin of nose 26. Adhesive surface 398 is covered by a peelable protective cover or layer 400. Each of right arm 392 and left arm 394 includes a sensor 402 positioned at a distal or free end thereof. Separable sensor device 390 further includes, for balance between right arm 392 and left arm 394, a power source 404 positioned on right arm 392 and an integrated circuit 406 that includes a processor and a transmitter (i.e., a wireless device). The electronic elements of right arm 392 and left arm 394 are connected by wires or preferably a flexible circuit (not shown).

FIG. 50 shows a perspective view of a further separable sensor device, indicated generally at 410, and an electronic apparatus, indicated generally at 412, in accordance with an exemplary embodiment of the present disclosure. Separable sensor device 410 and electronic apparatus 412 form a sensor system 414. Separable sensor device 410 includes a left arm 416, a right arm 418, and a spring 420 or other compressible material with spring capabilities, including plastic with memory, configured to force left arm 416 and right arm 418 toward each other, which means that left arm 416 and right arm 418 will be pressed against the sides of nose 26 when separable sensor device 410 is placed on a nose. Each of left arm 416 and right arm 418 includes sensor 402 positioned at a free or distal of each arm for balance. Sensor system 414 also includes a wire or cable 422 for connecting separable sensor device 410 to electronic apparatus 412. Electronic device 412 is configured to include a power source 424, a processor 426, a transmitter 428, and a display 430.

Figure 51:
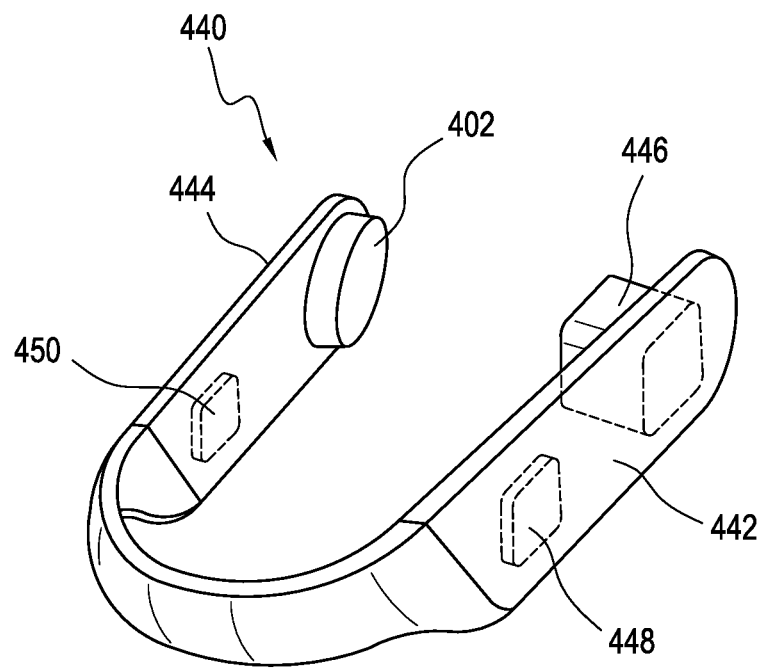
FIG. 51 shows a perspective view of a still further separable sensor device in accordance with an exemplary embodiment of the present disclosure.

FIG. 51 shows a perspective view of a still further separable sensor device, indicated generally at 440, in accordance with an exemplary embodiment of the present disclosure. Separable sensor device 440 includes a left arm 442, a right arm 444. Separable sensor device 440 further includes sensor 402 located at a free or distal end of right arm 444, a temperature modification device 446 located at a free end of left arm 442, an integrated circuit 448 having a processor and wireless device positioned on left arm 442, and a power source 450 positioned on right arm 444.

Figure 52:
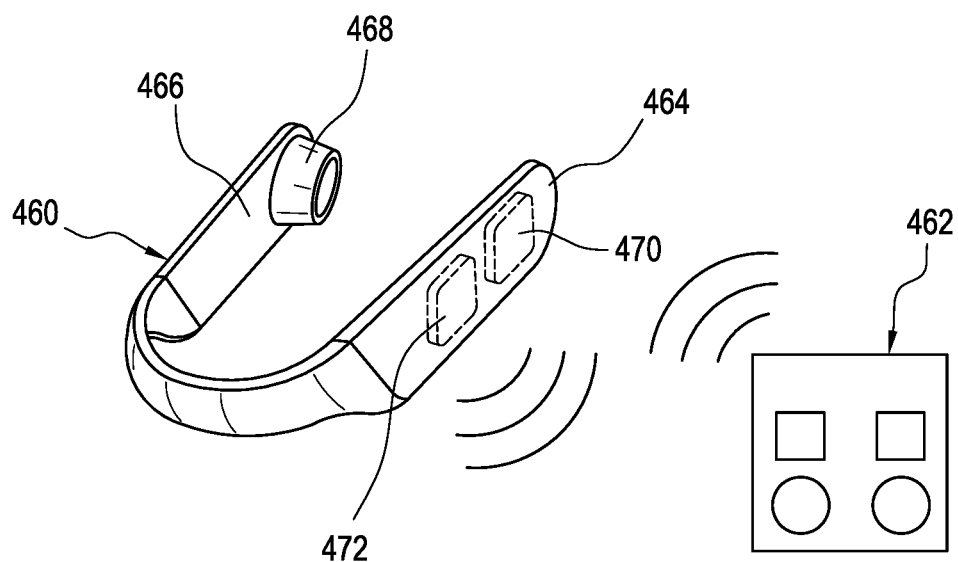
FIG. 52 shows a perspective view of a separable temperature modification device and an electronic apparatus in accordance with an exemplary embodiment of the present disclosure.

FIG. 52 shows a perspective view of a separable temperature modification device, indicated generally at 460, and an electronic apparatus, indicated generally at 462, in accordance with an exemplary embodiment of the present disclosure. Device 460 includes a left arm 464 and a right arm 466. Device 460 further includes a heat transfer device 468 positioned on a free or distal end of right arm 466, an integrated circuit 470 having a processor and wireless device positioned on left arm 464 wirelessly connected to electronic apparatus 462, which can be a cell phone, a tablet, a computer device, and the like, and a power source 472.

Figure 53:
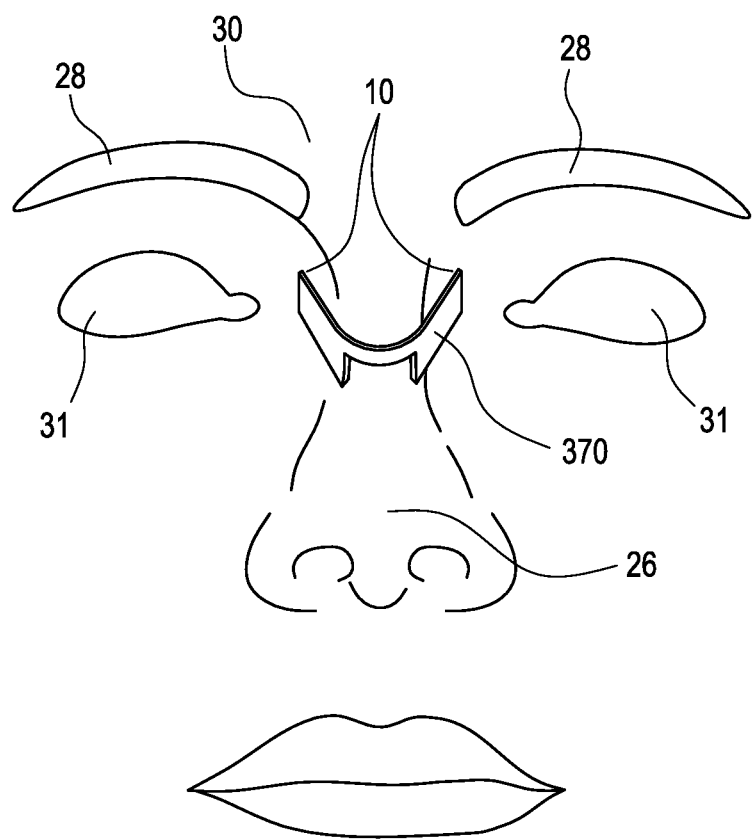
FIG. 53 shows a view of the separable sensor device of FIG. 48 positioned on the nose of a user.
Figure 54:
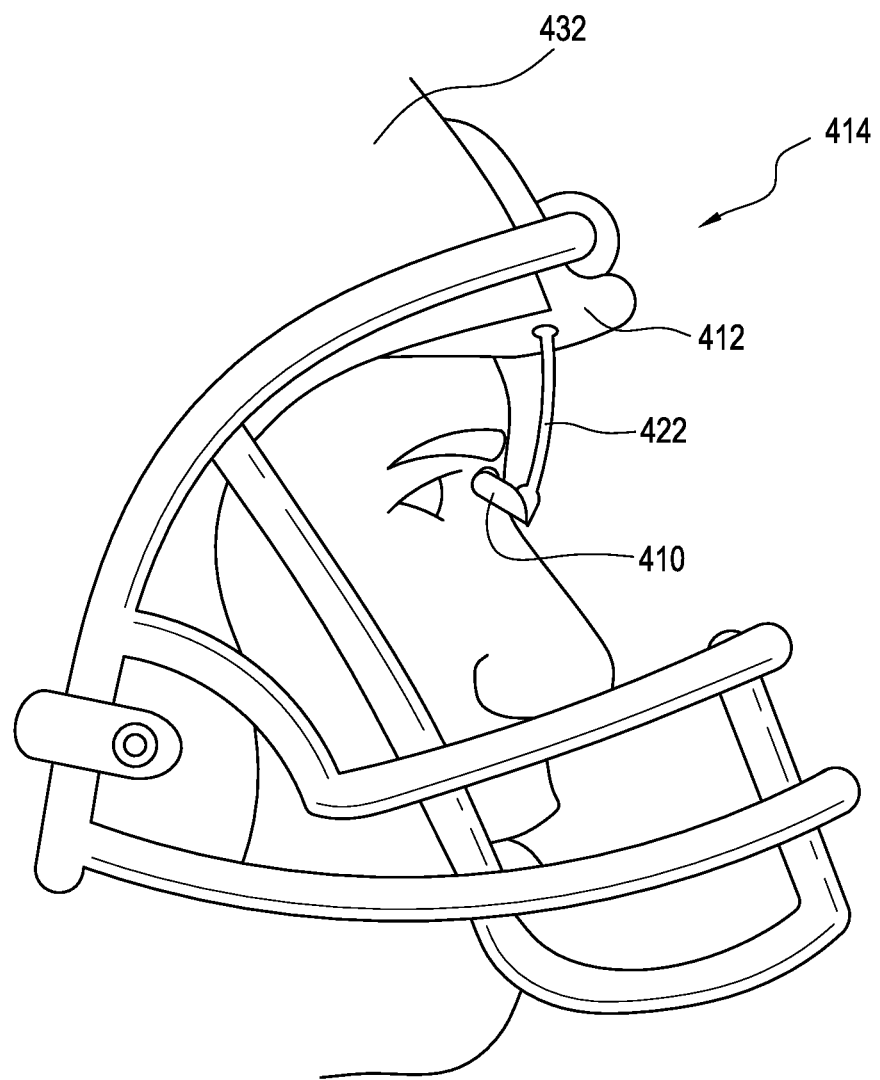
FIG. 54 shows a view of the separable sensor device of FIG. 50 positioned on the nose of a user and supported by a sport helmet in accordance with an exemplary embodiment of the present disclosure.
Figure 55:
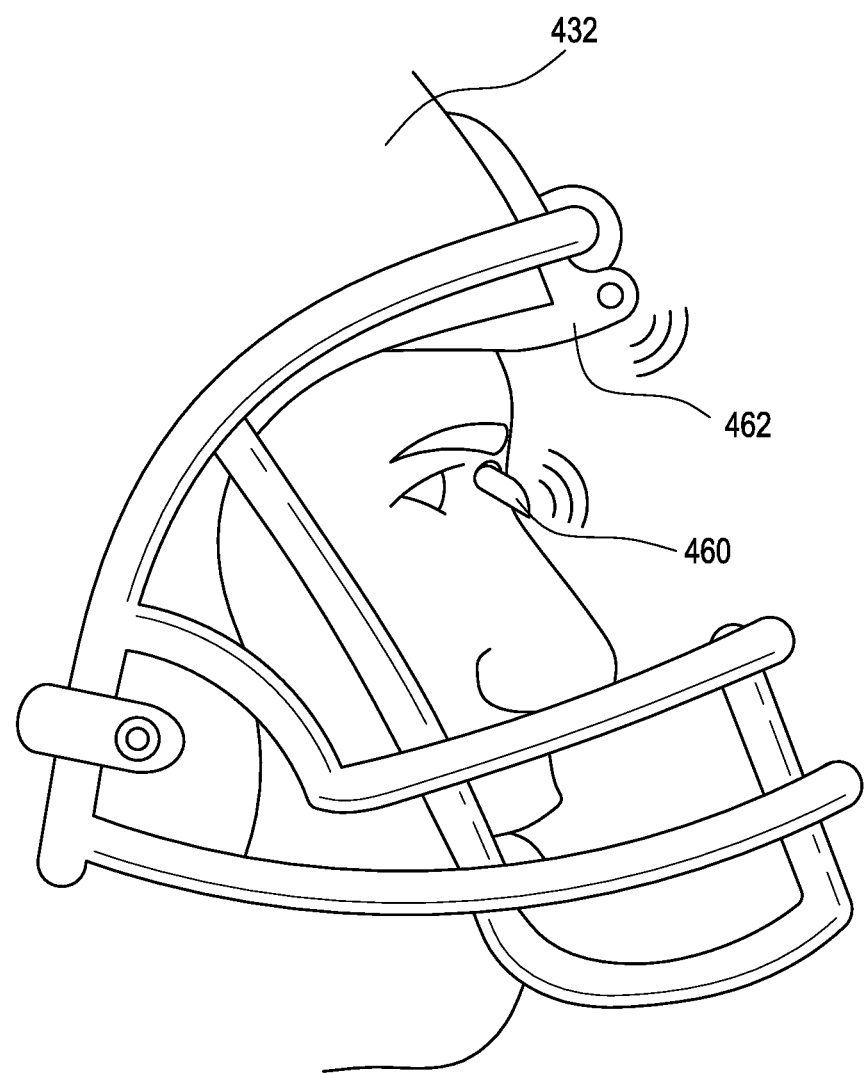
FIG. 55 shows a view of the separable sensor device of FIG. 52 positioned on the nose of a user and the electronic apparatus of FIG. 52 supported by a sport helmet in accordance with an exemplary embodiment of the present disclosure.

FIG. 53 shows a view of separable sensor device 370 shown in FIG. 48 positioned on nose 26 of the user. FIG. 54 shows a view of separable sensor device 410 and electronic apparatus 412 shown in FIG. 50 positioned on a helmet 432 and being used by the subject. FIG. 55 shows a view of temperature modification device 460 and electronic apparatus 462 positioned on helmet 432 and being used by the subject. Temperature modification device 460 communicates with electronic apparatus 462 wirelessly. It should be understood that any head-mounted gear and neck-mounted gear can be used, in accordance to the principles of the present disclosure and are within the scope of the disclosure.

Figure 56:
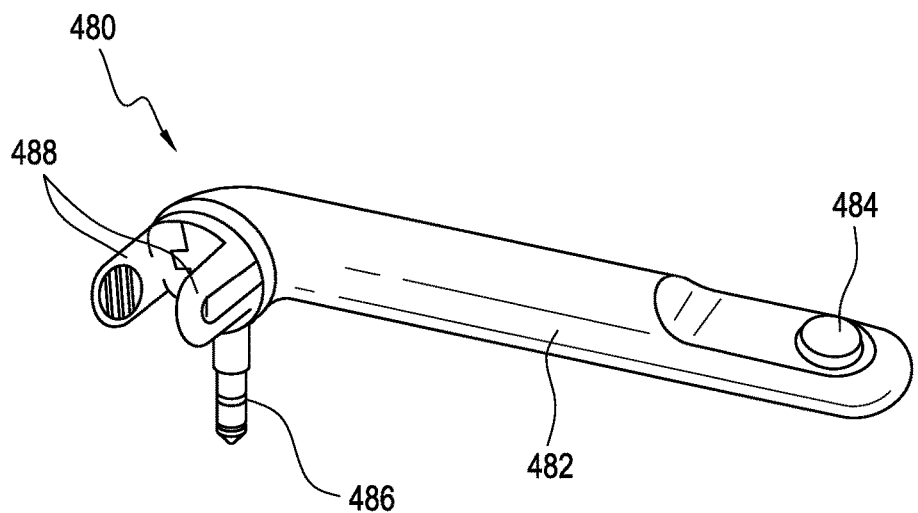
FIG. 56 shows a perspective view of a separable sensor device in accordance with an exemplary embodiment of the present disclosure.

FIG. 56 shows a perspective view of a separable sensor device, indicated generally at 480, in accordance with an exemplary embodiment of the present disclosure. Separable sensor device 480 includes a longitudinally extending rod-like body 482. Device 480 further includes a sensor 484 positioned at a distal end of body 482, an electrical connector positioned at a proximate end of body 482 and extending approximately perpendicular to a longitudinal axis through body 482, and a pair of expandable grasping arms 486. Grasping arms 486 are configured to grasp an apparatus body.

Figure 57:
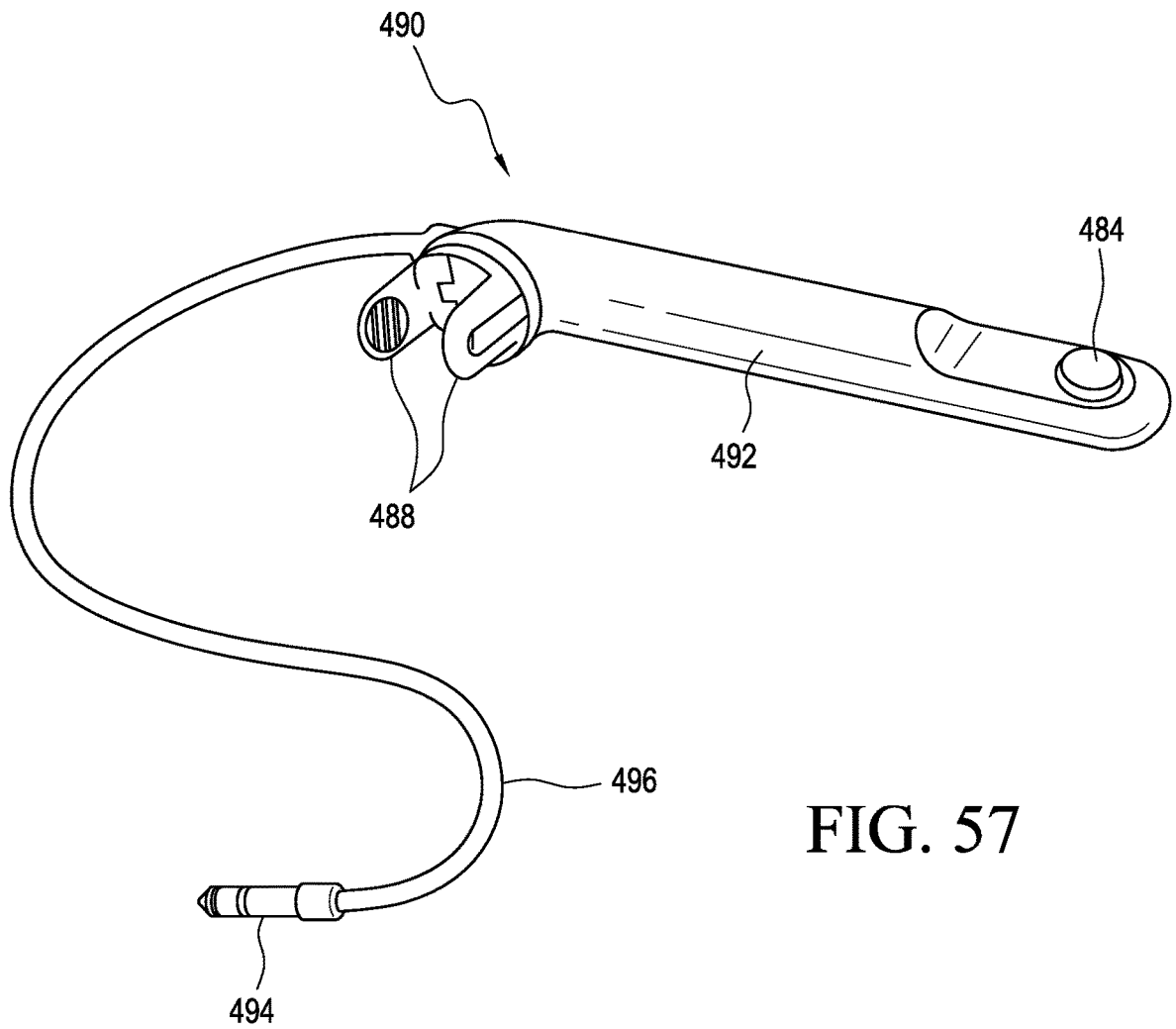
FIG. 57 shows a perspective view of another separable sensor device in accordance with an exemplary embodiment of the present disclosure.

FIG. 57 shows a perspective view of another separable sensor device, indicated generally at 490, in accordance with an exemplary embodiment of the present disclosure. Device 490 is similar to device 480 in certain aspects. Accordingly, similar elements are similarly numbered. Device 490 includes a rod-like body 492. Device 490 further includes an electrical connector or jack 494 and a cable or wire 496 that connects jack 494 to body 492.

Figure 58:
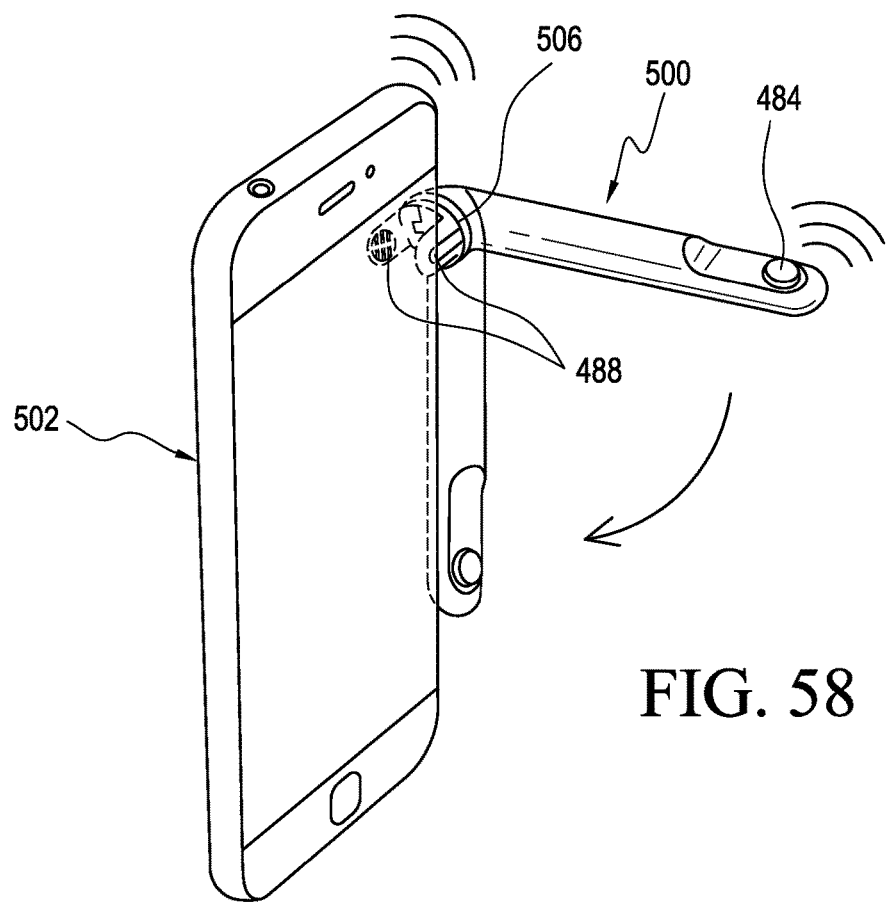
FIG. 58 shows a perspective view of a separable sensor device attached to an electronic apparatus in accordance with an exemplary embodiment of the present disclosure.

FIG. 58 shows a perspective view of a separable sensor device, indicated generally at 500, attached to an electronic apparatus, indicated generally at 502, in accordance with an exemplary embodiment of the present disclosure. Separable sensor device 500 includes a rod-like body 504. Grasping arms 488 grasp a front face of electronic apparatus 502 and a back face of electronic apparatus 502 and are connected to body 504 by a rotating mechanism 506 configured to position rod-like body 504 alongside electronic apparatus 502 in a first position or orientation and to position rod-like body 504 approximately perpendicular to electronic apparatus 502. Separable sensor device 500 also includes a wireless device, such as a transmitter, for communication with electronic apparatus 502 (e.g., operatively coupled).

Figure 59:
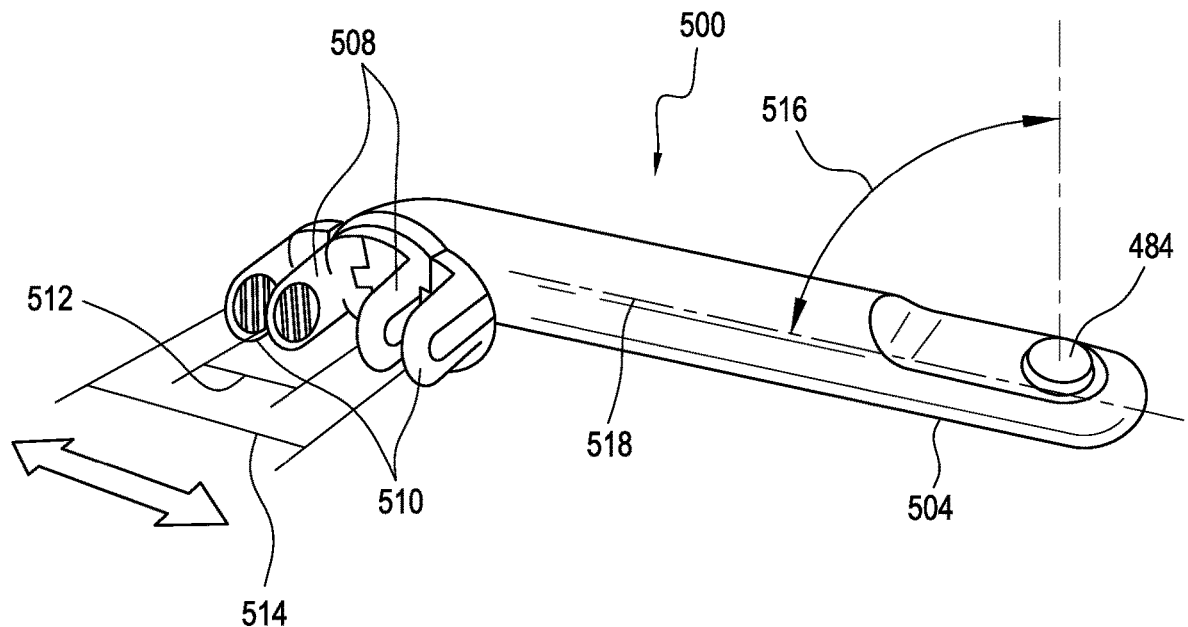
FIG. 59 shows a perspective view of a further separable sensor device in accordance with an exemplary embodiment of the present disclosure.
Figure 60:
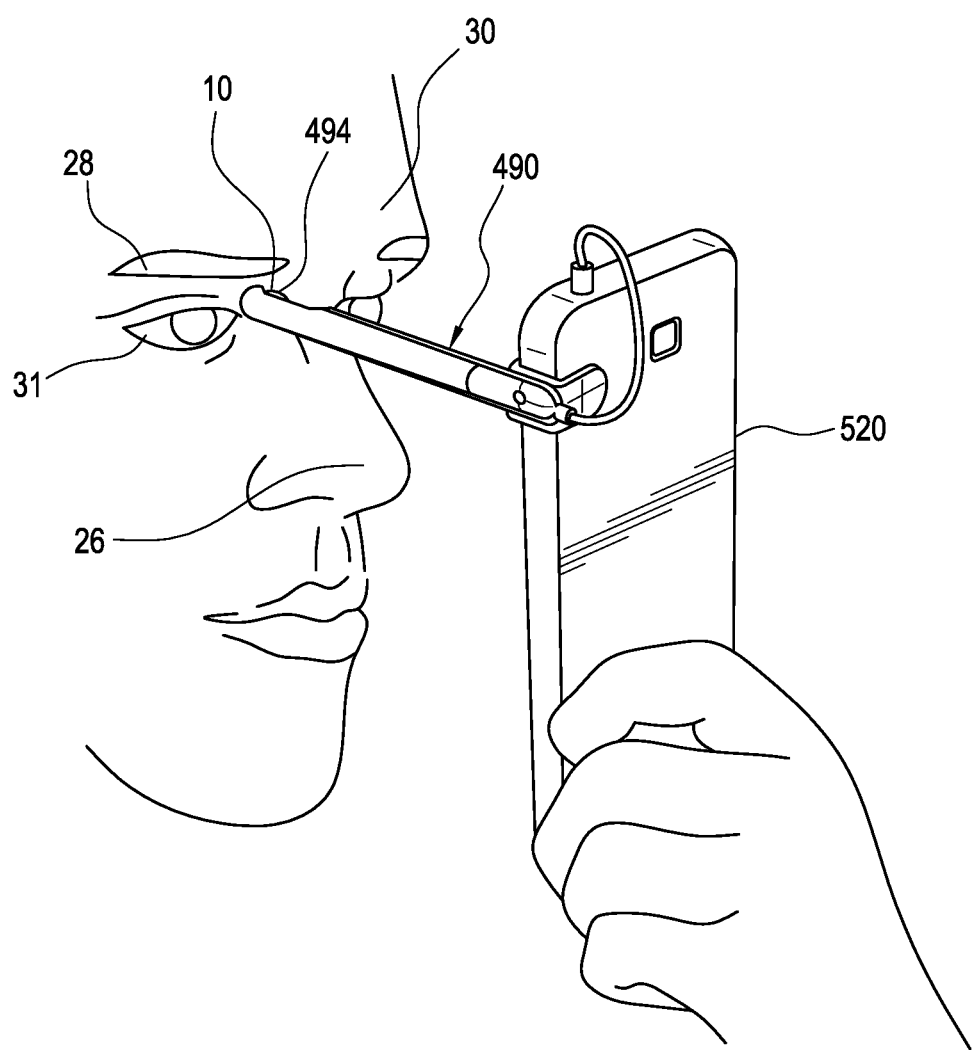
FIG. 60 shows a perspective view of the separable sensor device of FIG. 57 attached to an electronic apparatus and being used by a user to make a measurement of an emission from the ABTT.

FIG. 59 shows grasping arms 488 in a first, un-extended position 508 and in a second, extended position 510. When grasping arms 488 are in first position 508, grasping arms 508 are positioned a first spaced distance 512 apart. When grasping arms 488 are in second position 510, grasping arms 488 are positioned a second spaced distance 514, which is greater than first spaced distance 512, apart. The ability to extend or expand grasping arms 488 permits anchoring an equipped separable sensor device to different thicknesses of an apparatus body. Separable sensor device 500 is configured to position sensor 484 at a diagonal position or angle 516 in relation to a main longitudinal axis 518 of body 504.

FIGS. 61 to 64 show embodiments of a sensor case configured to mate with an apparatus body of an electronic apparatus. Each sensor case includes a sensor.

Figure 61:
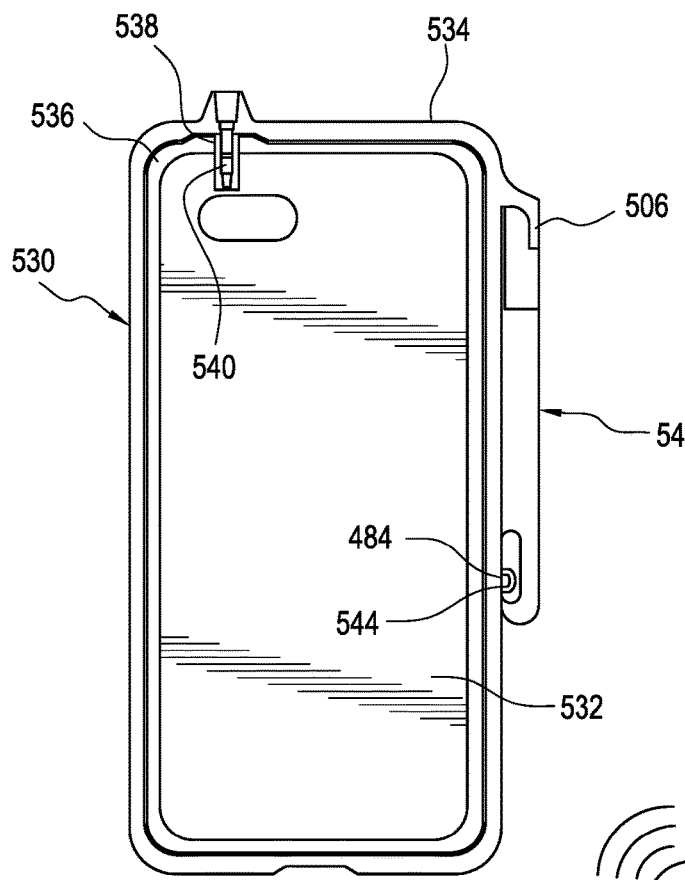
FIG. 61 shows a view of yet another separable sensor device positioned on an electronic apparatus in accordance with an exemplary embodiment of the present disclosure.

FIG. 61 shows a view of yet another separable sensor device, indicated generally at 530, positioned on an electronic apparatus, indicated generally at 532, in accordance with an exemplary embodiment of the present disclosure. Separable sensor case 530 includes a case body 534 configured to receive an apparatus body 536 of electronic apparatus 532, an electrical connector 538 configured to mate with an electrical connector 540 of electronic apparatus 532, which are shown in a cutaway portion of device 530 and electronic apparatus 532, and a sensor device 542 connected to case body 534 by rotating mechanism 506. Sensor device 542 includes a rod-like body 544 on which is positioned sensor 484. A sensor surface 544 of sensor 484 is disposed diagonally in relation to a main axis of sensor device 542. Sensor 484 generates signals proportional to emissions received by sensor 484. The signals are transmitted to connector 538.

Figure 62:
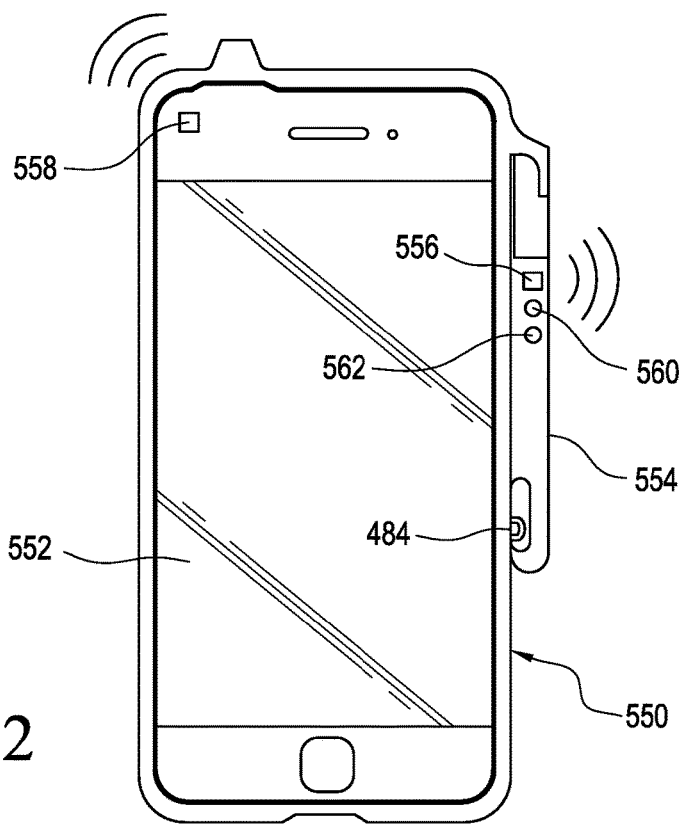
FIG. 62 shows a view of still yet another separable sensor device positioned on an electronic apparatus in accordance with an exemplary embodiment of the present disclosure.

FIG. 62 shows a view of still yet another separable sensor device, indicated generally at 550, positioned on an electronic apparatus, indicated generally at 552, in accordance with an exemplary embodiment of the present disclosure. Separable sensor device 550 includes a rod-like body 554 in which is positioned a transmitter 556 that is communicatively coupled with a receiver 558 of electronic apparatus 550. Rod-like body 554 also includes a processor 560, and power source 562.

Figure 63:
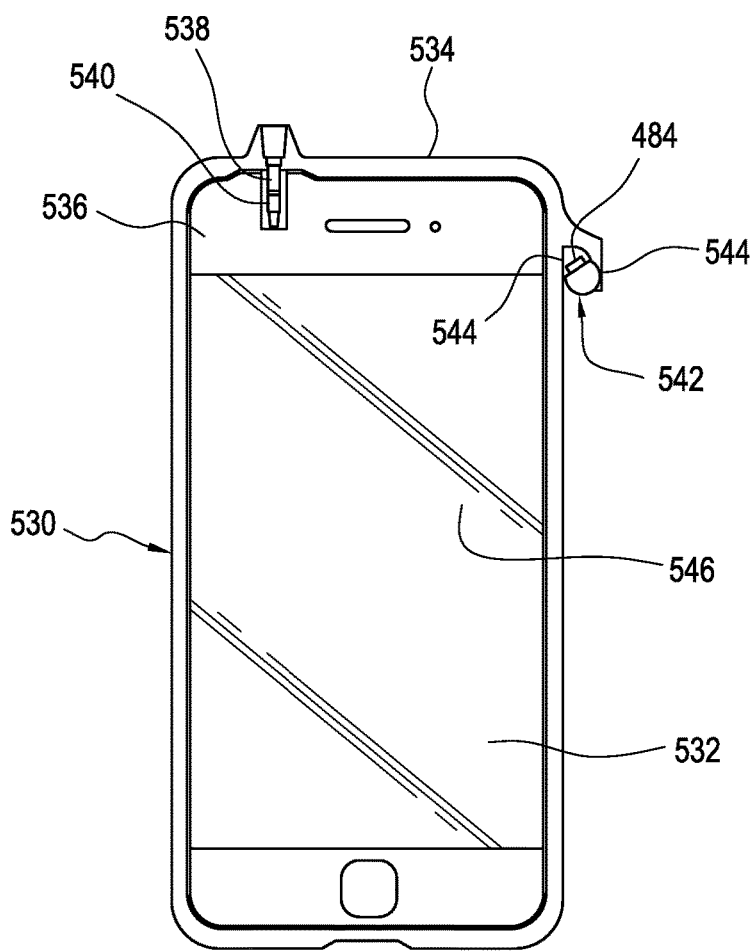
FIG. 63 shows a view of the separable sensor device and electronic apparatus of FIG. 61 with a portion of the separable sensor device pivoted to a position to measure an emission from the ABTT.
Figure 64:
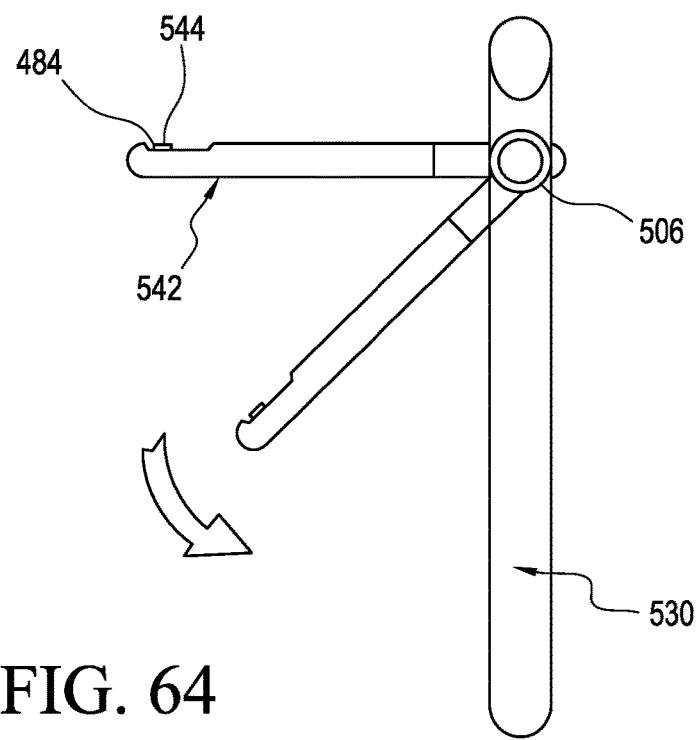
FIG. 64 shows another view of the separable sensor device and electronic apparatus of FIGS. 61 and 63.
Figure 65:
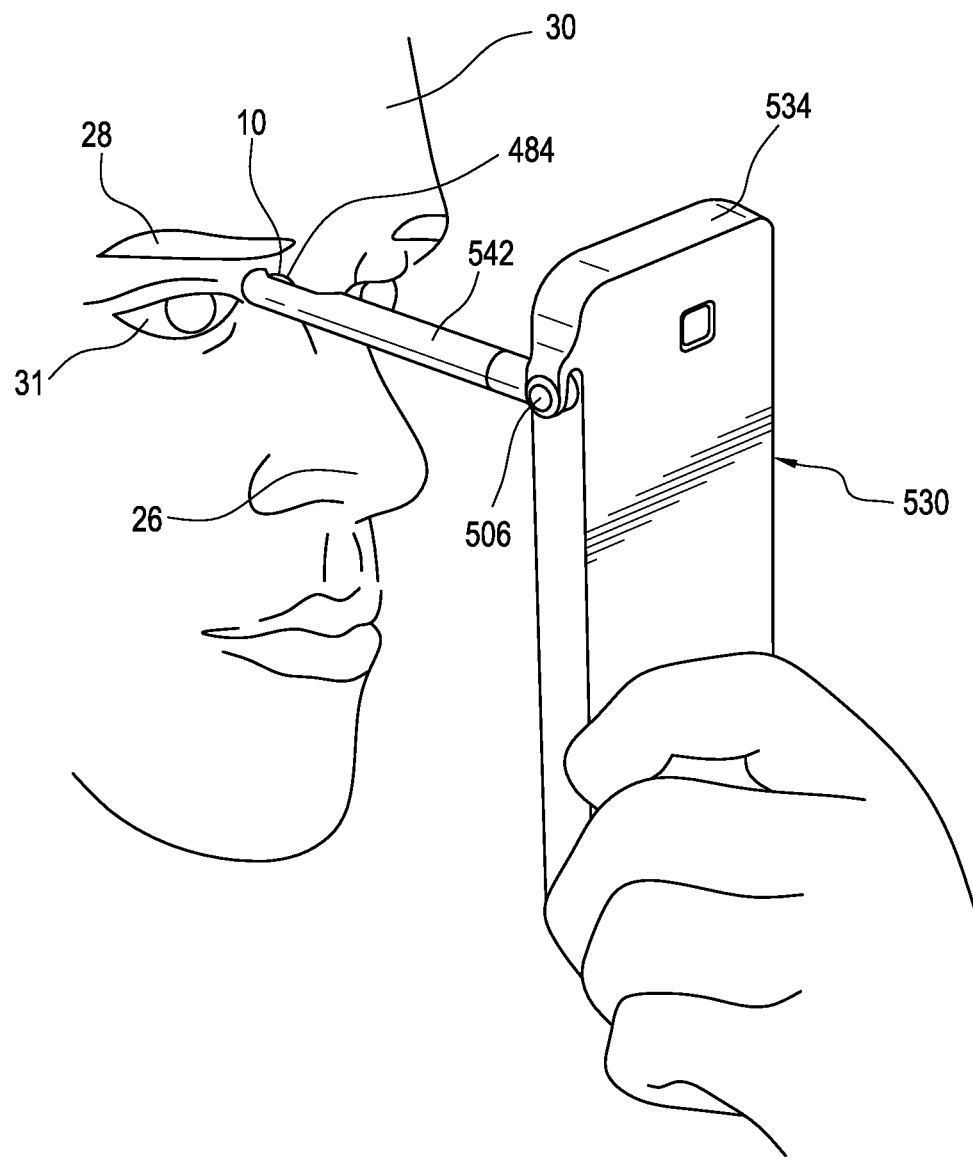
FIG. 65 shows a perspective view of the separable sensor device and electronic apparatus of FIG. 62 being operated by a user to read an emission from the ABTT.

FIGS. 63-65 show views of separable sensor device 530 with rod-like body 544 rotated to be approximately perpendicular to a planar front face 546 of electronic apparatus 532 to position and align sensor 484 with ABTT terminus 10.

FIGS. 66 to 74 show views of sensorial watches in accordance with exemplary embodiments of the present disclosure. Each sensorial watch includes a front face, a display positioned on the front fact, a back face, and a plurality of side faces extending from the front face to the back face.

Figures 66, 67:
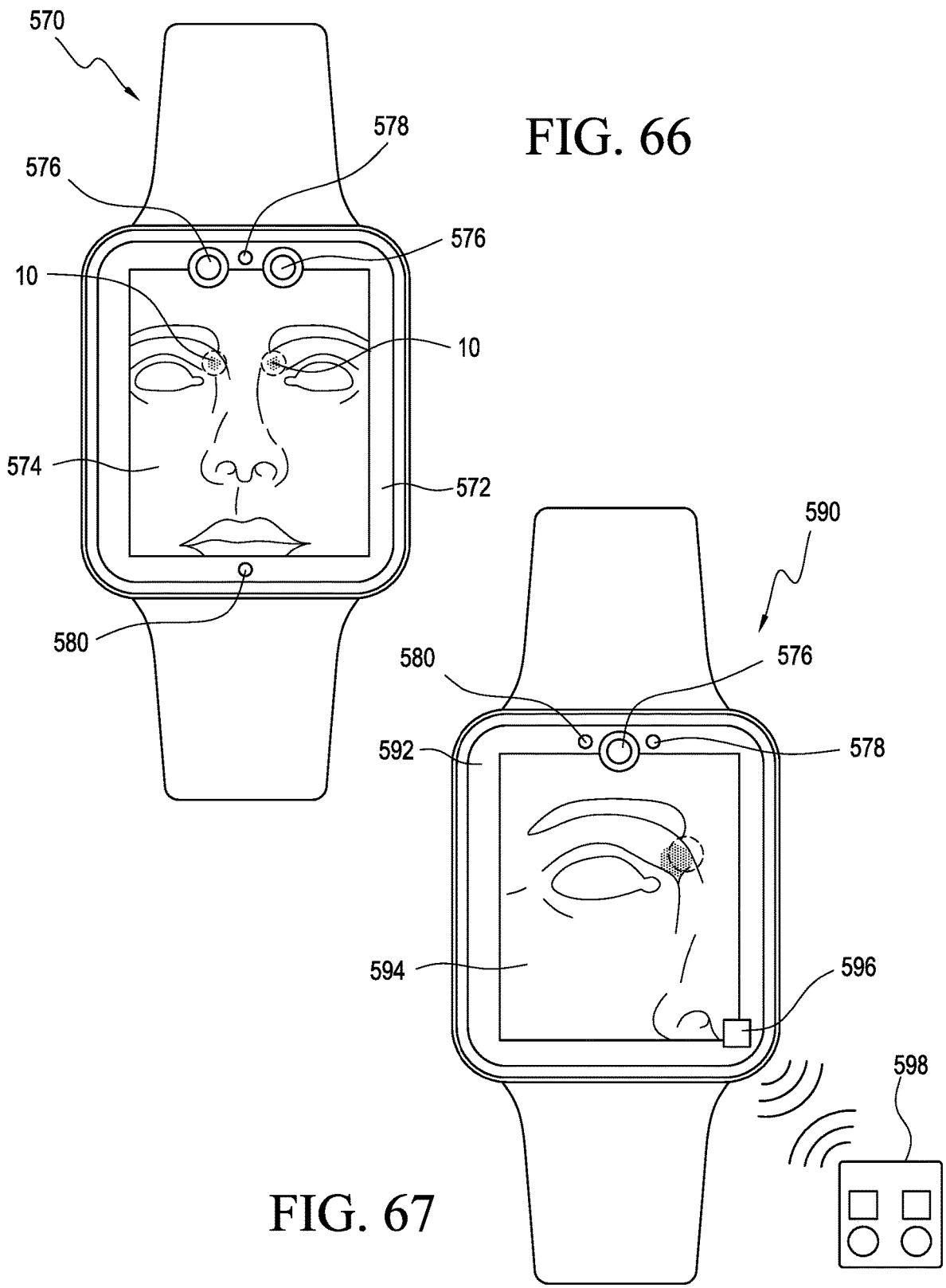
FIG. 66 shows a view of a watch including a measurement device in accordance with an exemplary embodiment of the present disclosure.
FIG. 67 shows a view of a watch including a measurement device in accordance with another exemplary embodiment of the present disclosure.

FIG. 66 shows a view of a sensorial watch, indicated generally at 570, including a measurement device in accordance with an exemplary embodiment of the present disclosure. Sensorial watch 570 includes front face 572, on which is positioned a display 574, a pair of side-by-side dual sensors or detectors 576 adjacent to display 574, a camera 578 disposed between sensors 576, and a cross-hair light source 580 for helping aligning sensors 576 with ABTT terminus 10. When elements similar or identical to the elements of FIG. 66 are used in subsequent figures, such similar or identical elements are labeled with the same item number as the elements of FIG. 66.

FIG. 67 shows a view of a sensorial watch, indicated generally at 590, including a measurement device in accordance with another exemplary embodiment of the present disclosure. Sensorial watch 570 includes front face 592, on which is positioned a display 594, one sensor 576, camera 578 disposed adjacent to sensor 576, cross-hair light source 580, and a wireless device, i.e., a transmitter or transceiver, communicatively or operatively coupled with an external or separate electronic device 598, including a cell phone, computer, tablet, or other electronic device.

Figure 68:
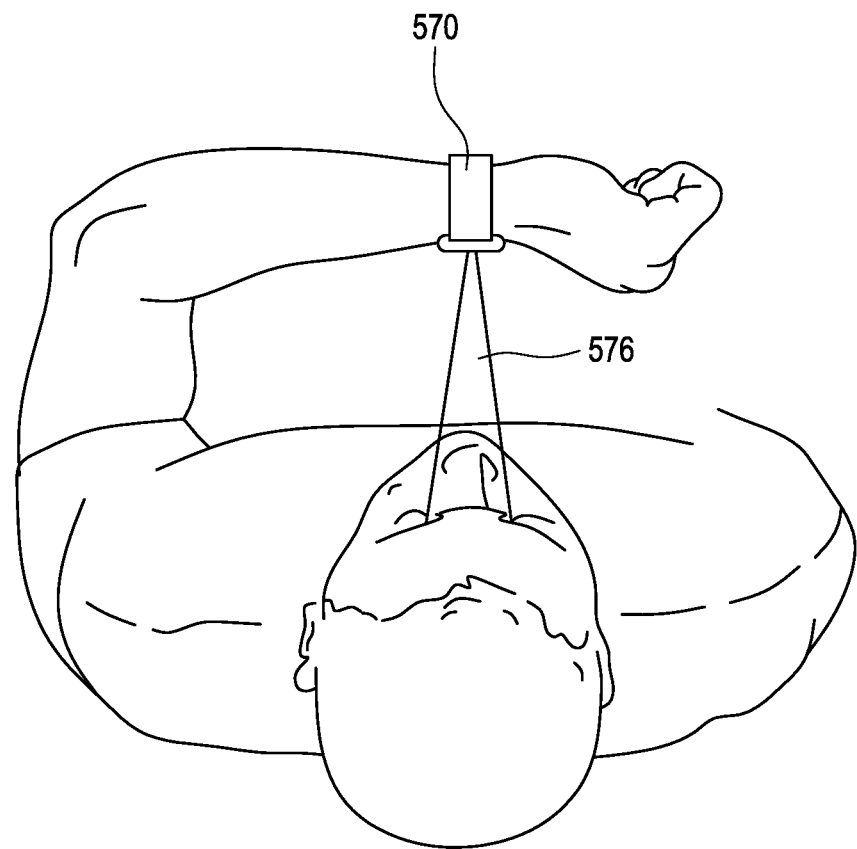
FIG. 68 shows a view of a user operating the watch of FIG. 66 to read an emission from the ABTT.

FIG. 68 depicts sensorial watch 570 being used by the subject to align a field of view of sensors 576 with ABTT terminus 10 and to then acquire signals from ABTT terminus 10.

Figure 69:
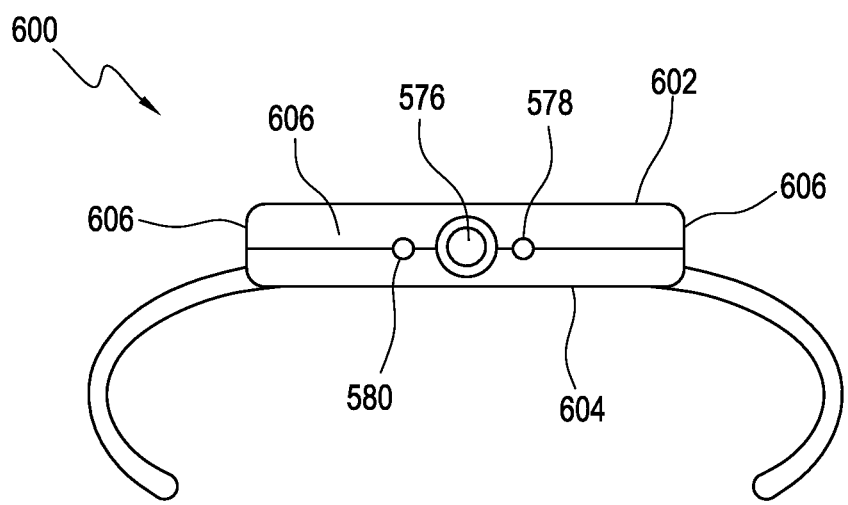
FIG. 69 shows a view a watch including a measurement device in accordance with yet another exemplary embodiment of the present disclosure.

FIG. 69 shows a view a sensorial watch, indicated generally at 600, including a measurement device in accordance with yet another exemplary embodiment of the present disclosure. Sensorial watch 600 includes a front face 602, a back face 604, and a plurality of side faces 606 extending from front face 602 to back face 604. Sensorial watch 600 includes sensor 576, camera 578 disposed adjacent to sensor 576, and cross-hair light source 580 positioned on one of side faces 606.

Figure 70:
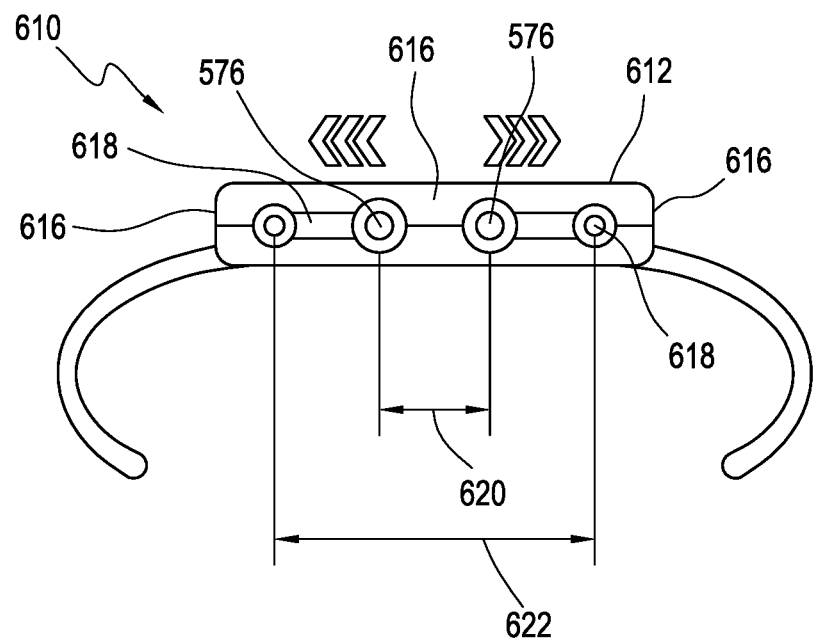
FIG. 70 shows a view of a watch including a measurement device in accordance with still another exemplary embodiment of the present disclosure.
Figure 71:
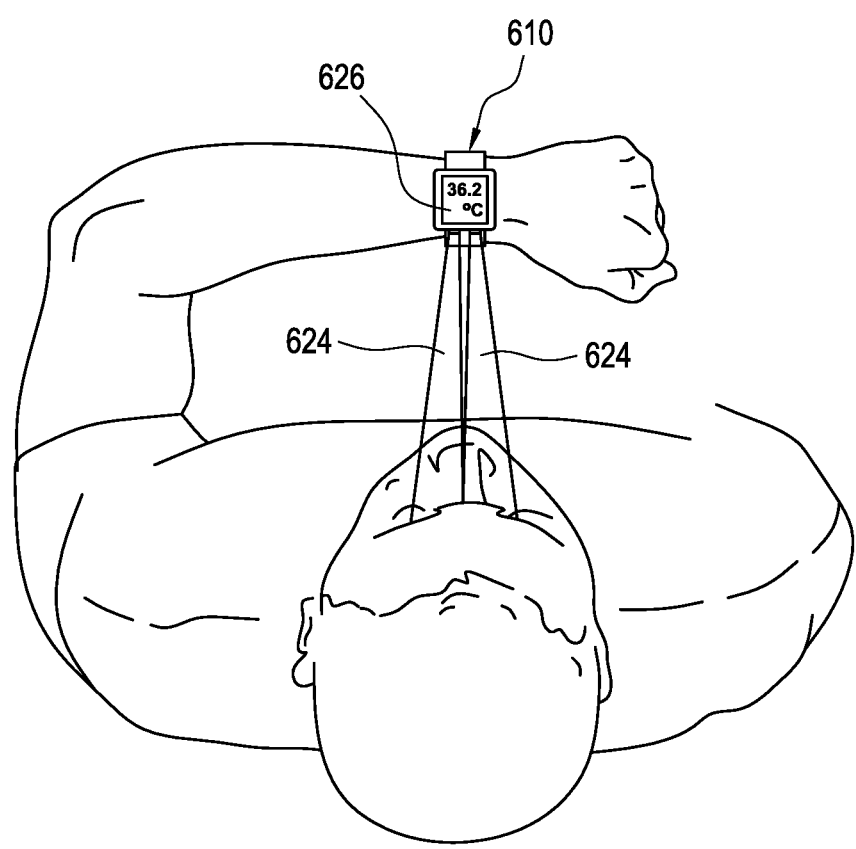
FIG. 71 shows a view of a user operating the watch of FIG. 71 to read an emission from the ABTT.

FIG. 70 shows a view of a sensorial watch, indicated generally at 610, including a measurement device in accordance with still another exemplary embodiment of the present disclosure. Sensorial watch 610 includes a front face 612, a back face 614, and a plurality of side faces 616 extending from front face 612 to back face 614. Sensorial watch 610 includes duel dual sensors or detectors 576 positioned on one of side faces 616, each sensor 576 is configured to be slidingly supported on sensorial watch 610 by a sliding mechanism 618. Sliding mechanism 618 is configured to adjusting a spaced distance between sensors 576 for alignment of sensors 576 with ABTT terminus 10. The space distance is configured to be in a range from a first, minimum spaced distance 620 to a maximum spaced distance 622. The actual dimensions of spaced distance 620 and spaced distance 622 depend on the longest dimension of side face 616 on which sensors 576 are positioned. FIG. 71 shows a view of the user operating sensorial watch 610 to position a field of view 624 of each sensor 576 to acquire signals from ABTT terminus 10, with measurement results being displayed on a display 626 positioned on front face 612.

Figure 72:
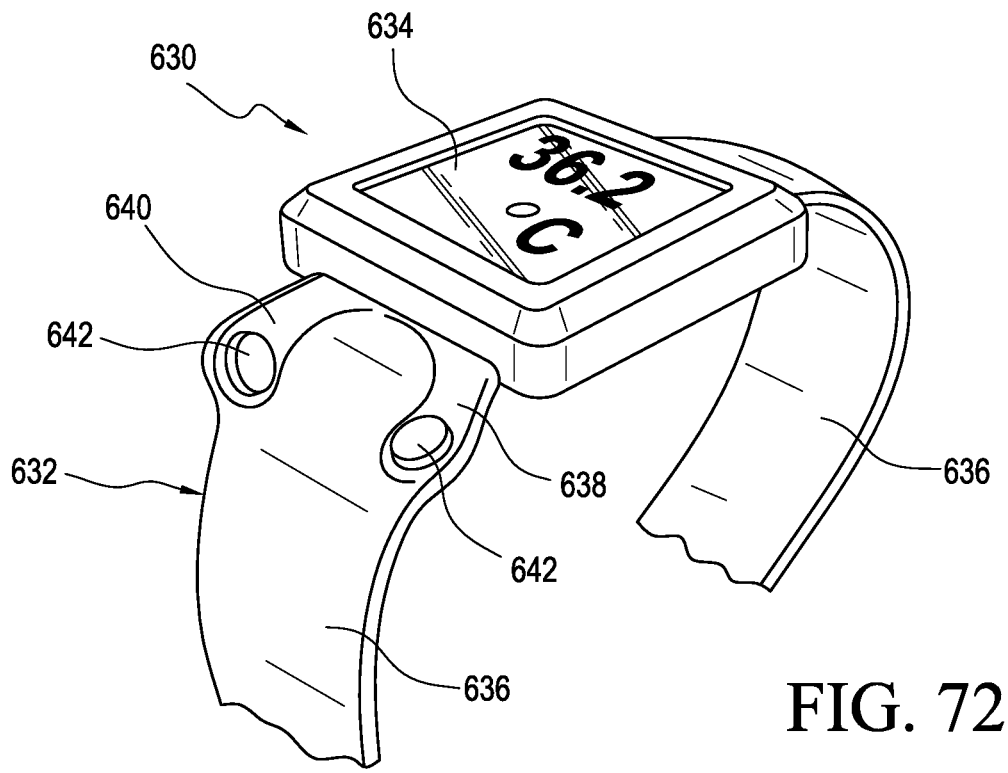
FIG. 72 shows a view of a watch including a measurement device in accordance with an even further exemplary embodiment of the present disclosure.
Figure 73:
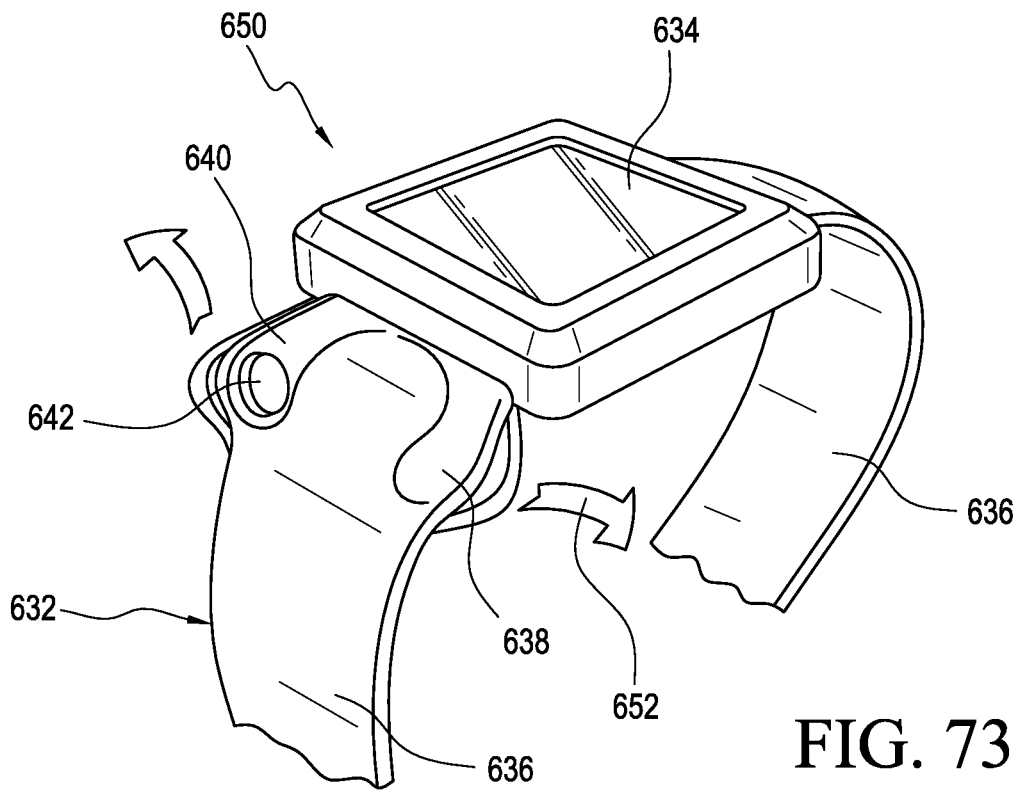
FIG. 73 shows a view of a watch including a measurement device in accordance with an even yet further exemplary embodiment of the present disclosure.
Figure 74:
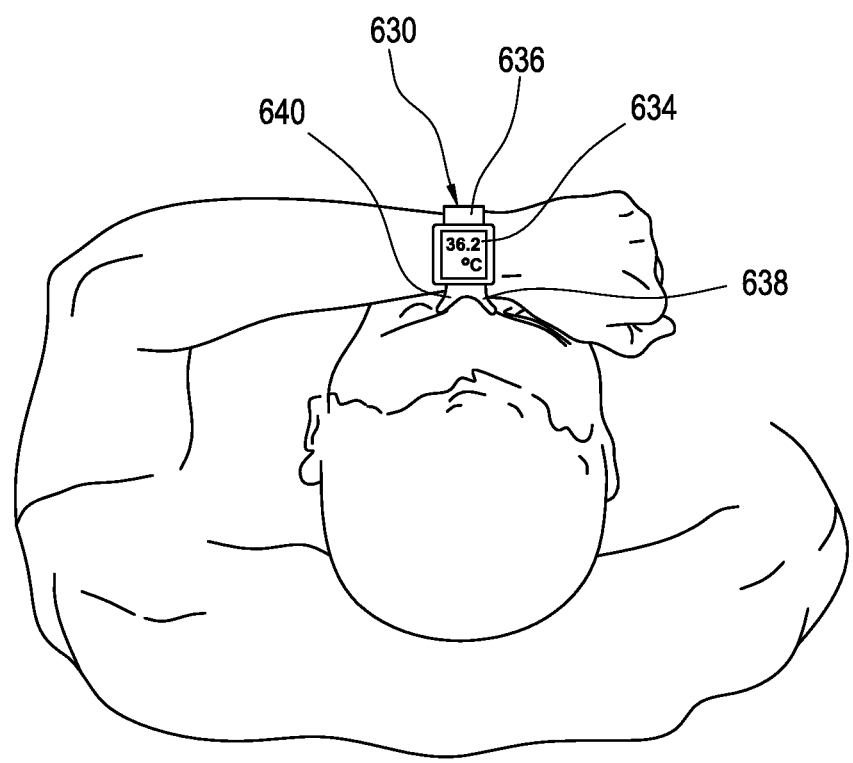
FIG. 74 shows a view of a user operating the watch of FIG. 72 to read an emission from the ABTT.

FIGS. 72 to 74 show sensorial wrist-bands having sensor assemblies and connected to a display and electronics. As with other embodiments herein, when similar or identical elements exist between embodiments, the same item number is used.

FIG. 72 shows a view of a watch, indicated generally at 630, including a measurement device in accordance with an even further exemplary embodiment of the present disclosure. Watch 630 includes a display 634 and a sensorial wrist-band 632 extending away from display 634 in two, generally opposite directions. Sensorial wrist-band 632 includes a strap 636, a first, right arm 638, and a second, left arm 640. Each of right arm 638 and left arm 640 include a sensor 642 disposed along a free end of right arm 638, and along a free end of left arm 640. Right arm 638 and left arm 640 are disposed adjacent to an edge of strap 636, beginning at a location that is adjacent to display 634. Right arm 638 and left arm 640 include a flexible and adjustable mechanism for adjusting right arm 638 and left arm 640 to different sizes of noses and for alignment with ABTT terminus 10. FIG. 74 shows watch 630 being operated by the user and positioned next to nose 26 of the face with sensors aligned with the ABTT. Although in FIG. 74 contact sensors are being used and are contacting the skin, it should be understood that non-contact sensors can be used in accordance to the principles of the disclosure in any of the embodiments showing contact sensors. It should be understood that contact sensors can be used in accordance to the principles of the disclosure in any of the embodiments using non-contact sensors. It should be understood that temperature modification devices can be used in accordance to the principles of the disclosure in any of the embodiments showing sensors.

FIG. 73 shows a view of a watch, indicated generally at 650, including a measurement device in accordance with an even yet further exemplary embodiment of the present disclosure. Watch 650 is similar to watch 630, though with only a single sensor 642. Further, the adjustability of first, right arm 638 and second, left arm 640 are shown by arrows 652. Right arm 640 is void of sensors and is used for positioning sensorial wrist-band 632 on nose 26.

Figure 75:
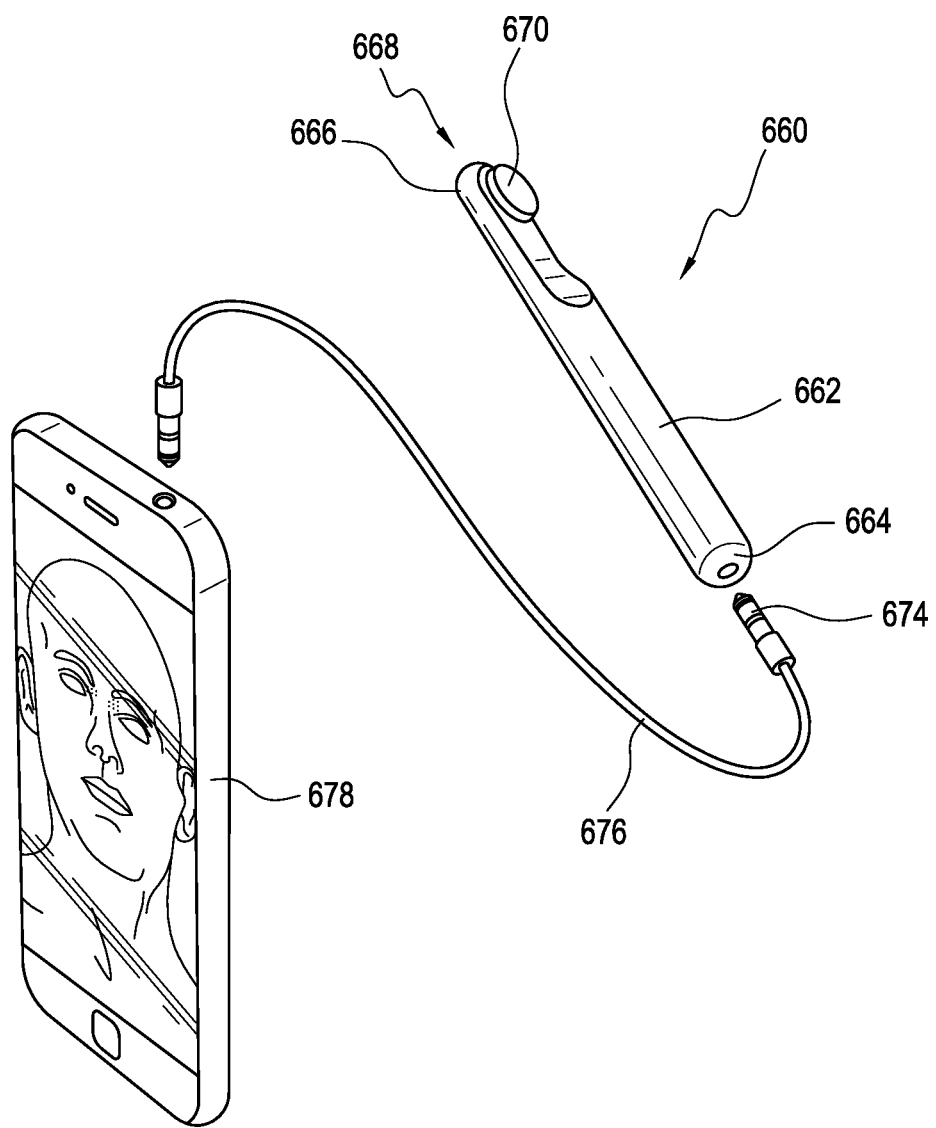
FIG. 75 shows a view of a sensor device in accordance with an exemplary embodiment of the present disclosure.

FIG. 75 shows a view of a sensor device, indicated generally at 660, in accordance with an exemplary embodiment of the present disclosure. Sensor device 660 includes a pen-shaped or essentially cylindrical-shaped body 662 including a proximate end 664 and a distal end 666. Distal end 666 includes a sensor head 668, which includes a sensor 670 disposed thereon. Proximate end 664 includes an electrical connector 672, which is configured to mate with a jack 674, which is connected to an electronic apparatus 678 by a cable or wire 676.

Figure 76:
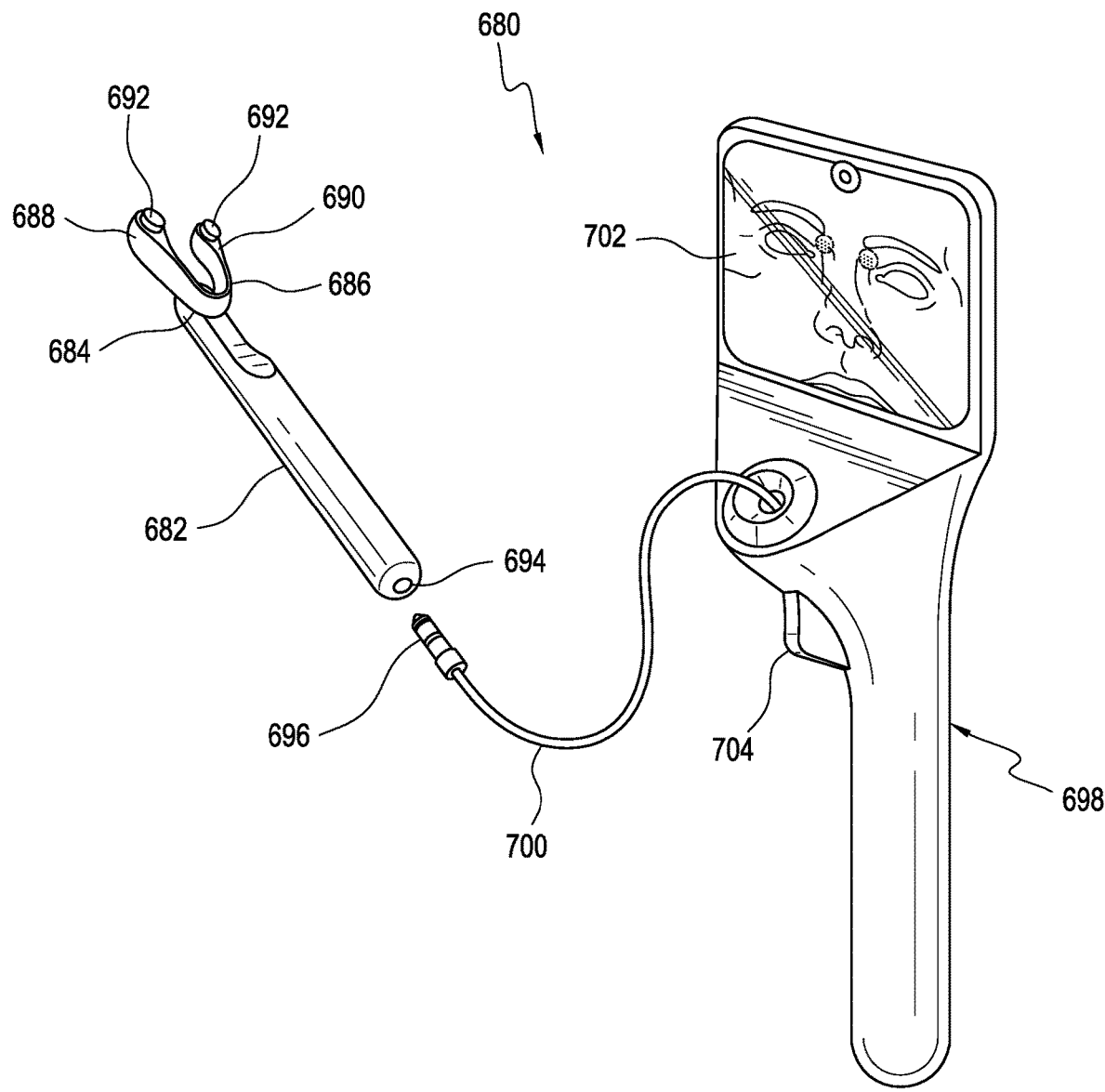
FIG. 76 shows a view of another sensor device in accordance with an exemplary embodiment of the present disclosure.

FIG. 76 shows a view of another sensor device, indicated generally at 680, in accordance with an exemplary embodiment of the present disclosure. Sensor device 680 includes a cylindrical or rod-like sensor body 682 on which is positioned a sensor head 684 at a distal end thereof. Sensor head 684 includes a two prong support 686 that includes a right arm 690 and a left arm 688, with each arm including a sensor 692 positioned on a free end thereof. Sensor body 682 also includes an electrical connector 694 configured to accept a jack or connector 696, which is connected to an electronic apparatus 698 by way of a cable or wire 700. Electronic apparatus 698 includes a display 702 and a trigger button 704 for actuating sensor device 680. It should be understood that sensor body 682 can be connected to any electronic device or thermometer configured to read the signals from sensors 692 and to report the signals sensors 692.

Figure 77:
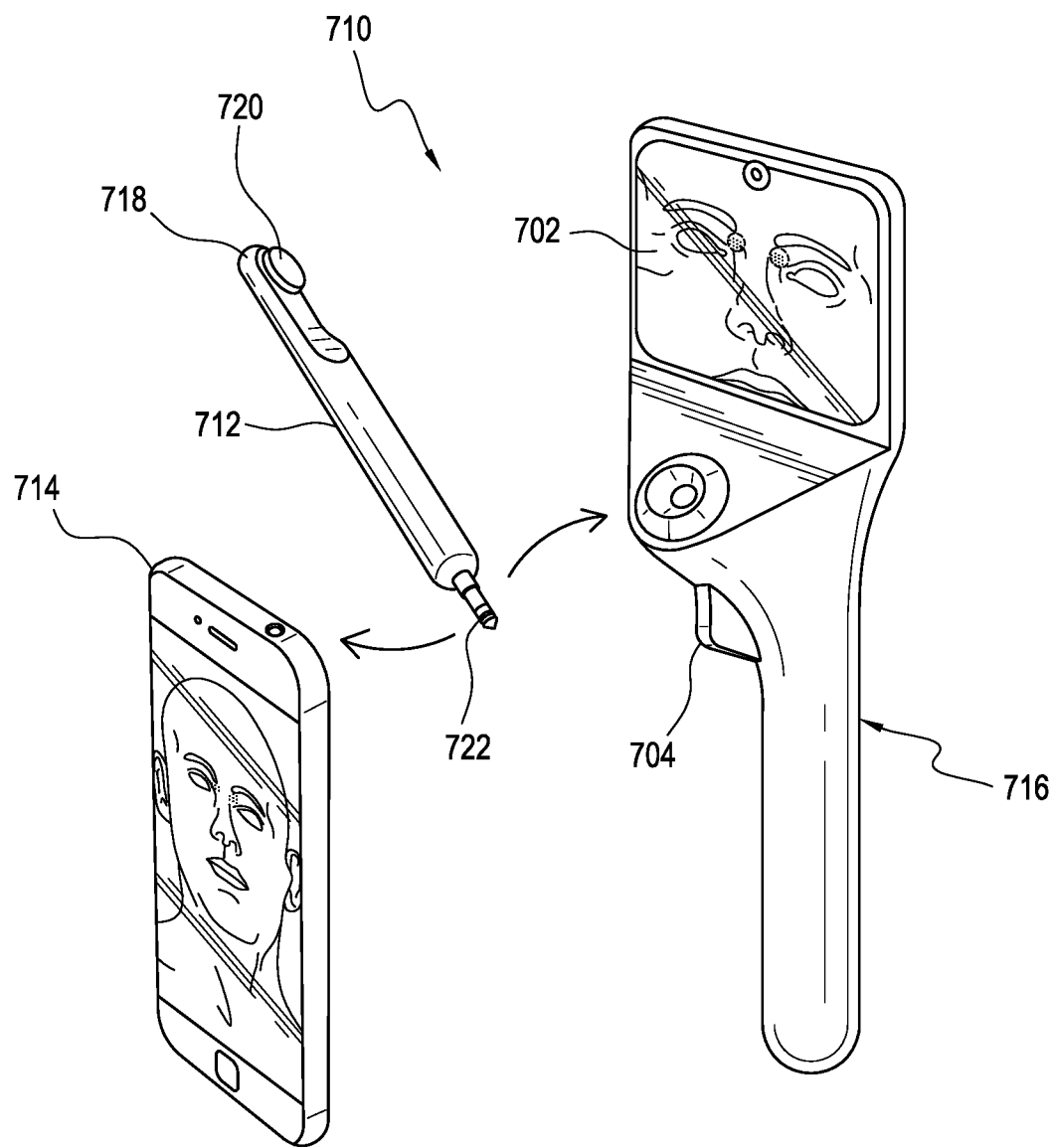
FIG. 77 shows a view of yet another sensor device in accordance with an exemplary embodiment of the present disclosure.

FIG. 77 shows a view of yet another sensor device, indicated generally at 710, in accordance with an exemplary embodiment of the present disclosure. Sensor device 710 is similar in some respects to the embodiment of FIG. 76, and such similar elements are labeled with the same element number. Sensor device 710 includes a cylindrical, rod-like, tubular, or pen-shaped sensor body 712 and an electronic apparatus 714, for example a cell phone, or a specialized electronic apparatus 716. Sensor body 712 includes a sensor head 718 at a distal end on which is positioned a sensor 720 at a free end thereof. Sensor body 712 also includes an electrical connector 722 positioned at a proximate end. Connector 722 is configured to connect to electronic apparatus 714 and to electronic apparatus 716.

Figure 78:
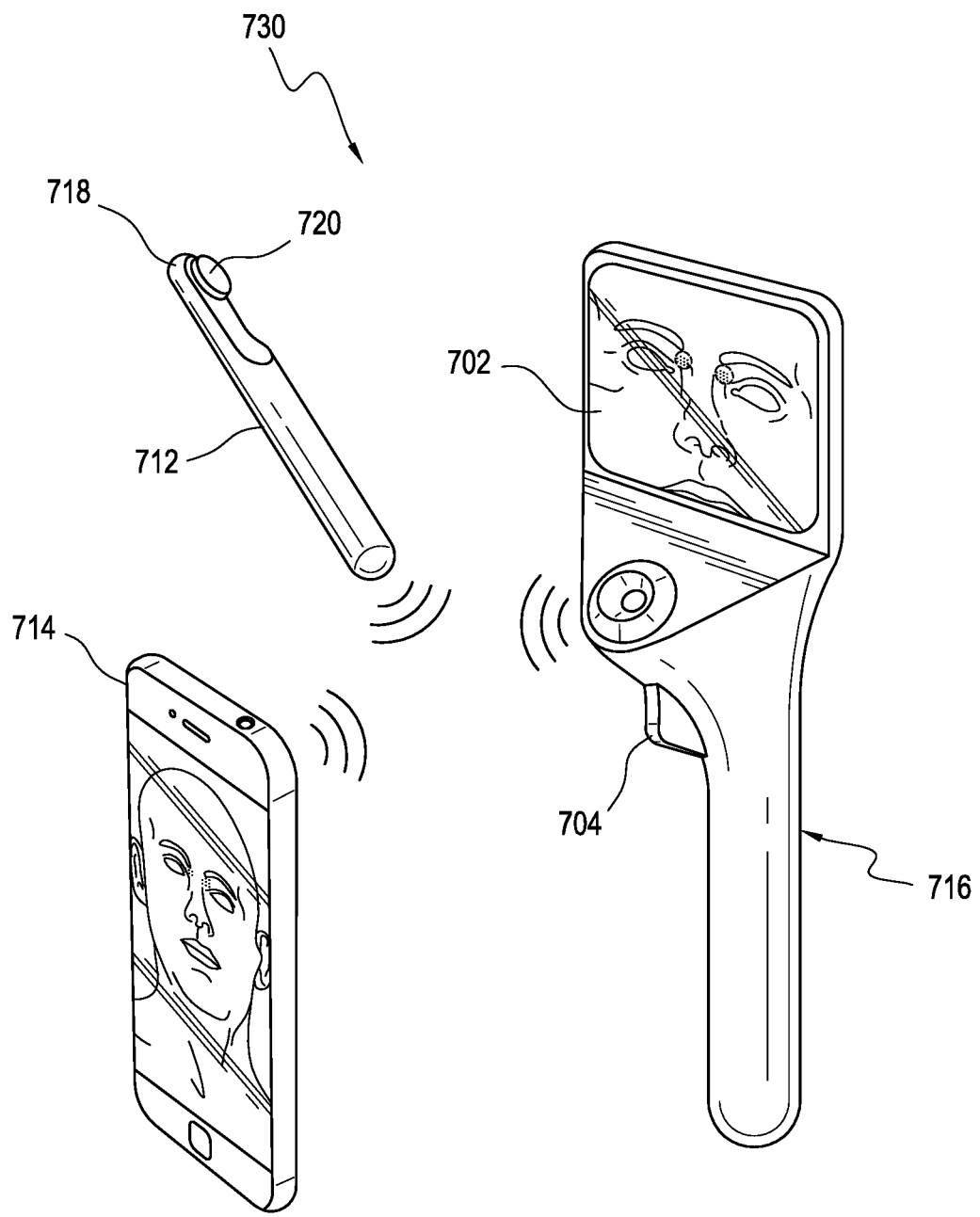
FIG. 78 shows a view of a further sensor device in accordance with an exemplary embodiment of the present disclosure.

FIG. 78 shows a view of a further sensor device, indicated generally at 730, in accordance with an exemplary embodiment of the present disclosure. Sensor device 730 is similar to the embodiments of FIGS. 76 and 77, but communication with electronic apparatus 714 and electronic apparatus 716 is by way of a transmitter.

Figure 79:
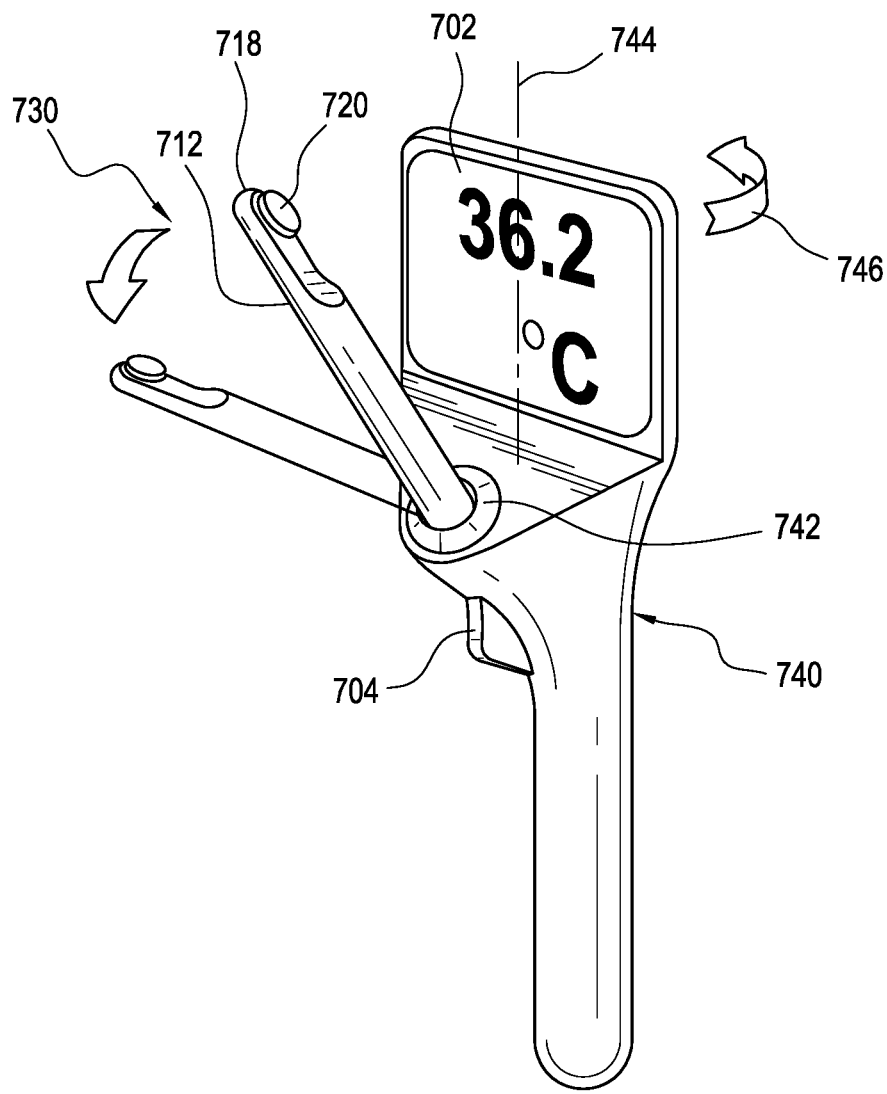
FIG. 79 shows the sensor device of FIG. 77 connected to an electronic apparatus in accordance with an exemplary embodiment of the present disclosure.
Figure 80:
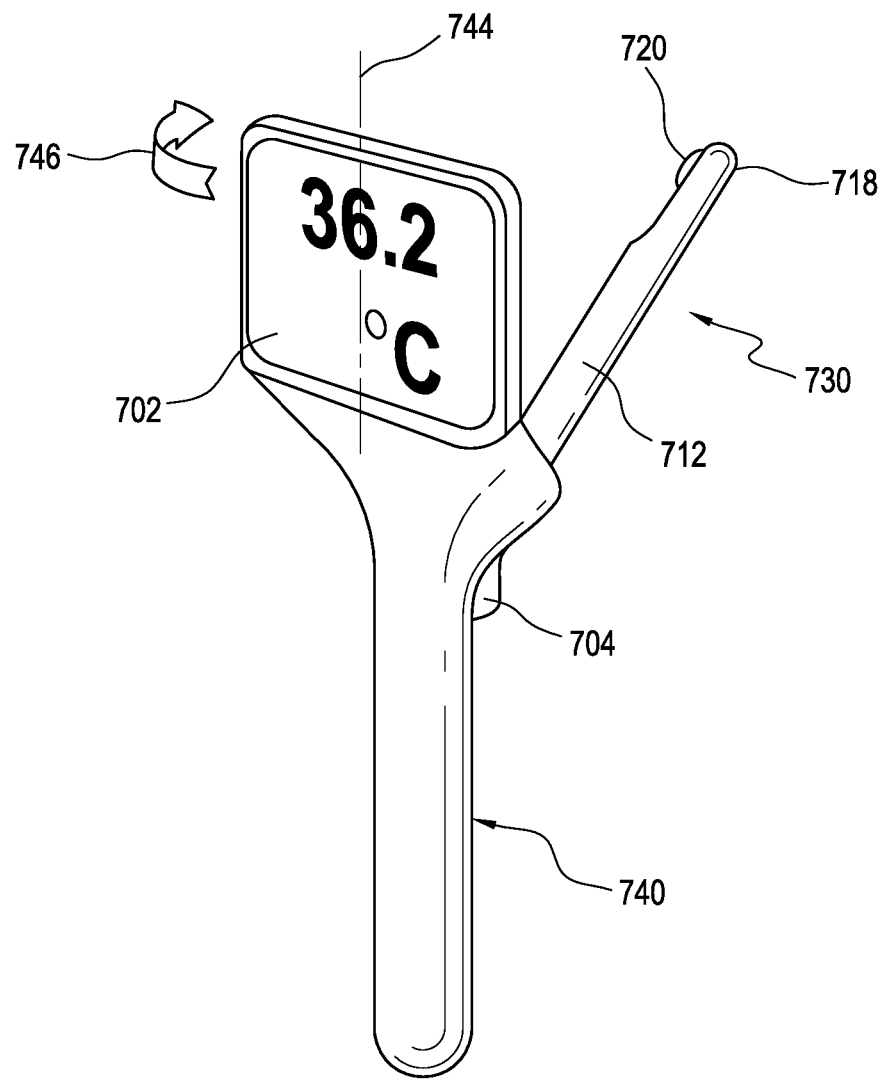
FIG. 80 shows a view of a view of a rotating mechanism of a display compatible with the sensor devices of FIGS. 76-79 in accordance with an exemplary embodiment of the present disclosure.
Figure 81:
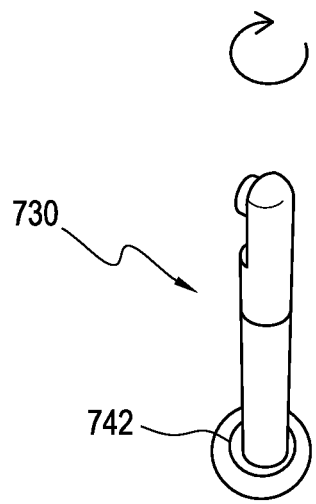
FIG. 81 shows a first view of a rotating mechanism of the device of FIG. 79.
Figure 82:
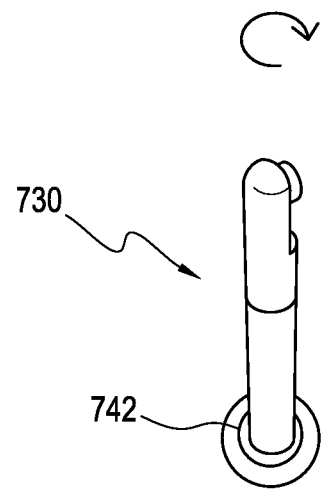
FIG. 82 shows a second view of a rotating mechanism of the device of FIG. 79.
Figure 83:
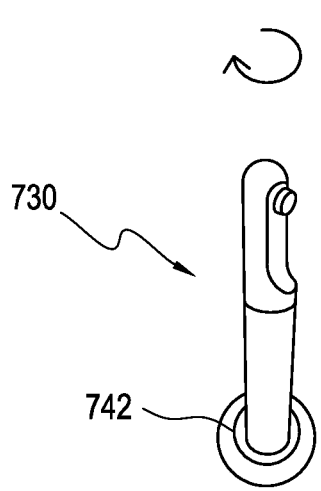
FIG. 83 shows a third view of a rotating mechanism of the device of FIG. 79.
Figure 84:
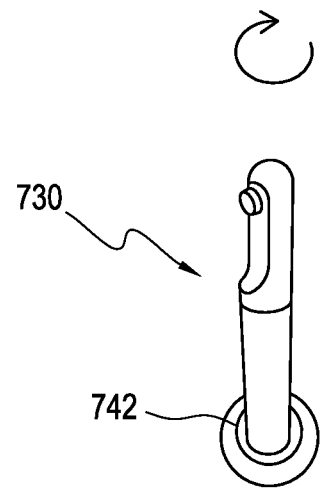
FIG. 84 shows a fourth view of a rotating mechanism of the device of FIG. 79.

FIG. 79 shows sensor device 730 connected to an electronic apparatus, indicated at 740, in accordance with an exemplary embodiment of the present disclosure. Electronic apparatus 740 includes display 702 and is configured to read signal from sensor device 730. Electronic apparatus 740 includes an electrical connector 742 configured with an up and down rotating mechanism to align sensor 720 with ABTT terminus 10. Display 702 is also rotatable about an axis 744, as shown by arrow 746. FIG. 80 shows display 702 rotated by 180 degrees about axis 744 allowing thereby another person, such as doctor, to see the result on display 702. FIGS. 81 to 84 show a plurality of exemplary orientations of sensor device 730 as it rotates about its own axis while positioned in connector 742.

FIG. 85 shows a view of a rotating mechanism, indicated at 752, of a sensor device, indicated generally at 750, in accordance with an exemplary embodiment of the present disclosure. Sensor device 750 includes a sensor body 754 and a sensor head 756 supporting a sensor 758. Sensor head 756 is connected to sensor body 754 by rotating mechanism 752, which permits sensor head 756 to rotate about an axis 760 that is perpendicular to a longitudinal axis 762 of sensor body 754 to permit sensor head 756 to be oriented in a plurality of positions, as exemplified by the positions shown in FIG. 85. Rotating mechanism 752 is configured to adjust the position of sensor head 756 to provide an optimal position of sensor 758 for measurement of ABTT terminus 10.

Figure 87:
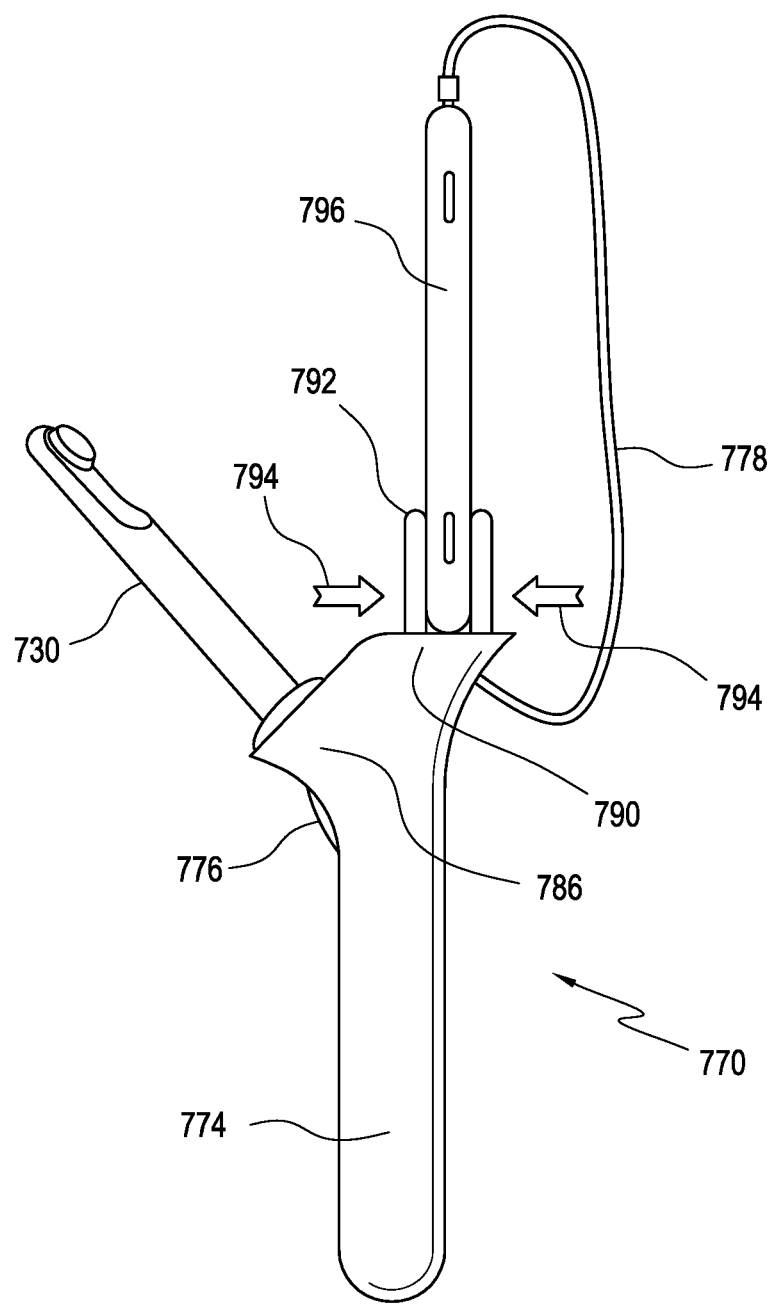
FIG. 87 shows another view of the support structure of FIG. 86.
Figure 89:
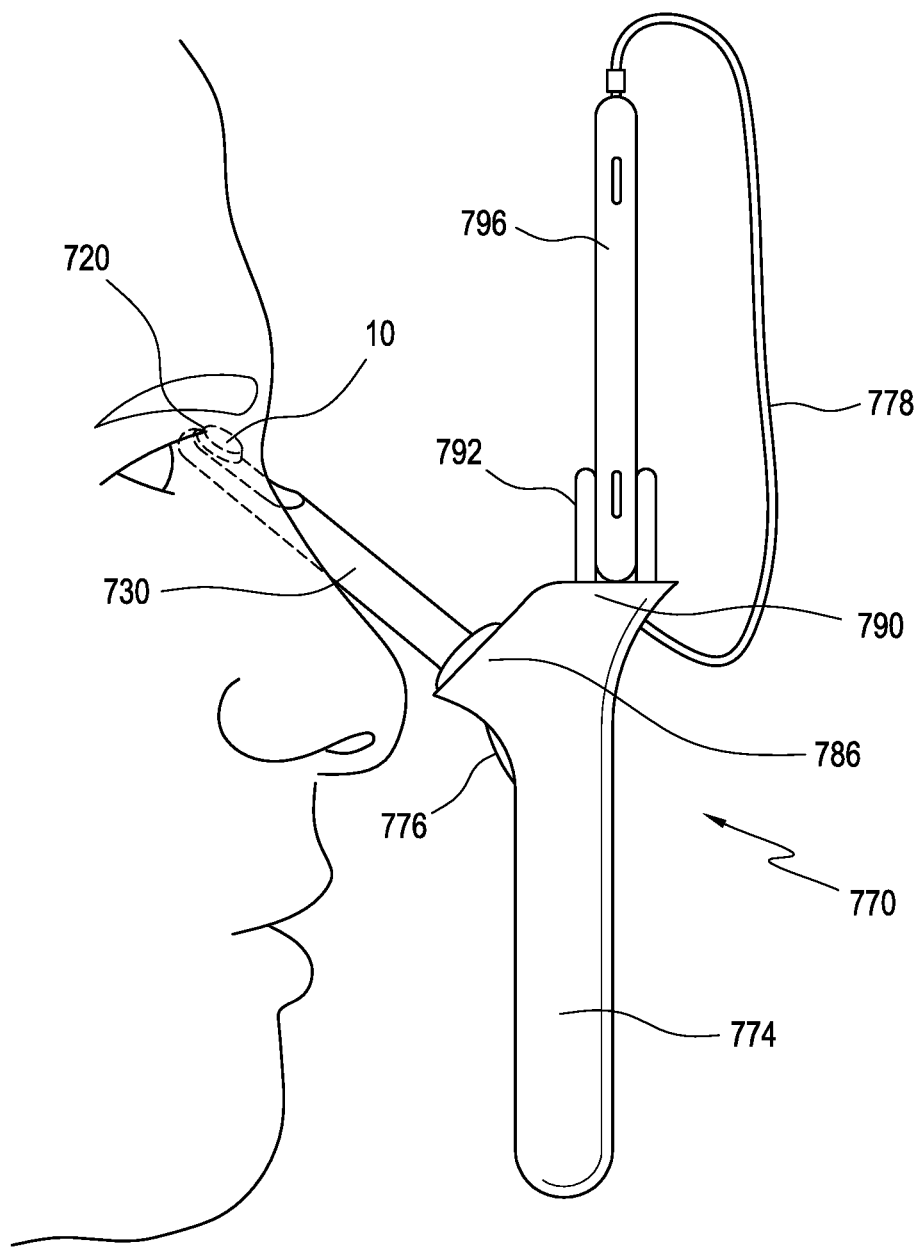
FIG. 89 shows another view of the support structure of FIGS. 86 and 87.

FIGS. 86 and 87 show view of a support structure, indicated generally at 770, in accordance with an exemplary embodiment of the present disclosure. Support structure 770 includes a housing 772 that further includes three portions. One portion includes a handle 774 that includes an operation or actuation button 776, and a cable 778 including an electrical connector or jack 778 configured to fit a mating connector of an electronic apparatus. Another portion is a mid-portion 786 that includes an electrical connector 788 configured to receive a distal end of sensor device, such as sensor device 730. Yet another portion is an upper portion 790 that includes a clamp mechanism 792 configured to secure an electronic apparatus body. Clamp mechanism 792 is configured to extend in the direction of arrows 794 to receive a plurality of dimensions of an electronic apparatus 796. Although for illustration purposes cable 778 for connection with the electronic apparatus is shown, it should be understood that an internal electrical connection can be disposed along a bottom of clamp mechanism 792 and configured to receive a complementary electrical connection of an electronic apparatus, and such embodiment is within the scope of the disclosure. FIG. 89 shows sensor device 730 positioned to align sensor 670 with ABTT terminus 10.

Figure 88:
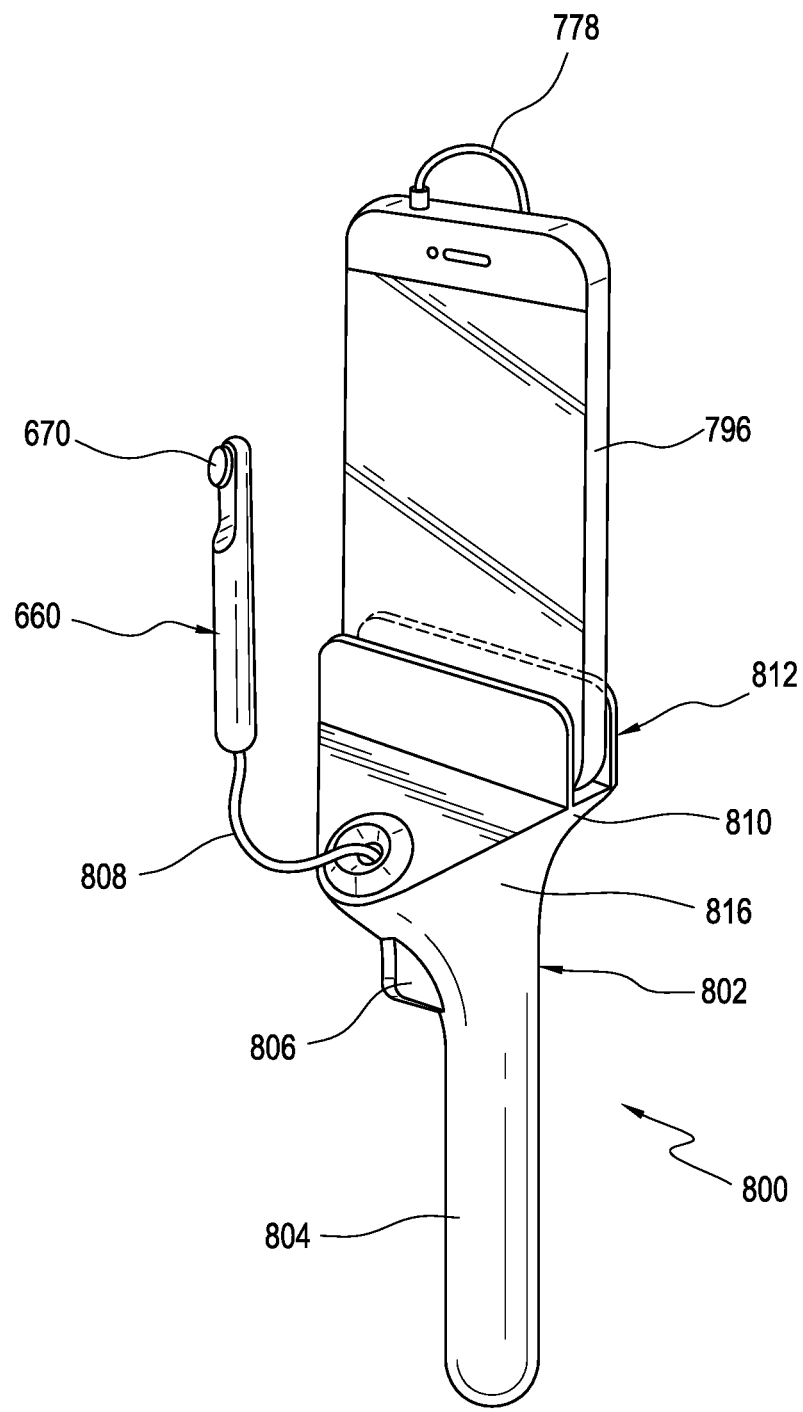
FIG. 88 shows a view of another support structure in accordance with an exemplary embodiment of the present disclosure.

FIG. 88 shows a view of another support structure, indicated generally at 800, in accordance with an exemplary embodiment of the present disclosure. Support structure 800 includes a housing 802 that includes a handle 804, an actuation button 806, an upper portion 810 including a clamp mechanism 812, and a mid-portion 816. Mid-portion 816 includes an extendable/retractable wire or cable 808 for connection to a sensor device, such as sensor device 660.

Figure 90:
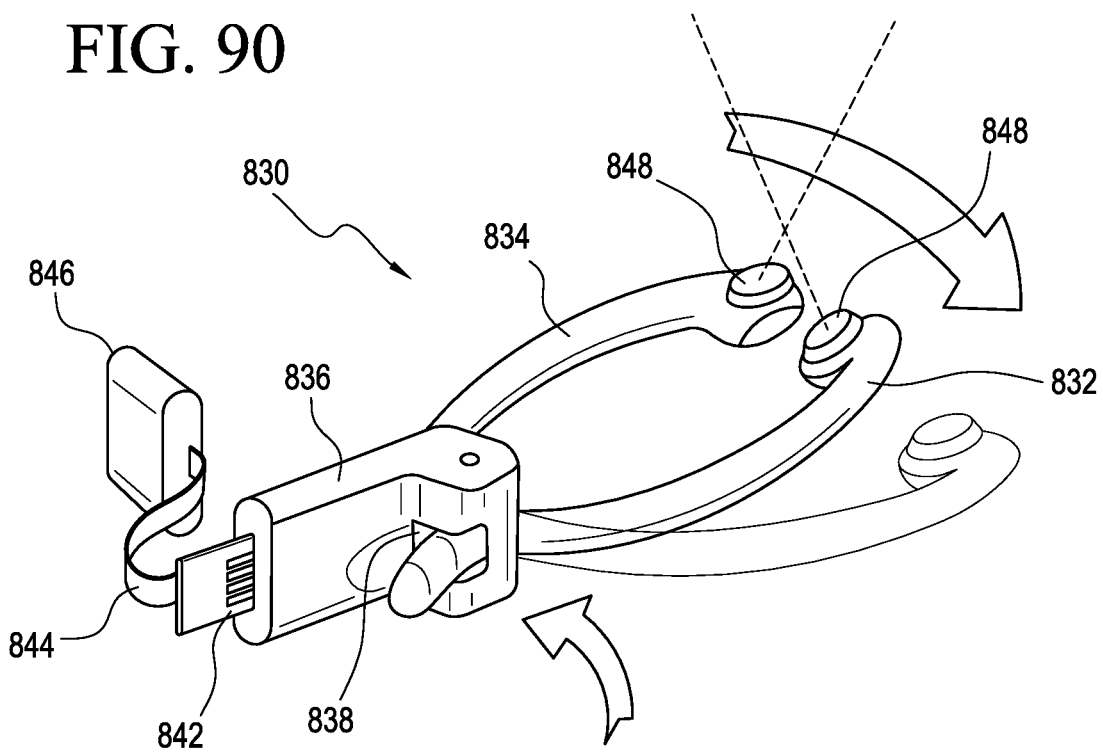
FIG. 90 shows a view of a sensor clip assembly in accordance with an exemplary embodiment of the present disclosure.

FIG. 90 shows a view of a sensor clip assembly, indicated generally at 830, in accordance with an exemplary embodiment of the present disclosure. Sensor clip assembly 830 includes a rotatable right arm 832, a rotatable left arm 834, a housing 836 in which is positioned a spring mechanism 838 that biases or pushes right arm 832 and said left arm 834 toward or against each other, and a lever or handle 840 that is connected to right arm 832 and which moves right arm 832 away from left arm 834 when pressed or pushed. Sensor clip assembly 830 also includes an electrical connector 842, and a cable 844 that extends from electrical connector 842 and which terminates at an electrical connector 846. Each of right arm 832 and left arm 834 includes a sensor 848 disposed at a free end of the respective right arm 832 and left arm 834.

Figure 91:
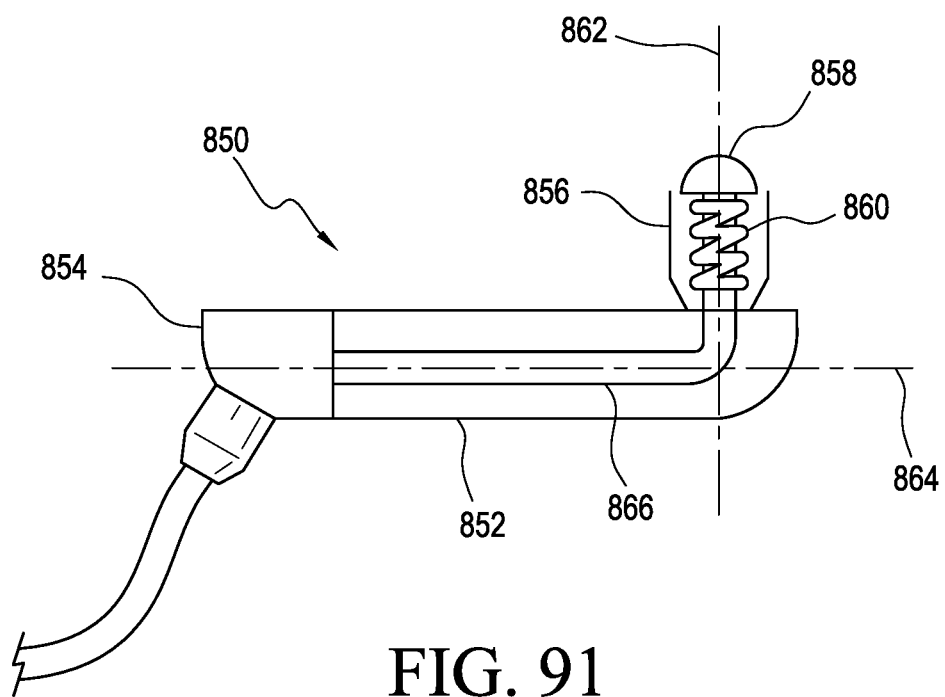
FIG. 91 shows a view of a sensor head in accordance with an exemplary embodiment of the present disclosure.

FIG. 91 shows a view of a sensor head, indicated generally at 850, in accordance with an exemplary embodiment of the present disclosure. Sensor head 850 includes a sensor body 852, a connection portion 854, and a contact sensor portion 856. Contact sensor portion 856 includes a contact sensor 858 and a spring mechanism 860 disposed along an axis 862 that is approximately perpendicular to a main longitudinal axis 864 of sensor body 852. Sensor head 850 further includes wires 866 extending along sensor body 852 to connect contact sensor 858 to connection portion 854.

Figure 92:
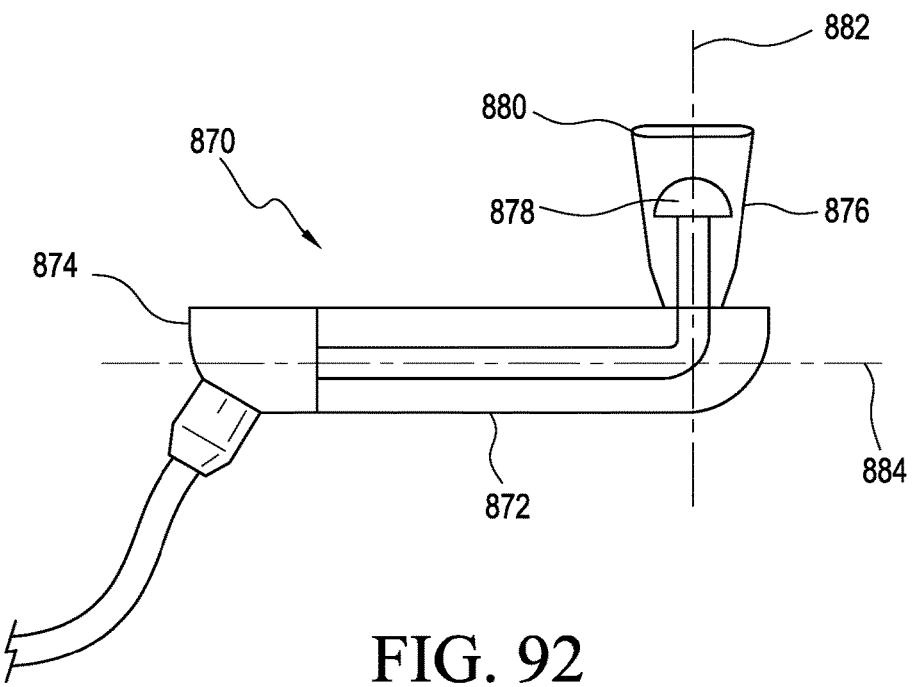
FIG. 92 shows a view of sensor head in accordance with another exemplary embodiment of the present disclosure.

FIG. 92 shows a view of sensor head, indicated generally at 870, in accordance with another exemplary embodiment of the present disclosure. Sensor head 870 includes a sensor body 872, a connection portion 874, and a non-contact sensor portion 876. Non-contact sensor portion 876 includes a non-contact sensor 878 position within a sensor housing 880 that is disposed along an axis 882 that is approximately perpendicular to a main longitudinal axis 884 of sensor body 872. Sensor head 870 further includes wires 886 extending along sensor body 872 to connect non-contact sensor 878 to connection portion 874. Sensor housing 880 protects non-contact sensor 878, such as an infrared sensor, against interference by surrounding ambient temperature and sweat.

Figure 93:
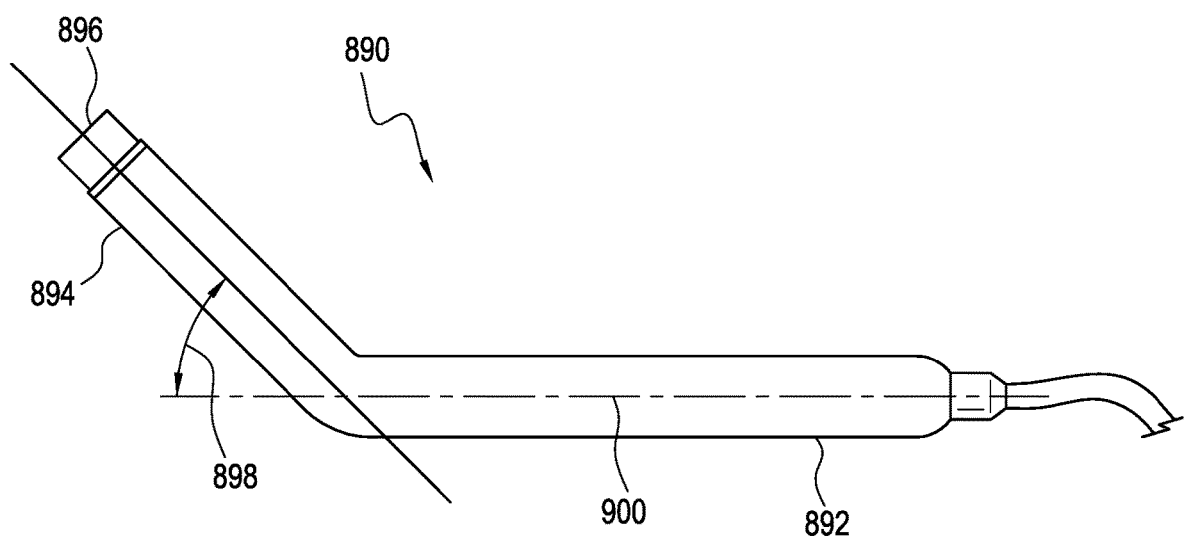
FIG. 93 shows a view of a thermometer in accordance with an exemplary embodiment of the present disclosure.

FIGS. 93 and 94 show views of a thermometer, indicated generally at 890, in accordance with an exemplary embodiment of the present disclosure. Thermometer 890 includes a handle 892 and a sensor head 894. Sensor head 894 includes a sensor 896 positioned thereon. Handle 892 is positioned or disposed at an angle 898 that is optimally 45 degrees in relation to handle axis 900. Angle 898 is preferably in the range from 10 degrees to 80 degrees, is more in the range of 15 degrees to 75 degrees, is even more preferably in the range of 30 degrees to 60 degrees, and is most preferably in the range of 40 degrees to 50 degrees. The optimal 45 degree angle allows sensor 896 to be aligned with ABTT terminus 10 when handle 892 is parallel to a plane 902 of the face or when handle 892 is positioned perpendicular to facial plane 902, as shown in FIG. 94, which shows thermometer 890 being used by the subject.

Figure 97:
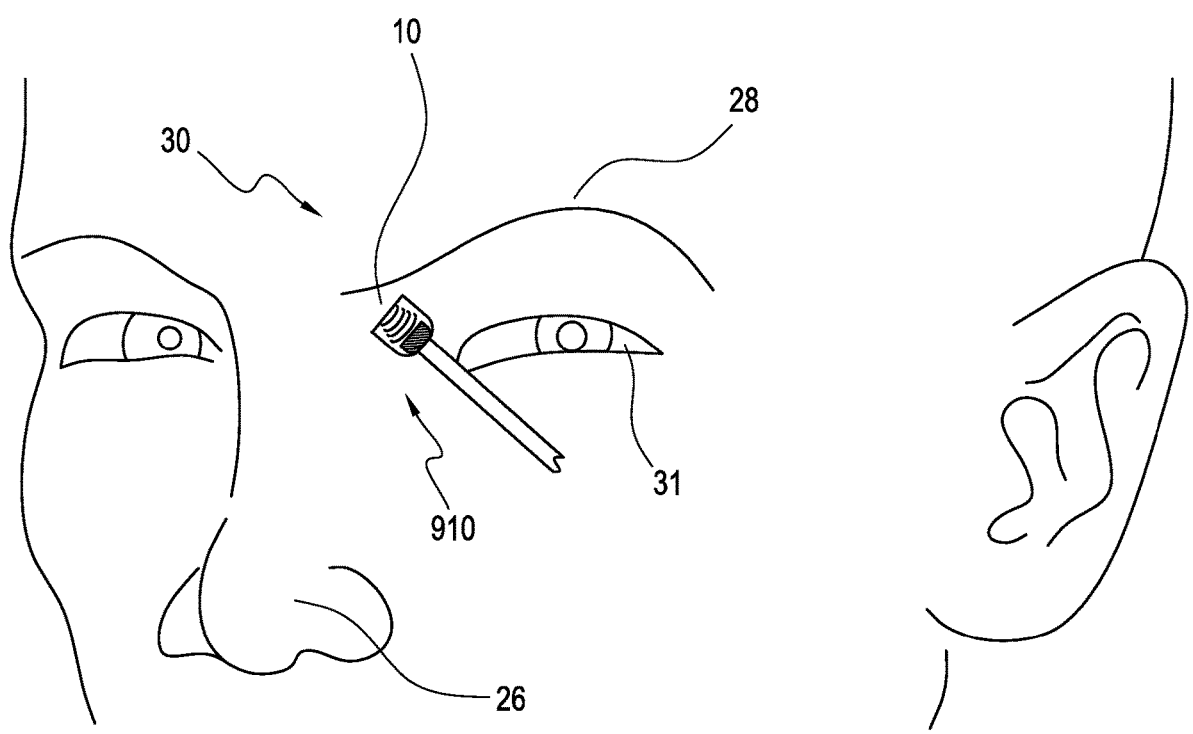
FIG. 97 shows a further view of the sensor head of FIG. 95.
Figure 98:
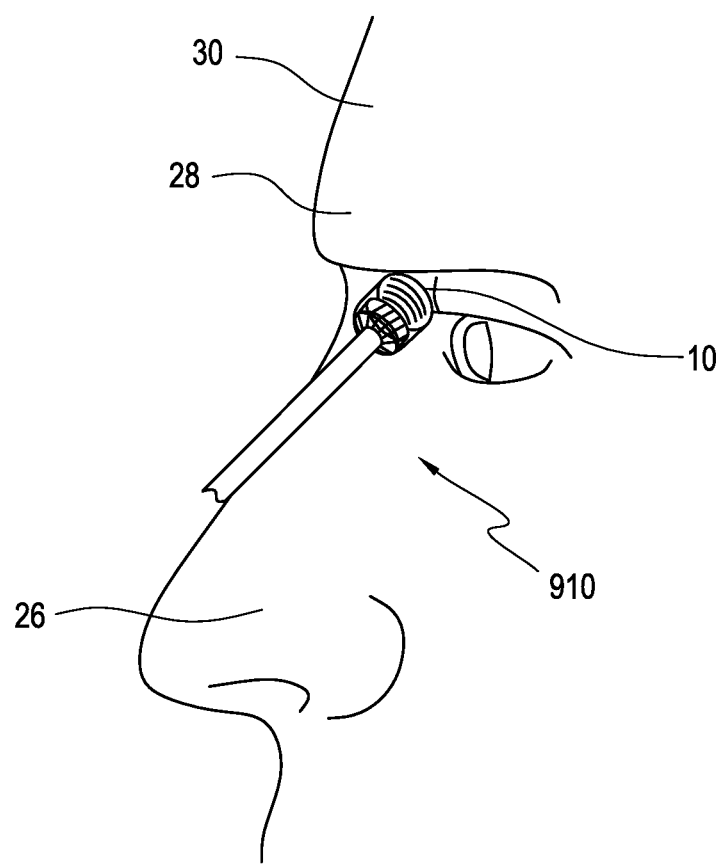
FIG. 98 shows an even further view of the sensor head of FIG. 95.

FIGS. 95 and 96 show views of a sensor head, indicated generally at 910, in accordance with an exemplary embodiment of the present disclosure. Sensor head 910 includes a sensor 912 and a housing 914 that surrounds sensor 912 and includes an open end 916 surrounding sensor 912, and a connecting arm 918. FIG. 96 shows sensor head 910 positioned on skin 920 and receiving radiation from skin 920. Housing 914 with open end 916 creates a confined and protected environment (volume 922) for radiation 924 from skin 920. FIGS. 97 and 98 show sensor head 910 being used by the subject and aligned in a diagonal angle of approximately 45 degrees with ABTT terminus 10. It should be understood that embodiments of FIGS. 91-98 can be used with any of the sensor devices and temperature modification devices described in the present disclosure.

Figure 99:
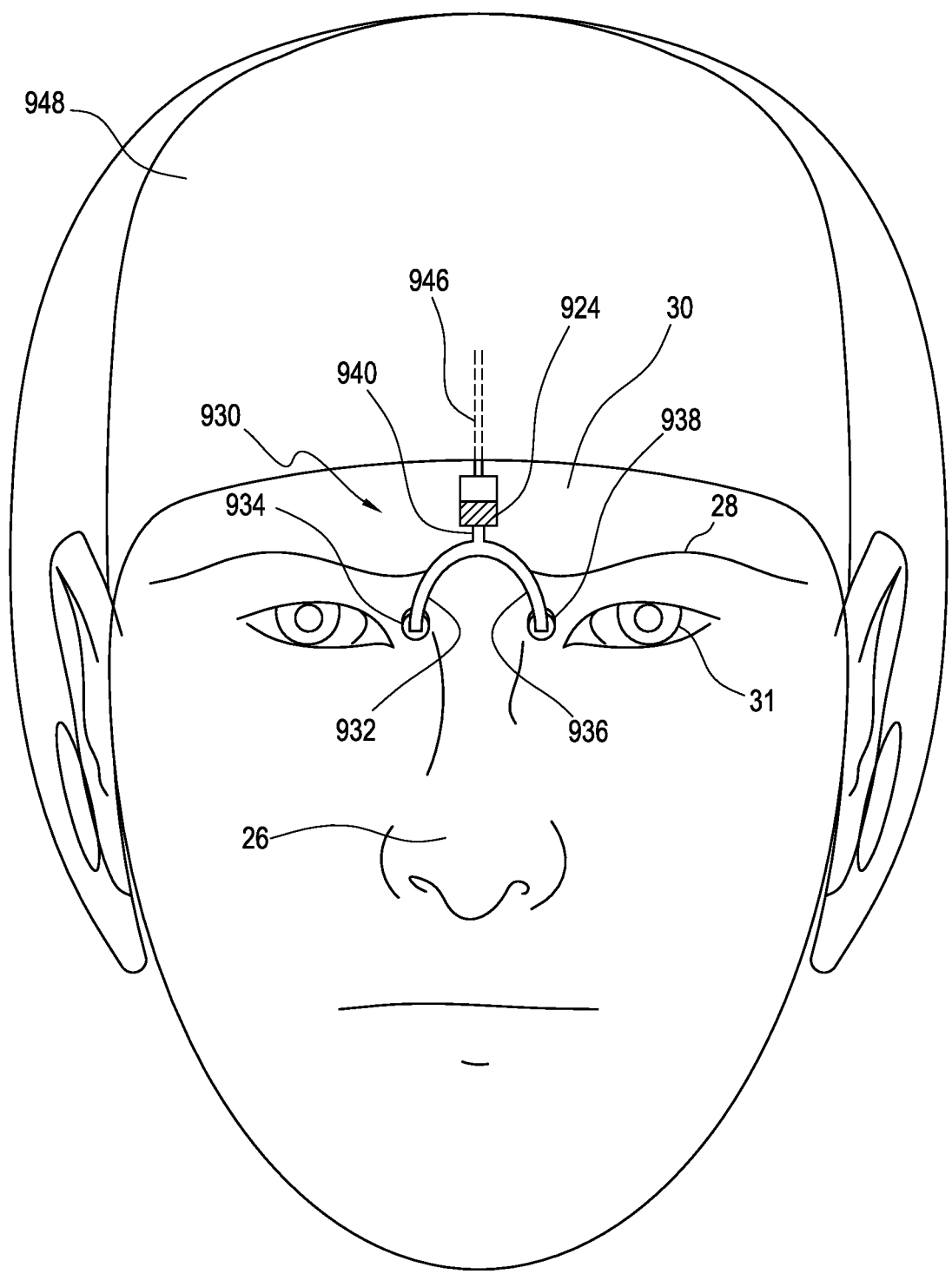
FIG. 99 shows a sensor device in accordance with an exemplary embodiment of the present disclosure.

FIG. 99 shows a sensor device, indicated generally at 930, in accordance with an exemplary embodiment of the present disclosure. Sensor device 930 includes a right arm 932, a right sensor 934 positioned at a free end of right arm 932, a left arm 936, a left sensor 938 positioned at a free end of left arm 936, and a vertical support arm 940. Vertical support arm 940 is preferably rigid and is configured to connect to right arm 932 and left arm 936 at a first end of vertical support arm 940. A second end of vertical support arm 940 terminates at a magnet or ferrous material 942 that is configured to interact and anchor to a complementary magnet or ferrous material 944 supported by a helmet arm 946 supported by and connected to a helmet 948. Helmet 948 is configured to include a wireless device, a processor, and a power source (not shown) for transmitting signals from right sensor 934 and left sensor 938 to a remote electronic device.

Figure 100:
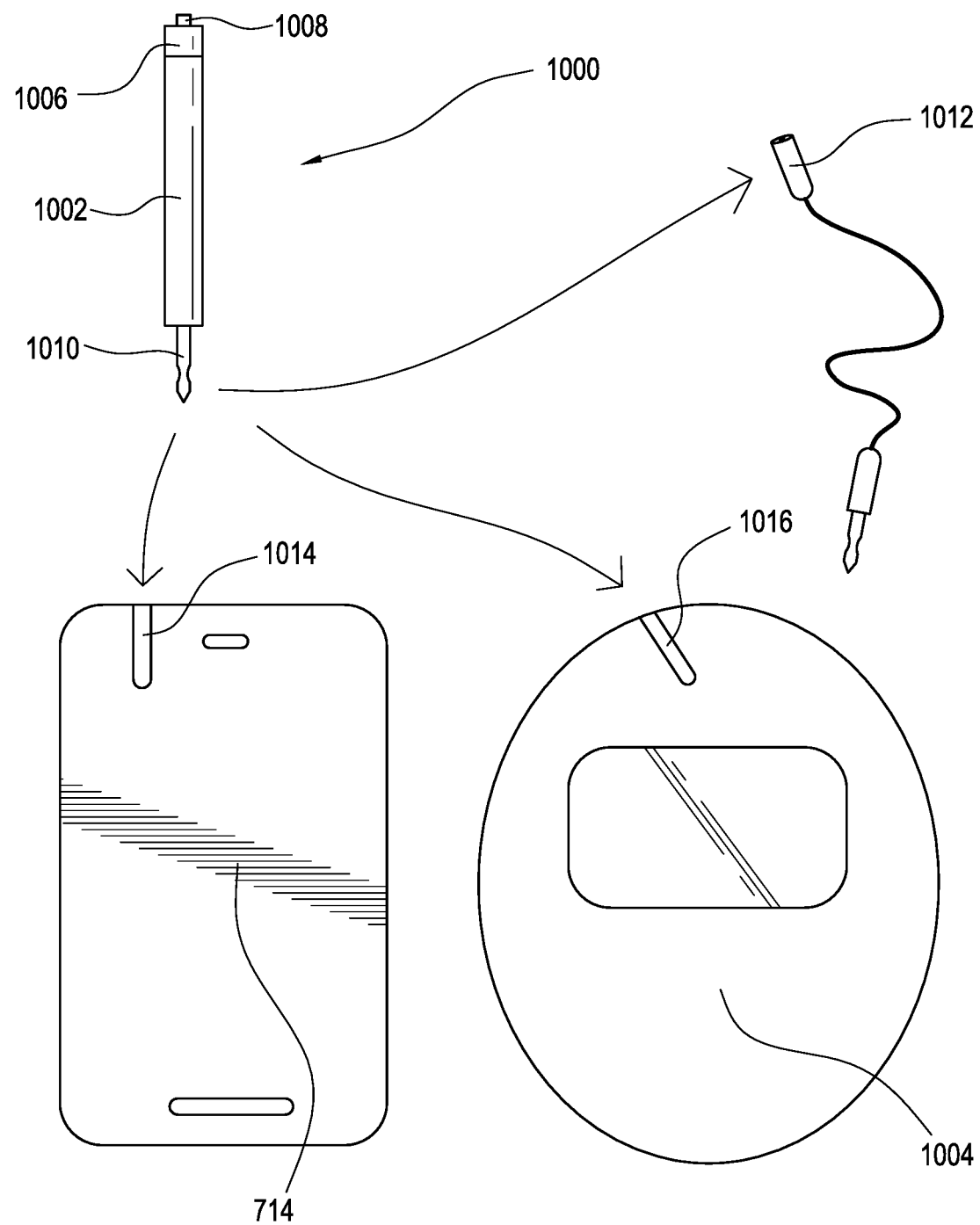
FIG. 100 shows another sensor device in accordance with an exemplary embodiment of the present disclosure.

FIG. 100 shows a view of yet another sensor device, indicated generally at 1000, in accordance with an exemplary embodiment of the present disclosure. Sensor device 1000 is similar in some respects to the embodiment of FIG. 76 and FIG. 77, and such similar elements are labeled with the same element number. Sensor device 1000 includes a cylindrical, rod-like, tubular, or pen-shaped sensor body 1002 and an electronic apparatus 714, for example a cell phone, or a specialized thermometer 1004. Specialized thermometer 1004 can be configured as, for example, an ear thermometer, an axillary thermometer, an oral thermometer, etc. Thus, specialized thermometer 1004 includes an integral temperature sensor. Sensor body 1002 includes a sensor head 1006 at a distal end and surface facing forward, on which is positioned a sensor 1008 at a free end thereof. Sensor body 1002 also includes an electrical connector 1010 positioned at a proximate end, said electrical connector adapted to connect to jack 1014 of a non-thermometric electronic apparatus 714 and jack 1016 of a specialized thermometer. Connector 1010 is configured to connect to electronic apparatus 714 and to thermometer 1004. Connector 1010 is also configured to connect to connector of cable 1012. When sensor device 1000 is connected to specialized thermometer 1004, the output from sensor device 1000 takes priority over the integral thermometer of specialized thermometer 1004. In another embodiment, a switch positioned on specialized thermometer 1004 can be positioned to select input from the integral thermometer or from sensor device 1000. When sensor device 1000 is connected to specialized thermometer 1004, the output signal from specialized thermometer 1004 is presented as a value on a display of specialized thermometer 1004.

While various embodiments of the disclosure have been shown and described, it is understood that these embodiments are not limited thereto. The embodiments may be changed, modified, and further applied by those skilled in the art. Therefore, these embodiments are not limited to the detail shown and described previously, but also include all such changes and modifications. Any part of any embodiment can be used in combination to create a single embodiment, and any part of any embodiment can be used as a replacement or addition to another embodiment, and all resultant embodiments are within the scope of the present invention.

I claim:
1. A sensor device comprising:
a cell phone including a display;
a first arm including a first end and a second end;
a second arm including a first end and a second end;

a bias material positioned to apply a force to the first end of the first arm and to the first end of the second arm to cause the first arm and the second arm to be moved toward each other, and a first sensor linked to the cell phone, the first sensor positioned on the first arm closer to the second end of the first arm than the first end of the first arm, the first sensor being configured to receive emissions from an Abreu brain thermal tunnel (ABTT) and configured to transmit a signal representative of the emissions to the cell phone, the cell phone being configured to receive the signal and configured to display an image of the emissions received.

2. The sensor device of claim 1, wherein the first sensor communicates with the cell phone by way of an electrical connector.

3. The sensor device of claim 2, including a second sensor linked to the cell phone, the second sensor positioned on the second arm closer to a second end of the second arm than the first end of the second arm.

4. The sensor device of claim 3, where each one of the first arm and the second arm is flexibly adjustable to change a spaced distance between the first sensor and the second sensor.

5. The sensor device of claim 3, the first sensor and the second sensor being positioned to face each other.

6. The sensor device of claim 1, wherein the bias material is a spring.

7. The sensor device of claim 1, the first end of the second arm and the first end of the first arm being positioned a spaced distance from each other to form a gap between the first end of the second arm and the first end of the first arm, the bias material being positioned directly between the first end of the first arm and the first end of the second arm to apply the force to the first end of the first arm and to the first end of the second arm.

8. The sensor device of claim 1, wherein the force applied by the bias material forces the first end of the first arm and the first end of the second arm away from each other while forcing the second end of the first arm and the second end of the second arm toward each other.

9. The sensor device of claim 1, wherein the first arm and the second arm extend along a first direction, and the bias material extends along a second direction that intersects the first arm and the second arm.

* * * * *